US011674167B2

(12) United States Patent
Blauwkamp et al.

(10) Patent No.: US 11,674,167 B2
(45) Date of Patent: Jun. 13, 2023

(54) SAMPLE SERIES TO DIFFERENTIATE TARGET NUCLEIC ACIDS FROM CONTAMINANT NUCLEIC ACIDS

(71) Applicant: KARIUS, INC., Redwood City, CA (US)

(72) Inventors: Timothy A. Blauwkamp, Redwood City, CA (US); Liza Huijse, Redwood City, CA (US); Michael Rosen, Redwood City, CA (US); Igor D. Vilfan, Redwood City, CA (US)

(73) Assignee: Karius, Inc., Redwood City, CA (US)

( * ) Notice: Subject to any disclaimer, the term of this patent is extended or adjusted under 35 U.S.C. 154(b) by 188 days.

(21) Appl. No.: 16/884,343

(22) Filed: May 27, 2020

(65) Prior Publication Data

US 2020/0291457 A1 Sep. 17, 2020

Related U.S. Application Data

(63) Continuation of application No. PCT/US2019/021934, filed on Mar. 12, 2019.

(60) Provisional application No. 62/644,357, filed on Mar. 16, 2018.

(51) Int. Cl.

| | |
|---|---|
| ***C12Q 1/6806*** | (2018.01) |
| ***C12Q 1/6869*** | (2018.01) |
| ***C12Q 1/6895*** | (2018.01) |
| ***G06F 17/18*** | (2006.01) |

(52) U.S. Cl.
CPC ......... *C12Q 1/6806* (2013.01); *C12Q 1/6869* (2013.01); *C12Q 1/6895* (2013.01); *G06F 17/18* (2013.01); *C12Q 2565/102* (2013.01)

(58) Field of Classification Search
CPC .. C12Q 1/6806; C12Q 1/6869; C12Q 1/6895; C12Q 2565/102; C12Q 1/6848; C12Q 1/689; G06F 17/18; C12N 15/10
See application file for complete search history.

(56) References Cited

U.S. PATENT DOCUMENTS

| | | | |
|---|---|---|---|
| 6,483,303 | B2 | 11/2002 | Simmonds et al. |
| 6,597,176 | B2 | 7/2003 | Simmonds et al. |
| 6,607,922 | B2 | 8/2003 | LaBorde |
| 6,753,137 | B2 | 6/2004 | Lo et al. |
| 6,927,570 | B2 | 8/2005 | Simmonds et al. |
| 6,969,488 | B2 | 11/2005 | Bridgham et al. |
| RE39,920 | E | 11/2007 | Umansky et al. |
| 7,323,139 | B2 | 1/2008 | LaBorde et al. |
| 7,803,929 | B2 | 9/2010 | Melkonyan et al. |
| 7,914,982 | B2 | 3/2011 | Melkonyan et al. |
| 7,973,154 | B2 | 7/2011 | Melkonyan et al. |
| 8,703,652 | B2 | 4/2014 | Quake et al. |
| 9,892,230 | B2 | 2/2018 | Lo et al. |
| 9,976,181 | B2 | 5/2018 | Christians et al. |
| 10,240,200 | B2 | 3/2019 | Koh et al. |
| 10,450,620 | B2 | 10/2019 | De Vlaminick et al. |
| 10,697,008 | B2 | 6/2020 | Blauwkamp et al. |
| 11,111,520 | B2 | 9/2021 | Blauwkamp et al. |
| 2002/0012930 | A1 | 1/2002 | Rothberg et al. |
| 2005/0202414 | A1 | 9/2005 | Jia et al. |
| 2010/0068711 | A1 | 3/2010 | Umansky et al. |
| 2012/0021412 | A1 | 1/2012 | Melkonyan et al. |
| 2012/0252686 | A1 | 10/2012 | Umbarger et al. |
| 2013/0024127 | A1 | 1/2013 | Stuelpnagel et al. |
| 2013/0178544 | A1 | 7/2013 | Melkonyan et al. |
| 2013/0245961 | A1 | 9/2013 | Lo et al. |
| 2014/0147851 | A1 | 5/2014 | Qian et al. |
| 2014/0242582 | A1 | 8/2014 | Oliphant et al. |
| 2014/0274740 | A1 | 9/2014 | Srinivasan et al. |
| 2016/0153029 | A1 | 6/2016 | Eshoo et al. |
| 2016/0304953 | A1 | 10/2016 | Chen et al. |
| 2017/0145507 | A1 | 5/2017 | Koh et al. |
| 2017/0145508 | A1 | 5/2017 | Koh et al. |
| 2017/0145509 | A1 | 5/2017 | Koh et al. |
| 2019/0256891 | A1 * | 8/2019 | Blauwkamp ......... C12Q 1/6869 |

FOREIGN PATENT DOCUMENTS

| | | | |
|---|---|---|---|
| EP | 1856295 | A2 | 11/2007 |
| EP | 1885877 | A2 | 2/2008 |
| EP | 2351857 | A1 | 8/2011 |
| WO | WO-2012159023 | A2 | 11/2012 |
| WO | WO-2012168815 | A2 | 12/2012 |
| WO | WO-2013132305 | A1 | 9/2013 |
| WO | WO-2013156627 | A1 | 10/2013 |
| WO | WO-2013159035 | A2 | 10/2013 |
| WO | WO-2014068075 | A1 | 5/2014 |
| WO | WO-2014149134 | A2 | 9/2014 |
| WO | WO-2015070086 | A1 | 5/2015 |
| WO | WO-2017165864 | A1 | 9/2017 |
| WO | 2018/031486 | A1 | 2/2018 |
| WO | WO-2018045359 | A1 | 3/2018 |

(Continued)

OTHER PUBLICATIONS

International Search Report for PCT/US2019/021934, dated May 29, 2019.
Salter, et al., "Reagent and laboratory contaimination can critically impact sequence-based microbiome analyses" BMC Biology, Nov. 12, 2014, vol. 12, No. 87, pp. 1-12.
Blauwkamp, et al. Analytical and clinical validation of a microbial cell-free DNA sequencing test for infectious disease. Nat Microbiol. Apr. 2019;4(4):663-674. doi: 10.1038/s41564-018-0349-6. Epub Feb. 11, 2019.
Chakraborty, et al. DNA barcoding to map the microbial communities: current advances and future directions. Applied microbiology and biotechnology 98.8 (Epub Feb. 13, 2014): 3425-3436.

(Continued)

*Primary Examiner* — Cynthia B Wilder
(74) *Attorney, Agent, or Firm* — Wilson Sonsini Goodrich & Rosati

(57) ABSTRACT

This disclosure provides methods, compositions and kits for determining if nucleic acids detected in a sample such as a clinical sample are derived from contaminant pathogens or clinically-relevant pathogens.

36 Claims, 18 Drawing Sheets

(56) References Cited

FOREIGN PATENT DOCUMENTS

| | | | |
|---|---|---|---|
| WO | WO-2019178157 | A1 | 9/2019 |
| WO | WO-2020106893 | A1 | 5/2020 |
| WO | WO-2020106987 | A1 | 5/2020 |

OTHER PUBLICATIONS

Chen, et al. The overlooked fact: fundamental need of spike-in controls for virtually all genome-wide analyses. Manuscript posted online Dec. 28, 2015. Mol. Cell. Biol. American Society for Microbiology, doi:10.1128/MCB.00970-14. 20 pages.

De Vlaminck, et al. Noninvasive monitoring of infection and rejection after lung transplantation. Proc Natl Acad Sci USA. Oct. 27, 2015;112(43):13336-13341. doi: 10.1073/pnas.1517494112. Epub Oct. 12, 2015.

De Vlaminck, et al. Temporal response of the human virome to immunosuppression and antiviral therapy. Cell. Nov. 21, 2013;155(5):1178-87. doi: 10.1016/j.cell.2013.10.034.

Drmanac, R. et al. Human genome sequencing using unchained base reads on self-assembling DNA nanoarrays. Science 327, 78-81 (2010).

European search report and opinion dated Nov. 9, 2021 for EP Application No. 19766804.9.

Gansauge, et al. Single-stranded DNA library preparation for the sequencing of ancient or damaged DNA. Nat Protoc. Apr. 2013;8(4):737-48. doi: 10.1038/nprot.2013.038. Epub Mar. 14, 2013.

Garaj, et al. Graphene as a sub-nanometer trans-electrode membrane. Nature. Sep. 9, 2010, 467.7312: 190-193.

GenBank Accession No. GCA_000001405.27 (replaced). RefSeq Accession: GCF_000001405.38 (replaced). GRCh38.p12. Date: Dec. 21, 2017. 3 pages. Retrieved Feb. 10, 2021 at URL: https://www.ncbi.nlm.nih.gov/assembly/GCF_000001405.38/.

Glassing, et al. Inherent bacterial DNA contamination of extraction and sequencing reagents may affect interpretation of microbiota in low bacterial biomass samples. Gut pathogens8.1 (May 26, 2016): 24. 12 pages.

Highlander, Sarah K. High throughput sequencing methods for microbiome profiling: application to food animal systems. Anim Health Res Rev. Jun. 2012;13(1):40-53. doi: 10.1017/S1466252312000126.

Huber et al. High-resolution liquid chromatography of DNA fragments on non-porous poly(styrene-divinylbenzene) particles. Nucleic Acids Res. Mar. 11, 1993;21(5):1061-6.

Kato et al. A new packing for separation of DNA restriction fragments by high performance liquid chromatography. J Biochem. Jan. 1984;95(1):83-6.

Lazarevic, et al. Decontamination of 16S rRNA gene amplicon sequence datasets based on bacterial load assessment by qPCR. BMC microbiology 16.1 (Apr. 23, 2016): 73. 8 pages.

Lindner, et al. Metagenomic abundance estimation and diagnostic testing on species level. Nucleic Acids Res. Jan. 7, 2013;41(1):e10. doi: 10.1093/nar/gks803. Epub Aug. 31, 2012.

Margulies, et al. Genome sequencing in microfabricated high-density picolitre reactors. Nature. 2005; 437:376-80.

Saukkonen, et al. Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008.

Shrestha, et al. When is a microbial culture “pure”? Persistent cryptic contaminant escapes detection even with deep genome sequencing. MBio 4.2 (Mar. 12, 2013): e00591-12.

Zook, et al. Synthetic spike-in standards improve run-specific systematic error analysis for DNA and RNA sequencing. PLoS One. 2012;7(7):e41356.

* cited by examiner

SAMPLE SERIES TO DIFFERENTIATE TARGET NUCLEIC ACIDS FROM CONTAMINANT NUCLEIC ACIDS

CROSS REFERENCES TO RELATED APPLICATIONS

This application is a continuation of and claims the benefit of International Patent Application No. PCT/US2019/021934, titled "Sample Series to Differentiate Target Nucleic Acids From Contaminant Nucleic Acids", filed Mar. 12, 2019 and U.S. Provisional Application No. 62/644,357, titled "Sample Series to Differentiate Target Nucleic Acids From Contaminant Nucleic Acids", filed 16 Mar. 2018, the entire disclosures of which are hereby incorporated herein by reference for all purposes.

BACKGROUND

Healthy samples when assessed for infectious diseases can contain pathogens as a result of environmental and/or reagent contaminants. Upon the detection of pathogens in such samples, an "artificial false positive" can result from such environmental and/or reagent contaminants. As such, there is a need in the art for more efficient and accurate methods for detecting and assessing infectious diseases.

SUMMARY

The present disclosure provides methods for detecting contaminant pathogens in a sample or in reagents used to process the sample, thereby allowing one to distinguish clinically-relevant pathogens from contaminant pathogens. In an aspect, the present disclosure provides a method of detecting contaminant nucleic acids, the method comprising: a. diluting a sample comprising cell-free target nucleic acids with a diluent to produce a dilution series comprising a first dilution and a second dilution wherein the second dilution is more dilute than the first dilution and wherein the first dilution comprises a portion of the cell-free target nucleic acids; b. performing a first sample processing on the first dilution and performing a second sample processing on the second dilution, wherein contaminant nucleic acids are possibly introduced during the first sample processing, the second sample processing, or the both the first and second sample processing; c. performing a first sequencing assay on at least a portion of nucleic acids in the first dilution to produce first sequence reads; d. performing a second sequencing assay on at least a portion of nucleic acids, if present, in the second dilution to produce second sequence reads; e. comparing the first sequence reads with the second sequence reads to obtain a relative value; and f using the relative value to distinguish the cell-free target nucleic acids from the contaminant nucleic acids.

In some embodiments, the contaminant nucleic acids and the cell-free target nucleic acids are derived from an identical type of organism. In some embodiments, the target nucleic acids or the contaminant nucleic acids comprise nucleic acids from a bacterium. In some embodiments, the bacterium is selected from the group consisting of Burholderia, Pseudomonas, Stenotrophomonas, Propionibacteria, and Methylobacteria. In some embodiments, the target nucleic acids or the contaminant nucleic acids comprise nucleic acids from a fungus. In some embodiments, the fungus is Malassezia.

In some embodiments, the contaminant nucleic acids comprise at least five contaminant nucleic acids from different species. In some embodiments, the contaminant nucleic acids comprise cell-free DNA. In some embodiments, the contaminant nucleic acids comprise cell-free RNA. In some embodiments, the target nucleic acids are detected with a specificity of greater than 80%.

In another aspect, the present disclosure provides a method of detecting contaminant nucleic acids, the method comprising: a. diluting a sample comprising target nucleic acids with a diluent to produce a dilution series comprising a first dilution and a second dilution wherein the second dilution is more dilute than the first dilution or the first dilution is more dilute than the second dilution; b. tagging at least a portion of the nucleic acids in the first dilution with a first unique identifier to produce first tagged nucleic acids; c. performing sample processing on nucleic acids within the first and second dilution, wherein contaminant nucleic acids are possibly introduced during the sample processing; d. performing a sequencing assay on the first tagged nucleic acids to produce first sequence reads; e. performing a sequencing assay on nucleic acids within the second dilution to produce second sequence reads; and f comparing a quantity of the first sequence reads and a quantity of the second sequence reads to detect the contaminant nucleic acids.

In some embodiments, the method further comprises tagging at least a portion of the nucleic acids in the second dilution with a second unique identifier to produce second tagged nucleic acids. In some embodiments, the method further comprises performing a sequencing assay on the second tagged nucleic acids to produce third sequence reads. In some embodiments, the method further comprises comparing a quantity of the first sequence reads or a quantity of the second sequence reads and a quantity of a third sequence reads to detect the contaminant nucleic acids. In some embodiments, the second tagged nucleic acids are produced by performing a ligation reaction. In some embodiments, the second tagged nucleic acids are produced by performing an amplification reaction. In some embodiments, the first unique identifier comprises a first barcode sequence. In some embodiments, the second unique identifier and the first unique identifier are different. In some embodiments, the first tagged nucleic acids are produced by performing a ligation reaction. In some embodiments, the first tagged nucleic acids are produced by performing an amplification reaction. In some embodiments, the second unique identifier comprises a second barcode sequence.

In some embodiments, the contaminant nucleic acids are derived from a microbe. In some embodiments, the contaminant nucleic acids are derived from a bacterium. In some embodiments, the contaminant nucleic acids are derived from a fungus.

In some embodiments, the sample processing comprises extracting nucleic acids, purifying nucleic acids or attaching additional sequences. In some embodiments, the sample processing comprises the attaching the additional sequences. In some embodiments, the additional sequences are selected from the group consisting of an adapter sequence, a unique identifier sequence and a barcode sequence.

In some embodiments, the sample is from a mammal. In some embodiments, the mammal is a human. In some embodiments, the human is asymptomatic for an infectious disease or an infectious condition. In some embodiments, the human is symptomatic for an infectious disease or an infectious condition. In some embodiments, the sample is selected from the group consisting of blood, plasma, serum, cerebrospinal fluid, synovial fluid, bronchial-alveolar lavage, urine, stool, saliva, and a nasal sample. In some embodiments, the sample is plasma.

In some embodiments, the first dilution is undiluted compared to the sample. In some embodiments, sample processing comprises the use of a reagent that is heated to denature contaminant nucleic acids in the reagent. In some embodiments, the diluent is heated to inactivate at least a portion of contaminant nucleic acids present in the diluent. In some embodiments, the diluent is selected from the group consisting of a buffer, a reagent, a culture medium and a synthetic plasma substitute. In some embodiments, the diluent is a buffer. In some embodiments, the buffer is selected from: extraction buffer, a suspension buffer and a lysis buffer.

In some embodiments, the method further comprises adding at least 1,000 unique spike-in synthetic nucleic acids to the sample, the first dilution or the second dilution. In some embodiments, the unique spike-in synthetic nucleic acids comprise DNA. In some embodiments, the unique spike-in synthetic nucleic acids comprise RNA. In some embodiments, the unique spike-in synthetic nucleic acids are less than 500 base pairs or nucleotides in length.

In some embodiments, the method further comprises aligning the first sequence reads to a collection of reference genomes to identify an organism from which the target nucleic acids or the contaminant nucleic acids originated. In some embodiments, the second sequence reads are aligned to a collection of reference genomes to identify an organism from which the target nucleic acids or the contaminant nucleic acids originated. In some embodiments, the collection of reference genomes comprises sequenced genomes from at least one of the following: viruses, bacteria, protozoa, or fungi.

In some embodiments, the method further comprises detecting target nucleic acids in the sample when the quantity of the first sequence reads is more than the quantity of the second sequence reads for a given nucleic acid. In some embodiments, the detecting is performed following statistical analysis. In some embodiments, the false positive rate is less than 3%. In some embodiments, the false positive rate is less than 0.1%.

In some embodiments, the method further comprises detecting an organism contaminating the diluent when the quantity of the first sequence reads is less than the quantity of the second sequence reads for a given nucleic acid. In some embodiments, the false positive rate is less than 3%. In some embodiments, the false positive rate is less than 0.1%.

In some embodiments, the method further comprises a third dilution. In some embodiments, the third dilution is more dilute than the second dilution. In some embodiments, the method further comprises performing a sequencing assay on at least a portion of the third dilution to produce fourth sequence reads. In some embodiments, the method further comprises tagging at least a portion of the nucleic acids in the third dilution with a third unique identifier to produce a third tagged nucleic acids. In some embodiments, the method further comprises performing a sequencing assay on the third tagged nucleic acids to produce fourth sequence reads.

In some embodiments, the method further comprises detecting an environmental contaminant when a quantity of the first sequence reads is not correlated with a quantity of the second sequence reads for a given nucleic acid. In some embodiments, the method further comprises detecting an environmental contaminant when the quantity of the first sequence reads is about the same as the quantity of the second sequence reads. In some embodiments, the false positive rate is less than 1%. In some embodiments, the false positive rate is less than 0.1%.

In some embodiments, the target nucleic acids and the contaminant nucleic acids are derived from a same kingdom. In some embodiments, the kingdom comprises Eubacteria, Archaea, Protista, Fungi, Plantae, and Animalia. In some embodiments, the target nucleic acids and the contaminant nucleic acids are derived from a fungi or bacteria. In some embodiments, the target nucleic acids and the contaminant nucleic acids are derived from the same type of bacterium.

In some embodiments, the sample is a negative control. In some embodiments, the negative control is selected from the group consisting of: plasma from an asymptomatic human subject, a synthetic sample designed to mimic human plasma, and a sterile sample. In some embodiments, the sample comprises plasma from an asymptomatic human subject. In some embodiments, the plasma from the asymptomatic human subject does not contain a detectable level of a first pathogen. In some embodiments, the plasma from the asymptomatic human subject comprises a detectable level of a first pathogen but not of a second pathogen.

In some embodiments, the method further comprises performing the method on a sample that does not contain a detectable level of the first pathogen. In some embodiments, the negative control is the synthetic sample designed to mimic human plasma. In some embodiments, the synthetic sample designed to mimic human plasma mimic human plasma in such a way that there are no biases across taxa with respect to efficiencies at which nucleic acids are processed and sequenced relative to natural human plasma. In some embodiments, the method further comprises performing a sequencing assay on the negative control to produce negative control sequence reads. In some embodiments, the negative control sequence reads are compared to the first sequence reads, the second sequence reads, the third sequence reads or the fourth sequence reads to eliminate background nucleic acids. In some embodiments, the negative control is diluted in a dilution series comprising a first negative control dilution and a second negative control dilution wherein the second negative control dilution is more dilute than the first negative control dilution.

In some embodiments, the sequencing assay comprises high-throughput sequencing. In some embodiments, the high-throughput sequencing comprises massively parallel signature sequencing (MPSS), Next Generation Sequencing (NGS), polony sequencing, 454 pyrosequencing, Illumina sequencing, SOLiD sequencing, ion semiconductor sequencing, DNA nanoball sequencing, heliscope single molecule sequencing, single molecule real time (SMRT) sequencing, nanopore DNA sequencing or a combination thereof. In some embodiments, the method does not comprise sequencing a 16s rRNA gene. In some embodiments, the contaminant nucleic acid is not 16s rRNA.

BRIEF DESCRIPTION OF THE DRAWINGS

The novel features of the disclosed subject matter are set forth with particularity in the appended claims. A better understanding of the features and advantages of the present disclosed subject matter will be obtained by reference to the following detailed description that sets forth illustrative embodiments, in which the principles of the disclosed subject matter are utilized, and the accompanying drawings of which:

FIG. 4 (*b*) depicts a schematic of a dilution series subjected to sample processing and further analysis, where pathogen X is present in the original sample as well as diluent and environmental contamination.

FIG. 6 (*b*) depicts inferred abundance of the same microbial pathogens and sample across dilution series.

FIG. 10 (*b*) shows depth of sequencing at different dilution factors through the count of unique normalization sequences (ddSPANK) detected in the Example 10.

FIG. 10 (*c*) shows log likelihood ratio for all the microbes detected in the dilution series of Example 10.

FIG. 10 (*d*) and FIG. 10(*e*) shows abundance in units of MPMs as a function of the dilution factor for *Aspergillus glaucus, Aspergilus ruber, Bradyrhizobium* sp., *Bacteroides vulgatus* (FIG. (*d*)) and as a dilution factor for *Bradyrhizobium yuanmingense*, *Cellulomonas* sp. leaf395 and human Herpesvirus 7 (FIG. 10(*e*)) for the microbes with value of log likelihood ratio indicating their origin in the original sample.

FIG. 10 (*f*) shows the decrease in the human reads with dilution factor as an example of a signal that is present in the original sample, and present at relatively negligible amounts in environmental contaminants and diluent.

FIG. 11(*b*) shows a trend in the total signal of the pathogen (circles) in a dilution series where the pathogen signal in the original sample is higher than the pathogen signal in the diluent and environmental contamination combined.

FIG. 11(*c*) shows a trend in the total signal of the pathogen (circles) in a dilution series where the pathogen signal in the original sample is lower than the pathogen signal in the diluent, FIG. 11(*d*) shows a trend in the total signal of the pathogen (circles) in a dilution series where the pathogen signal in the original sample is equal to the pathogen signal in the diluent.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION

Overview

The methods disclosed herein may be used to determine whether a pathogen nucleic acid detected in a clinical sample by next generation sequencing or other detection method, was present in the original clinical sample or patient, as opposed to being the result of a contaminant introduced during sample handling or processing. In addition, the methods disclosed herein may be used to determine whether contaminant nucleic acids are present in a reagent used for the processing of a clinical sample such as a reagent used in various molecular biology workflows, such as buffers, enzyme stocks, liquid powders or the like.

The methods provided herein generally provide a lower false-positive rate than methods that cannot distinguish contaminant pathogens from clinically-relevant pathogens or endogenous microbes. As such, the methods provided herein are designed to increase the clinical significance and accuracy of pathogen detection and are particularly useful for samples with low levels of signal derived from pathogen nucleic acids. Generally, the methods provided herein use a dilution series or other type of sample series in order to aid determination of the origin of a detected pathogen and help distinguish between a signal from a contaminant from a signal originating from the original sample. Indexing of members of a sample series (e.g., an indexed dilution series) may be used to compare signals across a sample series and to enable identification of contaminants. In some cases, provided herein are methods that use specially-designed controls, such as panels of negative controls with different pathogen profiles. For example, provided herein are approaches for using panels of plasma from asymptomatic patients as negative controls.

"Pathogen" as used herein refers to any organism found in association with a host organism. The pathogen may be a disease-causing or infectious agent of a host organism. The pathogen may be commensal. The pathogen may be an endogenous microbe. The pathogen may constitute a normal flora of one tissue, e.g. skin, oral cavity, etc., but is undesirable in other tissues (e.g., blood). Exemplary pathogens include, but are not limited to, viruses, bacteria (e.g., prokaryotes), microbial eukaryotes, fungi, protozoa, parasites (e.g., protozoa, helminths, and ectoparasites), nematodes, algae, and/or archeae.

Figure 1:
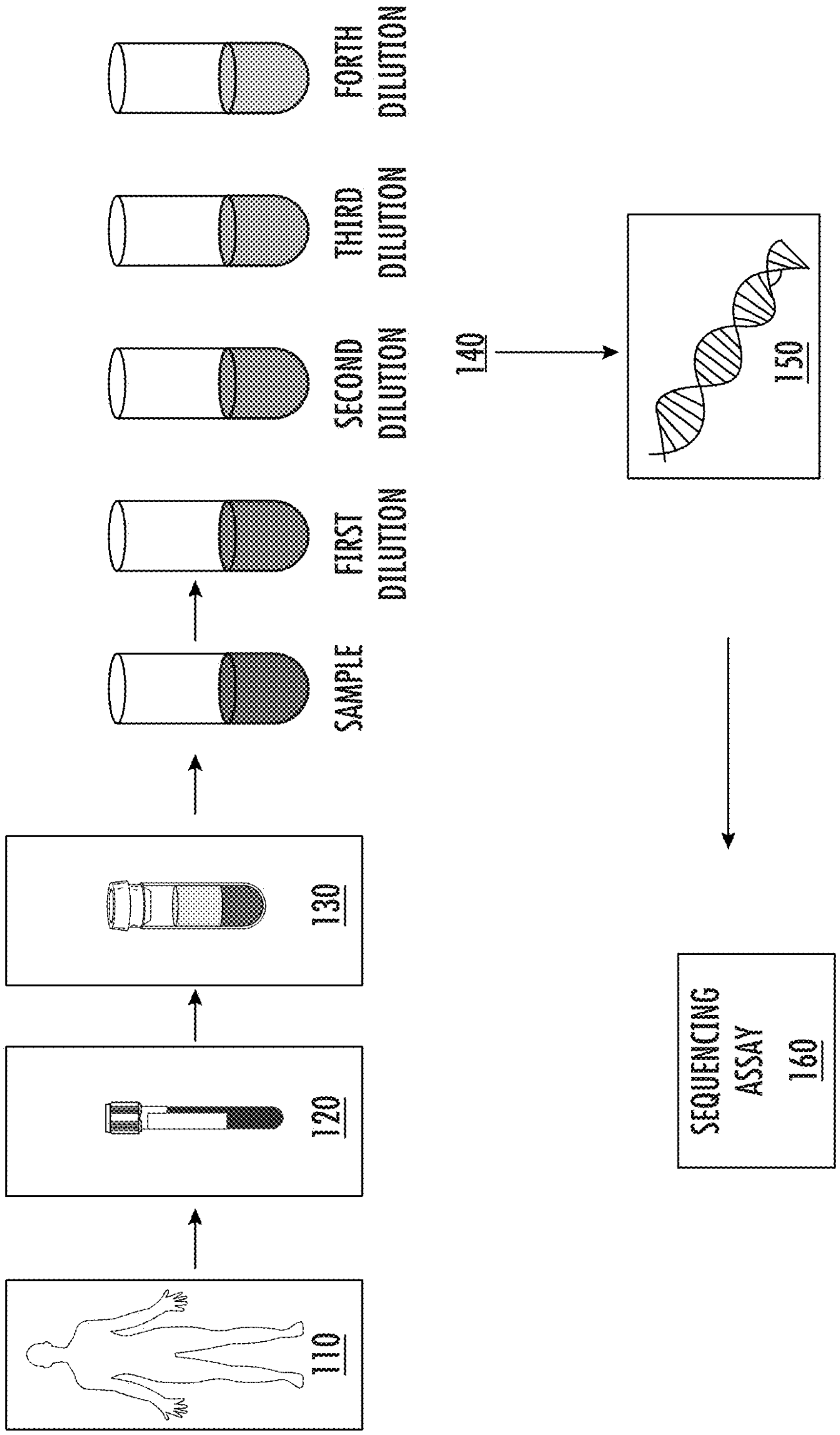
FIG. 1 shows a schematic of a basic method of this disclosure.

FIG. 1 provides a general overview of the steps of many of the methods provided herein, particularly as they relate to determining an origin of a pathogen or contaminant. The methods may involve obtaining a sample from a subject 110, such as a human patient. In some particular embodiments, the subject can have an infectious disease or is otherwise suspected of being infected with a pathogen. The sample may be a blood sample 120 or plasma sample 130, as depicted, or any other type of biological sample, especially a biological sample containing a bodily fluid (e.g., cerebrospinal fluid (CSF)), tissue, and/or cells, or a cell-free biological sample (e.g., cell-free-plasma, cell-free CSF).

In some embodiments, a dilution series 140 can be performed on the sample 120 or plasma sample 130, either of which may be cell-free (e.g., cell-free plasma sample, cell-free CSF sample). Members of the dilution series may be subjected to sample processing in parallel 150. Such sample processing may include extraction of nucleic acids (e.g., cell-free nucleic acids), lysis, purification, sequencing library preparation, and enrichment of target nucleic acids. In some cases, the members of the dilution series are tagged in some manner. For example, a unique identifier or bar code may be added to each member of a dilution series. The unique identifier or bar code may be coded to reflect the degree of dilution. For example, the first dilution may be associated with a first unique identifier and the second dilution may be associated with a different unique identifier.

The nucleic acids (e.g., cell-free nucleic acids) may be extracted and used in an assay, such as a sequencing assay (e.g., next generation sequencing assay), an amplification assay (e.g., qPCR) or a quantitative assay (e.g., microarray, qPCR) following dilution. Each dilution of a dilution series may be analyzed by a sequencing assay 160 such as a next generation sequencing assay. In some cases, following sequencing, the sequence reads can be mapped to a host reference genome, and the reads not mapped to such reference genome can be mapped to a target or non-host genome(s), algae genome(s), microbial genome(s), pathogen genome(s), for example.

Figure 11A:
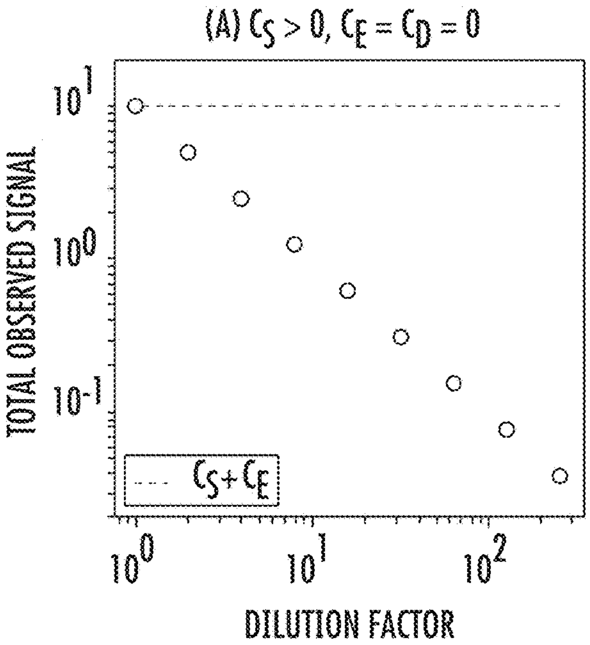
FIG. 11(*a*) shows a trend in the total signal of the pathogen (circles) in a dilution series where the pathogen signal is present only in the original sample.
Figure 11B:
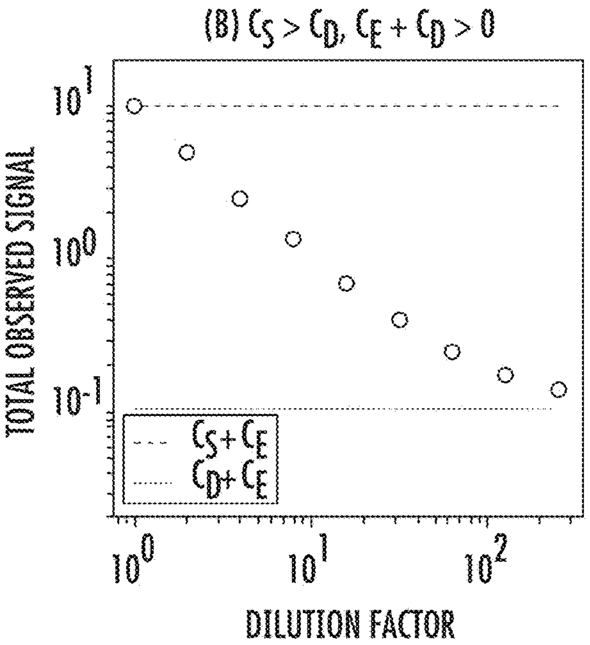
Figure 11C:
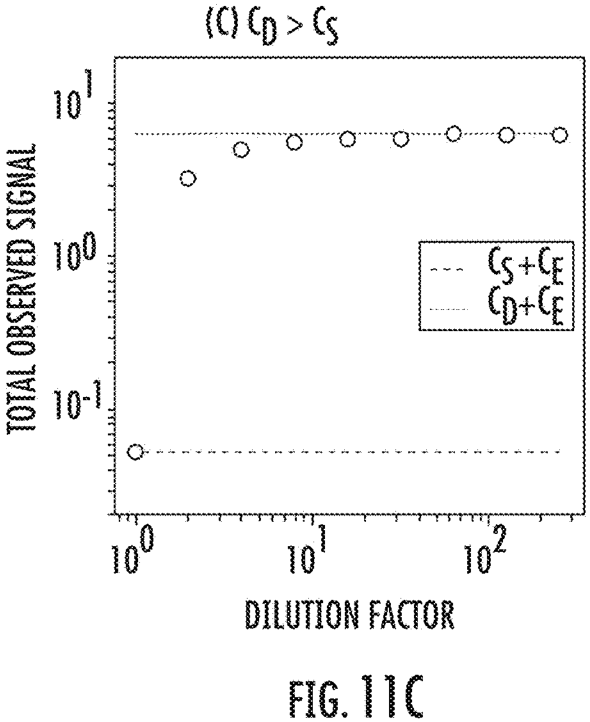
Figure 11D:
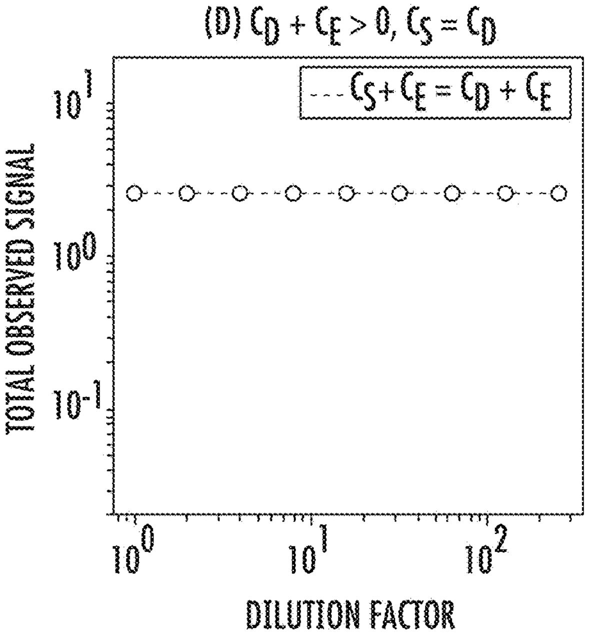

The sequencing results can be analyzed. In some cases, trends may be identified across dilutions. In undiluted samples, the total observed signal is composed of signal derived from the original test sample ($C_S$) and signal derived from environmental contamination ($C_E$). Asymptomatically, at infinite dilution, the total observed signal is comprised of signal derived from the diluent ($C_D$) and $C_E$. At intermediate dilutions, the signal will decrease with dilution if $C_S>C_D$, rise with dilution if $C_D>C_S$, or remain constant if $C_D=C_S$ (with both either equal to zero or equal to the same non-zero value). For example, if the observed total signal derives only from the original test sample (i.e. $C_D=C_E=0$), then one observes decay in signal inversely proportional to dilution throughout the dilution series (FIG. 11*a*). On the other hand, if the observed signal decays inversely proportional to dilution at small dilution factors, but asymptotes to a finite concentration, then the pathogen is present in the original test sample ($C_S>C_D>=0$), as well as the diluent and/or the environmental contamination ($C_D+C_E>0$) (FIG. 11*b*). Alternatively, if the observed signal initially increases with dilution and then asymptotes to a finite value, then the concentration of the pathogen in the diluent exceeds that in the original test sample ($C_D>C_S$), and once again the pathogen is present in the diluent and/or environmental contamination (but not necessarily in the original test sample) (FIG. 11*c*). And finally, if the observed total signal is independent of the dilution factor, then the signal in the diluent is equal to that in the original test sample ($C_D=C_S$)—for example, if it is present only in environmental contamination) (FIG. 11*d*). In these examples, the signal is measured by determining the concentration of a pathogen nucleic acid.

In some cases, the method may also comprise sequencing a set of multiple replicates from the sample at higher sequencing depths. Such replicates may have the same concentration of sample; e.g., all may be undiluted. The sequencing results may be used in conjunction with the results from the dilution analysis. For example, if the signal from the pathogen nucleic acid or non-host genome or pathogen genome(s) decreased with increasing dilutions and also remained constant over multiple sequencing depths, that may indicate that the signal is a genuine signal from the original sample as opposed to a signal introduced by a contaminant. In this example, the signal is measured by determining the concentration of a pathogen nucleic acid.

The steps described herein may be performed in any order and in any combination. In some cases, certain steps are repeated several times. In some cases, certain steps are not performed.

In some particular embodiments, the sequencing assay (e.g., next generation sequencing assay) or amplification methods (e.g. qPCR) can detect pathogen nucleic acids within a sample of cell-free nucleic acids (e.g., DNA) derived from a human patient. In some embodiments, pathogen nucleic acids can be sample derived, environment derived, or diluent derived.

In some embodiments, nucleic acids can be extracted, or purified from a sample and diluted in a dilution series. In other embodiments, a sample can comprise cell-free DNA (cfDNA) and is diluted in a dilution series. An assay (e.g. qPCR, or sequencing) can be performed on each dilution of the dilution series to determine a presence of a non-host nucleic acids and/or to determine the origin of this non-host nucleic acid (e.g. non-host nucleic acid derived from sample, diluent, diluent, dilution series, and/or environment)). For example, a sequencing library from each dilution of a dilution series can be prepared for a sequencing assay. A library of each dilution can have a unique index or barcode. In some aspects, a unique index or barcode can identify nucleic acids as being from a specific dilution of a dilution series. This can enable the detection of pathogens present in the sample, determine that a pathogen is an environmental contaminant, a reagent-based contaminant and/or derived from the original sample. "Barcode" and "barcode sequence" are used interchangeably herein.

The methods may further involve adding spike-in synthetic nucleic acids (e.g., as described in PCT/US2017/024176 titled "Synthetic Nucleic Acid Spike-Ins") to a variety of different samples including, but not limited to, clinical samples, processed samples (e.g., extracted, or purified nucleic acids, extracted or purified cell-free DNA, extracted or purified cell-free RNA, plasma, serum), unprocessed samples (e.g., whole blood), dilutions of a dilution series and any other type of sample, particularly a sample that comprises nucleic acids. In other embodiments, one or more types of synthetic nucleic acids may be added (or spiked-in) at one or more steps in the method, for example to the blood sample, to the plasma sample, to a diluent, to a first dilution, to a second dilution, to each dilution in a dilution series, or to the sample nucleic acids. A sample comprising synthetic nucleic acids may be analyzed by a sequencing assay such as a next generation sequencing assay or an amplification assay (e.g. qPCR). In some cases, the quantity of synthetic nucleic acids identified by the sequencing assay or amplification assay can be compared with the known starting concentration of the synthetic nucleic acids in order to correlate the read count with the known starting concentration. By use of such methods, and others provided herein, a condition of the subject or an origin of a pathogen or contaminant can be identified with a higher accuracy and level of certainty. In some particular embodiments, the sequencing assay (e.g., next generation sequencing assay) or amplification methods can detect pathogen nucleic acids within a sample of cell-free nucleic acids (e.g., DNA) derived from a human patient, an environmental source or a reagent.

The methods and compositions may be used to analyze samples (e.g., generating a sequencing library from target nucleic acids in the sample, quantified amplification products) from multiple subjects. The concentrations of target nucleic acids in these samples may vary among the subjects or dilutions of a dilution series. Adding the synthetic nucleic acids herein to these samples may reduce the concentration variation among the samples or dilutions of a dilution series, thus improving the accuracy of the analysis.

Figure 2:
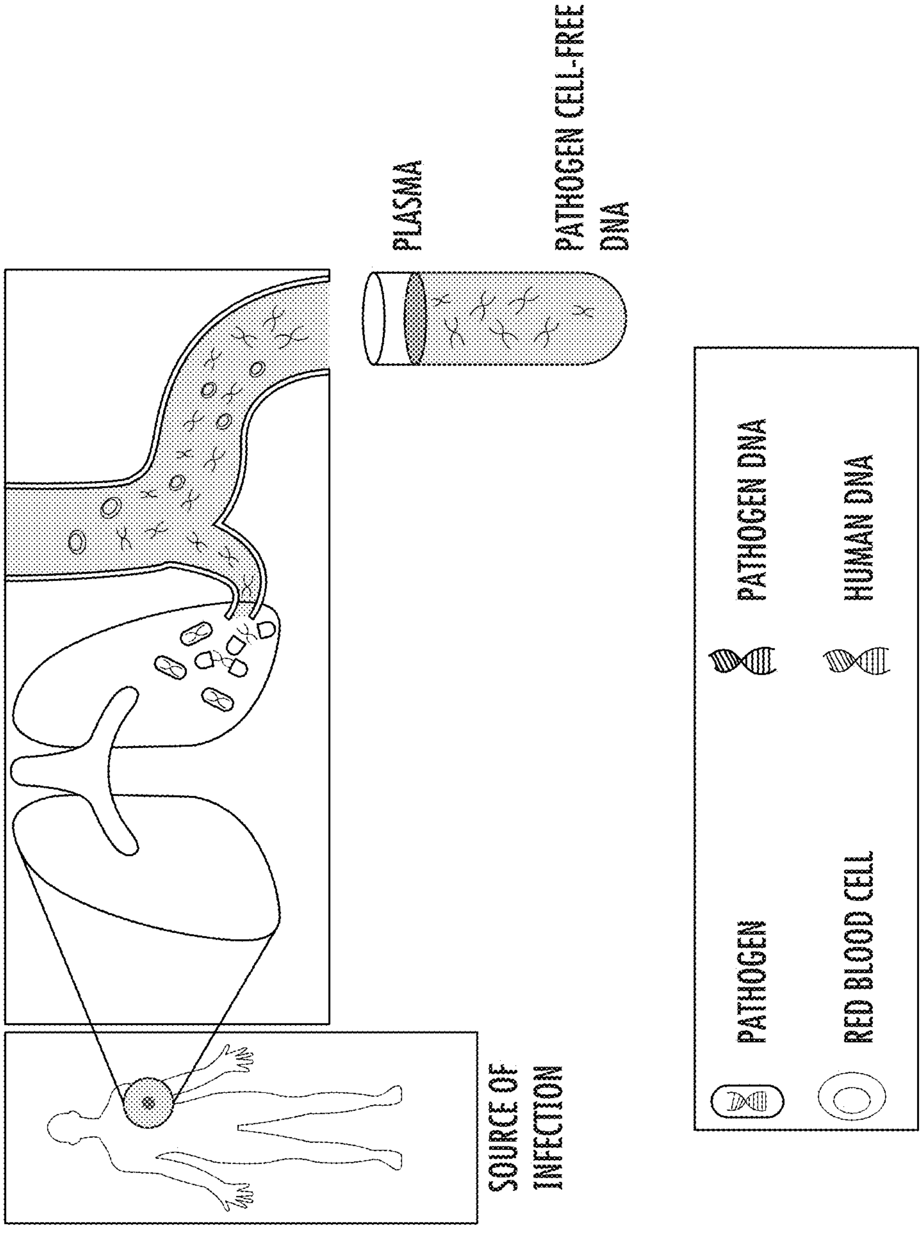
FIG. 2 shows a schematic of an exemplary infection.

FIG. 2 provides a schematic of an exemplary infection. A source of a pathogen infection may be, for example in the lung. Cell-free nucleic acids, such as cell-free DNA, derived from the pathogen may travel through the bloodstream and can be collected in a plasma sample for analysis. The nucleic acids in the sample may then be analyzed by a sequencing assay as shown in FIG. 1.

Figure 3:
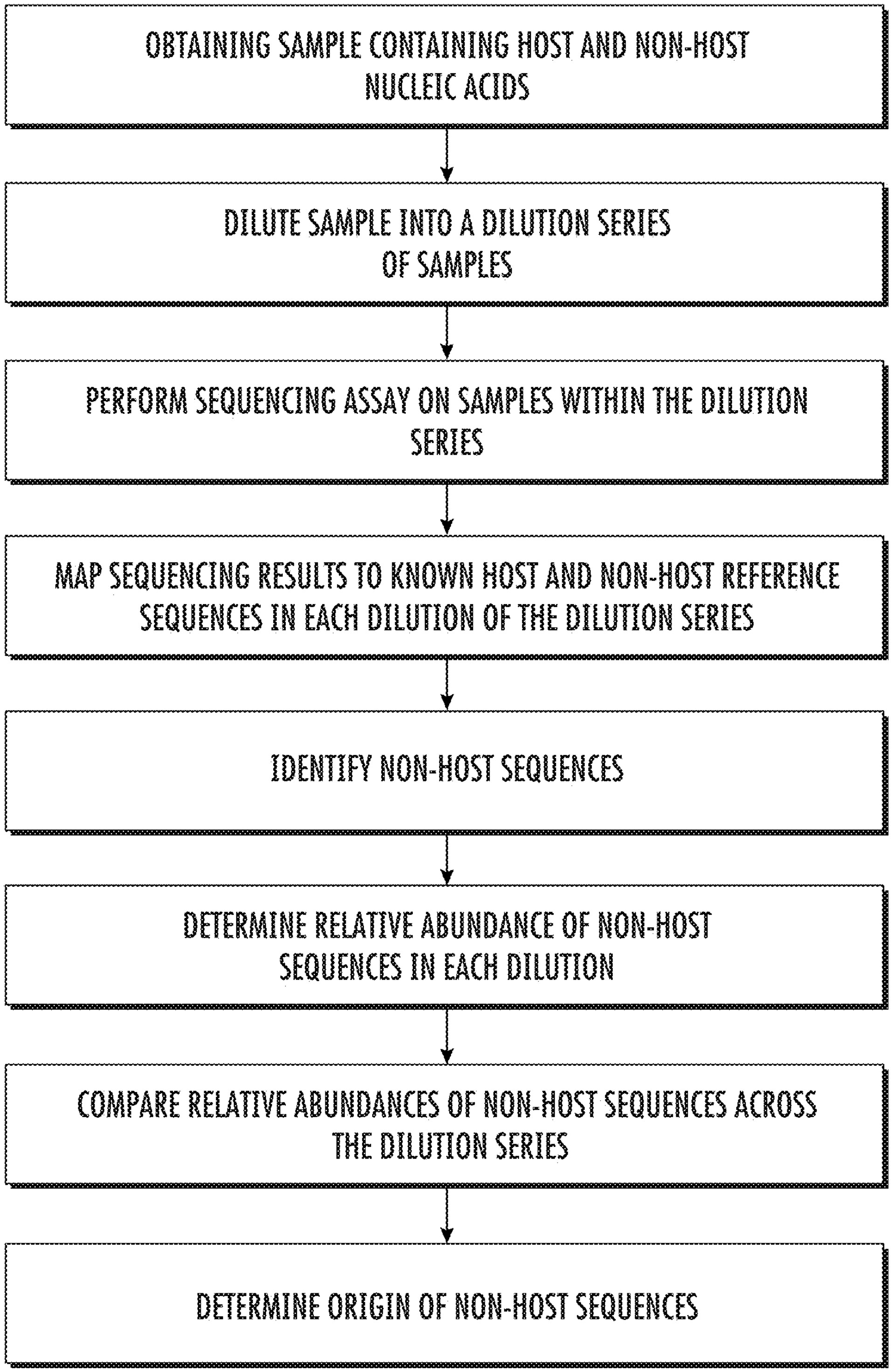
FIG. 3 depicts a general scheme of methods provided herein.

FIG. 3 depicts a general scheme of some of the methods provided herein. The methods may involve obtaining a sample containing host (e.g., human) and non-host (e.g., pathogen) nucleic acids. The sample may be obtained from a subject, such as a patient. In some particular embodiments, the subject has an infectious disease or is otherwise suspected of being infected with a pathogen or may not have a disease. The sample may be a blood sample or plasma sample, or any other type of biological sample, especially a biological sample containing a bodily fluid, tissue, and/or cells. The sample can be diluted in a dilution series (or separated into another form of sample series). The sample and/or each dilution of a dilution series can be analyzed by a sequencing assay such as a next generation sequencing assay. The sequencing results can be mapped to known host and non-host reference sequences for the sample and/or each dilution of a dilution series. In some cases, a non-host contaminant (e.g., a pathogen) can be identified in a sample or in one or more dilutions of a dilution series. The relative abundance of non-host sequences can then be determined using methods known in the art. In some cases, synthetic nucleic acids that are spiked into the sample and/or individual members of the dilution series may also be measured in order to improve identification of the relative abundance of the non-host sequences. An origin of a non-host sequence can be determined, e.g., by comparing the relative abundance of the non-host sequences across the dilution series. A non-host sequence can be determined to be sample-derived, environmental-derived, and/or reagent-derived by examining the relative levels of the non-host sequence across the dilution series.

Samples

Samples analyzed in the methods provided herein can be any type of clinical sample. In some cases, a sample can contain cells, tissue, or a bodily fluid. In some embodiments, a sample can be a liquid or fluid sample. In some cases, a sample can contain a body fluid such as whole blood, plasma, serum, urine, stool, saliva, lymph, spinal fluid, synovial fluid, bronchoalveolar lavage, nasal swab, respiratory secretions, vaginal fluid, amniotic fluid, semen or menses. In some cases, a sample can be made up of, in whole or in part, cells or tissue. In some cases, cell-free samples are obtained by removing cells, cell fragments, or exosomes by a known technique such as by centrifugation or filtration. Samples herein may be biological samples. In some cases, a sample can be a member of a dilution series. In some cases, a sample can comprise a nucleic acid from a pathogen or a contaminant. A sample may also comprise or be a reagent for one or more molecular biology or molecular diagnostics workflows. In some cases, such sample is processed alongside a sample that is a clinical sample. For example, a reagent such as an extraction buffer may be a sample provided herein; such reagent may be used to prepare a sample series or dilution series, which may be processed alongside of a sample series or dilution series for the original clinical sample.

A sample may comprise any concentration of nucleic acids. The compositions and methods herein may be useful for samples with low concentration of total nucleic acids. In some cases, a sample can have a total concentration of nucleic acid of at most 100 ng/μL, 50 ng/μL, 10 ng/μL, 5 ng/μL, 2 ng/μL, 1 ng/μL, 0.1 ng/μL, 0.05 ng/μL, 0.01 ng/μL, 10 ng/mL, 5 ng/mL, 1 ng/mL, 0.5 ng/mL, 0.1 ng/mL, 100 ng/L, 50 ng/L, 10 ng/L, 5 ng/L, 2 ng/L, 1 ng/L, 0.1 ng/L, 0.01 ng/L, 0.001 ng/L, 0.0001 ng/L, 0.00001 ng/L or 0.000001 ng/L. In some cases, a sample can have a total concentration of nucleic acid within the range from about 0.000001 ng/L to about 10,000 ng/mL.

A sample may comprise one or more controls. In some cases, a sample can comprise one or more negative controls. Exemplary negative controls include samples (e.g., plasma-minus samples) prepared to identify contaminants or environmental contaminants, plasma from healthy subjects, synthetic plasma, plasma from asymptomatic subjects, and low-diversity samples (e.g., samples collected from apparently healthy subjects). In some cases, a sample can comprise one or more positive controls. Generally, a positive control contains a natural or synthetic target pathogen nucleic acid of interest or a contaminant disclosed herein. A positive control can be a sample from a symptomatic subject, for example.

A sample may comprise target nucleic acids. In general, the term "target nucleic acid," as used herein refers to a nucleic acid that was present in a sample before the sample was subjected to sample processing. Generally, the target nucleic acid was also present in the body of the subject before a sample containing the target nucleic acid was collected from the subject. The target nucleic acid is often a nucleic acid to be tested in an assay or other process described herein. In some cases, target nucleic acids are not originally in a sample; for example, the methods may comprise testing for a target nucleic acid that turns out not to be present in the original sample. Target nucleic acids may be from a pathogen that has infected a subject. A sample may further comprise one or more synthetic nucleic acids disclosed herein. A sample may comprise a barcode sequence. In some cases, target nucleic acids can be cell-free nucleic acids described herein. For example, target nucleic acids may be cell-free DNA, cell-free RNA (e.g., cell-free mRNA, cell-free miRNA, cell-free siRNA), or any combination thereof. In certain cases, cell-free nucleic acids can be pathogen nucleic acids, e.g., nucleic acids from pathogens. Cell-free nucleic acids may be circulating nucleic acids, e.g., circulating tumor DNA, circulating donor DNA or circulating fetal DNA. A sample may comprise nucleic acid from pathogens, e.g., viruses, bacteria, fungi, and/or eukaryotic parasites.

As used herein, the term "contaminant nucleic acid" refers to a contaminant nucleic acid introduced into the sample during or after sample collection. Most often, the contaminant nucleic acids described herein are introduced from the environment during a sample processing step such as nucleic acid extraction, lysis, purification, centrifugation, filtration process, sample handling or library preparation. The contaminant nucleic acid may be, for example, a nucleic acid shed by a person handling a sample, a nucleic acid present in the environment in which the sample is handled, a nucleic acid present in a reagent used to process the sample, or any other type of contaminant. The contaminant may be, for example, a nucleic acid derived from a human, pathogen, bacterium, fungus, parasite, virus, or any other source outside of the original sample. In some cases, a contaminant nucleic acid is derived from the same or identical type of organism that the target nucleic acid is derived from. For example, in some cases, a contaminant nucleic acid and a target nucleic acid are derived from the same type or taxon of pathogen, the same type or taxon of bacterium, the same type of taxon of virus, the same type or taxon of fungus, or the same type or taxon of parasite. In such cases, a contaminant nucleic acid may have the same sequence as the target nucleic acid.

The term "barcode" or "unique identifier" is used interchangeably herein. In some cases a spike-in can comprise a barcode. In other cases, a spike-in can be a barcode.

The term "attach" and its grammatical equivalents may refer to connecting two molecules using any mode of attachment. For example, attaching may refer to connecting two molecules by covalent or non-covalent chemical bonds or other method to generate a new molecule or complex. In some cases, attach can be a direct or indirect attachment, e.g., through a linker. Attaching an adapter to a nucleic acid may refer to forming a chemical bond between the adapter and the nucleic acid. In some cases, attaching is performed by ligation, e.g., using a ligase.

A sequencing library may be generated from a sample using the methods and compositions provided herein. A sequencing library may comprise a plurality of nucleic acids that are compatible with a sequencing system to be used. For example, nucleic acids in a sequencing library may comprise a target nucleic acid attached with one or more adapters. Steps for preparing a sequencing library may include one or more of: extracting target nucleic acids from a sample, fragmenting the target nucleic acids, end-repair (e.g., repairing damaged nucleic acids (phosphorylation of 5'-ends, desphosphorylation of 3'-ends, nick translation, abasic site repair, blunting the ends of double-stranded nucleic acids etc.), general dephopshorylation with phosphatases, primer extension, template-switching, addition of nucleotides to the 3' terminus of a nucleic acids, splint ligation, attaching adapters to the target nucleic acids, amplifying the target nucleic acid-adapter complexes and sequencing the amplified target nucleic acid-adapter complexes.

The library preparation can be used on single-stranded or double-stranded nucleic acids. In some embodiments, the library preparation comprises the steps: (1) denaturation; (2) hybridization; (3) ligation; or (4) amplification. In some embodiments, the library preparation comprises the steps: (1) denaturation; (2) addition of nucleotides to the 3' terminus of a nucleic acids; (3) primer extension and/or template-switching; or (4) amplification. In other embodiments, the single-stranded or double-stranded method can consist of the steps: (1) denaturation; (2) hybridization and primer extension; (3) ligation; and (4) amplification. In some applications, a single-stranded or double-stranded library can be prepared by simultaneously ligating the adapters or splint oligomers at both ends. Such preparation can provide the benefit of increasing the yield of the library. In some applications, the methods provided herein may increase the yield by a factor of 1, 2, 3, 4, 5, 6, 7, 8, 9, or 10. In some instances, the simultaneous ligation can be achieved using splinted ligation with degenerate ends to facilitate hybridization to the template molecules. In some embodiments, the ends of the adapters and splint molecules can be protected to achieve the intended ligation reaction. Some examples of ligase enzymes that can be used with the methods provided herein include but are not limited to T4 DNA Ligase, SplintR Ligase, or the like. In other embodiments, the opposite polarities of the degenerate overhangs in each adapter-splint hybrids can be used which can also provide the benefit of increasing the yield. In some cases, the methods provided herein may increase the yield by a factor of 1, 2, 3, 4, 5, 6, 7, 8, 9, or 10.

Depending on the library preparation, one can use various adapters or splint oligomers with deactivated ends in the library preparation using a process involving simultaneous ligation. In some aspects, one can use splint oligomers that have both the 5' and 3' ends deactivated of the 3' splint oligomer. In some aspects, one can use splint oligomers that have both the 5' and 3' ends deactivated of the 5' splint oligomer. In other aspects, one can use an adapter oligomers with the 3' deactivated of the 3' adapter oligomer. In other aspects, one can use an adapter oligomers with the 5' deactivated of the 5" adapter oligomer.

Generally, samples can be from a human subject, especially human patients. But the samples may also be from any other type of subject including any mammal, non-human mammal, non-human primate, domesticated animal (e.g., laboratory animals, household pets, or livestock), or non-domesticated animal (e.g., wildlife). In some particular embodiments, the subject is a dog, cat, rodent, mouse, hamster, cow, bird, chicken, pig, horse, sheep, rabbit, ape, monkey, or chimpanzee. In some embodiments, samples can be food samples, pharmaceutical products, water, reagents, buffers or beverages. In some embodiments, samples can be non-biological samples.

In embodiments, a subject can be a host organism (e.g., a human) infected with a pathogen, at risk of infection by a pathogen, or suspected of having a pathogenic infection. In some cases, a subject can be suspected of having a particular infection, e.g., suspected having tuberculosis. In other cases, a subject can be suspected of having an infection of unknown origin. In some cases, a host or subject is infected (e.g., with one or more microbes, pathogens, bacteria, viruses, fungi, or parasites). In some cases, a host or subject may have been diagnosed with or is at risk for developing one or more types of cancer. In some cases, a host or subject can be an organ or cell transplant recipient or donor. In some cases, a host or subject may not be infected (e.g., with one or more microbes, pathogens, bacteria, viruses, fungi, or parasites). In some cases, a host or subject can be healthy. In some cases, a host or subject can be susceptible or at risk of an infection.

In some cases, a subject may have been treated or may be treated with an antimicrobial, antibacterial, antiviral, or antiparasitic drug. A subject may have an actual infection (e.g., with one or more microbes, pathogens, bacteria, viruses, fungi, or parasites). In some cases, a subject may not be infected (e.g., with one or more microbes, pathogens, bacteria, viruses, fungi, or parasites). In some cases, a subject is healthy. In some cases, the subject may be susceptible or at risk of an infection (e.g., patient is immunocompromised). A subject may have or be at risk of having another disease or disorder. For example, a subject may have, be at risk of having, or be suspected of having a disease such as cancer (e.g., breast cancer, lung cancer, pancreatic cancer, hematological cancer, etc.).

A sample may be a nucleic acid sample; in some cases, the sample may contain a certain amount of nucleic acids. Nucleic acids within a sample may include double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, phage DNA, bacterial nucleic acids, fungal nucleic acids, parasite nucleic acids, viral nucleic acids, cell-free bacterial nucleic acids, cell-free fungal nucleic acids, cell-free parasite nucleic acids, viral particle-associated nucleic acids, viral-particle free nucleic acids, or any combination thereof. In some cases, sample nucleic acids may include synthetic nucleic acids. In some cases, synthetic nucleic acids include any types of nucleic acids disclosed herein, e.g., DNA, RNA, DNA-RNA hybrid. For example, a synthetic nucleic acid may be DNA. In preferred embodiments, the sample is a cell-free nucleic acid sample, which is a sample that has been processed in some manner to obtain cell-free nucleic acids. In some cases, the sample is a cell-free DNA sample. In some cases, the sample is a cell-free RNA sample.

In some cases, different types of nucleic acids may be present in a sample. For example, the sample may comprise cell-free RNA and cell-free DNA. Likewise, a method provided herein may include a method where both RNA and DNA present in a sample are analyzed, singly or in combination.

As used herein, the term "cell-free" refers to the condition of the nucleic acid as it appeared in the body before the sample is obtained from the body of subject. For example, circulating cell-free nucleic acids in a sample may be from cell-free nucleic acids circulating in the bloodstream of the human body. Such cell-free nucleic acids may have been released from dying cells (e.g., apoptotic cells, necrotic cells, etc.) or fragments of cells. In contrast, nucleic acids that are extracted from a solid tissue, such as a biopsy, in which they were present in a cell-associated form, are generally not considered to be "cell-free" as used herein.

Cell-free samples are generally obtained by removing cells from a biological sample. In some cases, cell-free samples are samples from which human cells have been removed, such as by centrifugation, filtration, or any other method known in the art. In some cases, cell-free samples are samples from which human and microbial cells (e.g., bacterial cells and/or fungal cell and/or parasite cells) have been removed. In some cases, cell-free samples are samples where viral particles have been removed; in such cases, the cell-free nucleic acids are viral particle-free nucleic acids, in that they are not associated with viral particles. In some cases, cell-free samples are samples where viral particles have not been removed; in such cases, the cell-free nucleic acids include both viral-particle-associated nucleic acids and viral-particle-free nucleic acids. Removal of intact bacteria, fungus, parasites and viral particles from a sample is well-known in the art and may include centrifugation a (e.g., 10,000 g, or higher accelerations), ultracentifugation, filtration, ultrafiltration, or any other known method of removing microbial cells from a sample.

Although cell-free nucleic acids are generally extracellular nucleic acids, in some cases lysis is used in the preparation of a cell-free sample. For example, lysis of red blood cells or vesicles may be performed when preparing a cell-free sample. In some cases, preparing a cell-free sample may include removing proteins associated with nucleic acids.

In some cases, a sample may be an unprocessed sample (e.g., whole blood) or a processed sample (e.g., serum, plasma, cell-free plasma) that contains cell-free or cell-associated nucleic acids. In some cases, a sample may have been enriched for a certain type of nucleic acid, e.g., DNA, RNA, cell-free DNA, cell-free RNA, cell-free circulating DNA, cell-free circulating RNA, etc. In some cases, a sample may have been processed in some way to isolate nucleic acids or to separate nucleic acids from other components within the sample. In some cases, a sample may have been enriched for pathogen-specific nucleic acids.

Often, a sample can be a fresh sample. In some cases, a sample can be a frozen sample. In some cases, a sample can be fixed, e.g., with a chemical fixative such as formalin-fixed paraffin-embedded tissue. When obtaining a sample from a subject (e.g., blood sample), the amount can vary depending upon subject size and/or a condition being screened. In some embodiments, at least 10 ml, 5 ml, 1 ml, 0.5 ml, 250, 200, 150, 100, 50, 40, 30, 20, 10, 9, 8, 7, 6, 5, 4, 3, 2, or 1 μL of a sample is obtained. In some embodiments, 1-50, 2-40, 3-30, or 4-20 μL of sample is obtained. In some embodiments, input volumes as described herein can include an input volume of 25 μl, 50 μl, 100 μl, 500 μl, 1 ml, 2 ml, 5 ml, 10 ml, or more.

Control Samples

The methods provided herein may be conducted using one or more control samples such as negative or positive control samples. Positive control samples generally contain a detectable level of a pathogen of interest. In contrast, negative control samples may lack a detectable level of one or more pathogen nucleic acids of interest. In some cases, pathogen nucleic acids of interest may be present in the negative control sample; but generally, they are present below a baseline value. The negative control samples may be processed in parallel with a test sample at any step of sample processing, including steps such as extraction, purification, library preparation and sequencing. In general, detected levels of pathogens in the test samples are compared with the negative control sample in order to determine presence or absence of pathogen nucleic acids in the test sample, to quantify the level of pathogen nucleic acids in the test sample, or to identify potential contaminants.

Negative control samples may be used to aid or improve methods of detecting target nucleic acids and/or contaminant nucleic acids. For example, in order to detect contaminants in a sample, clinical or test samples may be sequenced or processed concomitantly with negative control samples. This can allow for a statistical characterization of the signal expected from the environmental contaminant, which can then be deconvolved from the sample-derived DNA in clinical samples.

In some cases, specific negative control samples may be used to increase the sensitivity or accuracy of an assay. For certain taxa or types of pathogens, a negative control sample such as a control sample that is made up mostly of buffer may have systematically lower signals as compared to plasma samples. Use of such a negative control sample may lead to a false positive call for a test sample (e.g., clinical sample) that is compared to such negative control sample. In such cases, use of a negative control sample that emulates the basic and/or major components of the test sample may reduce false positive hits. For example, when the test sample is a plasma sample, a negative control sample that is also made up of plasma may be a superior control to an ordinary buffer in an assay to detect certain types of pathogens. This is because the efficiency of sample processing and eventual sequencing of genetic material may be different in the buffer-based control, which can lead to an increased risk of false positives or loss in sensitivity.

In some cases, the negative control sample (e.g., plasma, serum or other biological fluid) is obtained from an asymptomatic subject. A sample obtained from a subject asymptomatic for one or more pathogens or infections is referred to herein as an "asymptomatic sample." For example, plasma obtained from a subject asymptomatic for one or more pathogens or infections is referred to herein as "asymptomatic plasma." In some cases, multiple batches or stocks of negative control samples (e.g., asymptomatic plasma) are obtained from a single subject; in other cases, multiple batches or stocks of negative control samples (e.g., asymptomatic plasma) are obtained from multiple different subjects.

In some cases, a panel of negative control samples may be used in the methods provided herein. The panel can comprise one or more batches or stocks of control samples. In particular embodiments, the panel of negative control samples may have different pathogen nucleic acid profiles. Particularly useful is a panel of negative control samples wherein each sample is negative for a different taxon or type of pathogen nucleic acids. For example, negative control sample 1 may have a detectable level of pathogen A, a detectable level of pathogen B, and no detectable level of pathogen C. A panel of negative control samples provided herein may thus contain negative control sample 1, as well as additional negative control samples that include at least one control sample that lacks a detectable level of pathogen A and at least one control sample that lacks a detectable level of pathogen B. In preferred embodiments, the negative control samples are plasma, particularly plasma from different asymptomatic subjects.

In some particular cases, a dilution series is used to detect pathogens in a plasma sample or other sample from various asymptomatic subjects or patients. The dilution series can be used to determine the plasma-derived signal of a particular lot of asymptomatic plasma. This asymptomatic plasma can then be used as a negative control, particularly for a pathogen that is not identified as plasma-derived for that particular lot of asymptomatic plasma. In some cases, a first asymptomatic plasma that lacks a detectable level of pathogen A may be used to detect pathogen A. In cases where the first asymptomatic plasma contains pathogen A, the asymptomatic plasma may be used to detect pathogen B, thereby increasing the sensitivity of the overall method for detecting pathogen B. In order to expand the negative control to cover those remaining taxa (e.g., pathogen B in the preceding example), one can repeat the dilution series for additional asymptomatic plasmas until one has a set of asymptomatic plasmas with plasma-derived signals present in disjoint sets of taxa. In some cases, the subset of negative controls that are negative for a particular taxon or type of pathogen is used to characterize the expected environmental contamination levels of that taxon or type of pathogen. In some embodiments, at least 1, 2, 3, 4, 5, 6, 7, 8, 9 or 10 negative controls can be used per pathogen. In some cases, such negative controls are positive for different sets of pathogens. In other embodiments, at least 1, 2, 3, 4, 5, 6, 7, 8, 9 or 10 positive controls can be used per pathogen. In some cases, 1 out of 4, 2 out of 4, and 3 out of 4 negative controls of asymptomatic plasma are negative for a particular pathogen.

A negative control used in the present methods may include any type of negative control, including but not limited to buffers, aqueous buffers, water, or a biological sample. Biological samples useful as negative controls may include a sample from a healthy subject, a sample from an asymptomatic subject, or a sample from a subject with a disease or disorder. In some cases, the biological sample used as a negative control is obtained from the same subject that provided the sample to be tested, e.g., a subject suspected of having a pathogen infection; in such cases, the negative control sample from the subject may have been taken at an earlier time point such as at a time point when the subject was asymptomatic. In some cases, the negative control is obtained from a subject different than the subject from which the test sample was derived.

The presence or absence of a target nucleic acid or a contaminant in the negative control sample (e.g., asymptomatic plasma) may be detected in any manner known in the art. In some cases, a dilution series provided herein is used to detect a target nucleic acid or contaminant in the negative control sample (e.g., asymptomatic plasma). For example, the negative control sample may be diluted into a dilution series (or other sample series) and may be subjected to sample processing, including next generation sequencing. The members of the dilution series may then be compared in order to determine trends in the pathogen signal and ultimately, to determine whether (or confirm that) the pathogen signal originated in the negative control sample.

Another approach can be to use synthetic samples as negative controls; such synthetic samples may possess biochemical properties that mimic those of the biological sample in question (e.g. plasma) in such a way that there are no biases or reduced biases across taxa in the efficiencies at which nucleic acids molecules are processed and sequenced relative to true biological sample (e.g. true plasma). In some cases, a dilution series can be used to characterize which taxa are present in the synthetic sample (e.g., synthetic plasma). Synthetic samples (e.g., Horizon Discovery, USA synthetic plasma samples) with confirmed profiles of taxa may then be used as negative controls or diluents in the methods provided herein.

In some cases, a negative control sample or a panel of negative control samples described herein may be used as diluents in a dilution series disclosed herein. For example, samples obtained from one or more asymptomatic subjects may be used as diluents in a dilution series disclosed herein. In some aspects, a diluent can be asymptomatic plasma.

Target Nucleic Acids

The methods provided herein may be used to detect any number of target nucleic acids. The target nucleic acids include but are not limited to: whole or partial genomes, exomes, genetic loci, genes, exons, introns, modified nucleic acids (e.g., methylated nucleic acids), and/or mitochondrial nucleic acids, transcripts. Often, the methods provided herein can be used to detect pathogen target nucleic acids; in some cases, the pathogen target nucleic acids can be present in complex clinical sample containing nucleic acids from the subject. The pathogen target nucleic acid may be associated with an infectious disease, such as influenza, tuberculosis, or any other known infectious disease or disorder, including those described further herein. In some cases, a nucleic acid described herein may be a target nucleic acid.

In some cases, a pathogen target nucleic acid can be present in a tissue sample, such as a tissue sample (e.g., biopsy) from a site of infection. The methods provided herein may be used to detect, monitor or assess such types of pathogen nucleic acids.

In some cases, pathogen target nucleic acids may be cell-free nucleic acids, as described herein. For example, pathogen target nucleic acids may have migrated from the site of infection, either associated with a pathogen cell, associated with a viral particle, or in a cell-free and/or particle-free form. In some cases, pathogen target nucleic acids may be obtained from a sample containing cell-free nucleic acids (e.g., DNA), such as cell-free nucleic acids present in a body fluid (e.g., circulating cell-free nucleic acids).

In some cases, target nucleic acid can be derived from cancer tissue. Target nucleic acid may be obtained directly from the tissue or tumor. In some cases, target cancer nucleic acid can be obtained from circulating cell-free nucleic acids or from circulating tumor cells (CTCs).

In some cases, target nucleic acid may make up a very small portion of an entire sample, e.g., less than 1%, less than 0.5%, less than 0.1%, less than 0.01%, less than 0.001%, less than 0.0001%, less than 0.00001%, less than 0.000001%, 0.0000001%, 0.00000001%, 0.00000000001% or less than 0.0000000000001% of the total nucleic acids in a sample. In some cases, target nucleic acid may make up from about at least about 0.00000000001% to at least about 0.5% of the total nucleic acids in a sample. Often, the total nucleic acids in an original sample may vary. For example, total cell-free nucleic acids (e.g., DNA, mRNA, RNA) may be in a range of 0.001-100 ng/ml, e.g., (about 0.001, 0.01, 0.1, 1, 5, 10, 20, 30, 40, 50, 80, 100 ng/ml). In some cases, the total concentration of cell-free nucleic acids in a sample is outside of this range (e.g., less than 0.001 ng/ml; in other cases, the total concentration is greater than 100 ng/ml). In some case, cell-free nucleic acid (e.g., DNA) samples may be predominantly made up of human DNA and/or RNA. In such samples, pathogen target nucleic acids or cancer target nucleic acids may have scant presence compared to the human or healthy nucleic acids, for example with a sample from a subject undergoing chemotherapy. For example, pathogen target nucleic acids may make up less than 0.001% (e.g., 0.0001% to 0.001%; 0.00001%; or 0.00000000001% to 0.001%) of total nucleic acids in a sample, and cancer target nucleic acids may make up less than 1% of total nucleic acids in a sample.

The length of target nucleic acids can vary. In some cases, target nucleic acids may be about or at least about 20, 30, 40, 50, 60, 70, 80, 90, 100, 110, 120, 130, 140, 150, 160, 170, 200, 250, 300, 350, or 400, 500, 1000, 2000, 3000, or 4000, nucleotides (or base pairs) in length. In some cases, target nucleic acids may be up to about 20, 30, 40, 50, 60, 70, 80, 90, 100, 110, 120, 130, 140, 150, 160, 170, 180, 190, 200, 250, 300, 350, 400, 500, 1000, 2000, 3000, or 4000 nucleotides (or base pairs) in length. In some particular embodiments, the target nucleic acids may be relatively short, e.g., less than 500 base pairs (or nucleotides) or less than 1000 base pairs (or nucleotides) in length. In some cases, the target nucleic acids may be relatively long, e.g., greater than 1000, greater than 5000 base pairs (or nucleotides) in length. In some cases, target nucleic acids may be in the range from about 20 to about 120 base pairs. In some cases, target nucleic acids may be in the range from about 40 to about 100 base pairs.

As is the case with the sample nucleic acids, target nucleic acids may be any type of nucleic acid including: double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, algae nucleic acids, archaea nucleic acids, bacterial nucleic acids, fungal nucleic acids, parasite nucleic acids, viral nucleic acids, cell-free algae nucleic acids, cell-free archaea nucleic acids, cell-free bacterial nucleic acids, cell-free fungal nucleic acids, cell-free parasite nucleic acids, viral particle-associated nucleic acids, viral-particle free nucleic acids or any combination thereof. The target nucleic acids may be nucleic acids derived from pathogens including but not limited to viruses, bacteria, fungi, parasites and any other microbe, particularly an infectious microbe. In some cases, the target nucleic acids may be derived directly from the subject, as opposed to a pathogen. In some cases, target nucleic acids may be derived from an environmental source or a reagent. Target nucleic acid described herein may be representative of a presence of a viruses, bacteria, fungi, or parasite, for example *Acinetobacter baumannii; Actinomyces*, including *Actinomyces israelii, Actinomyces gerencseriae*, and *Proprionibacterium propionicus; Anaplasma* including *Anaplasma phagocytophilum; Bacillus*, including *Bacillus anthraces* and *Bacillus cereus; Arcanobacterium* including *Arcanobacterium haemolyticum; Bacteroides; Borrelia; Brucella; Burkholderia* including *Burkholderia cepacia* and *Burkholderia pseudomalli; Mycobacterium* including *Mycobacterium ulcerans, Mycobacterium leprae*, and *Mycobacterium lepromatosis; Enterobacteriaceae; Enterococcus; Campylobacter; Bartonella* including *Bartonella henselae; Streptococcus* including *Streptococcus pneumoniae, Streptococcus pyogenes*, and *Streptococcus agalactiae; Haemophilus* including *Haemophilus ducreyi* and *Haemophilus influenzae; Chlamydia* including *Chlamydia trachomatis; Chlamydophila* including *Chlamydophila pneumonia* and *Chlamydophila trachomatis; Vibrio* including *Vibrio cholera; Clostridium* including *Clostridium difficile, Clostridium botulinum*, and *Clostridium perfringens; Corynebacterium* including *Corynebacterium diphtheriae; Rickettsia* including *Rickettsia prowazekii, Rickettsia akari, Rickettsia rickettsii*, and *Rickettsia typhi; Ehrlichia* including *Ehrlichia ewingii* and *Ehrlichia chaffeensis; Fusobacterium; Neisseria* including *Neisseria gonorrhoeae* and *Neisseria meningitidis; Klebsiella* including *Klebsiella granulomatis; Helicobacter* including *Helicobacter pylori; Kingella* including *Kingella kingae; Legionella* including *Legionella pneumophila; Nocardia; Bordetella* including *Bordetella pertussis; Listeria* including *Listeria monocytogenes; Shigella; Salmonella; Campylobacter* including *Campylobacter coli* and *Campylobacter jejuni*; and *Yersinia* including *Yersinia pseudotuberculosis, Yersinia enterolitica*, and *Yersinia pestis.*

Target nucleic acids described herein can also be representative of a presence of Fungi, yeasts, molds, and similar populations. These include but are not limited to organisms of the genera *Aspergillus, Piedraia, Blastomyces, Candida, Fonsecaea, Coccidioides, Cryptococcus, Geotrichum, Microsporidia, Malassezia*, and *Trichosporon.*

Dilution

Disclosed herein are methods and kits that may be used to determine if a nucleic acid detected in a sample is truly present in the sample or is an environmental contaminant or a reagent contaminant. The methods described herein can be performed as a sample series (e.g., dilution series or serial dilution). A sample series can be used to determine if a quantity of a target nucleic acid (e.g. non-host nucleic acid, pathogen nucleic acid or a contaminant nucleic acid) increases, decreases, stays the same or does not correlate across the sample series, serial dilution or dilution series. A sample series can also be used to determine if a quantity of a target nucleic acid (e.g. non-host nucleic acid, pathogen nucleic acid or a contaminant nucleic acid) asymptotically approaches non-zero or zero or background quantity in the limit of infinite dilution. A sample series can also be used to determine if a quantity of a target nucleic acid (e.g. non-host nucleic acid, pathogen nucleic acid or a contaminant nucleic acid) is a non-zero or zero or background quantity in the undiluted sample.

Figure 4A:
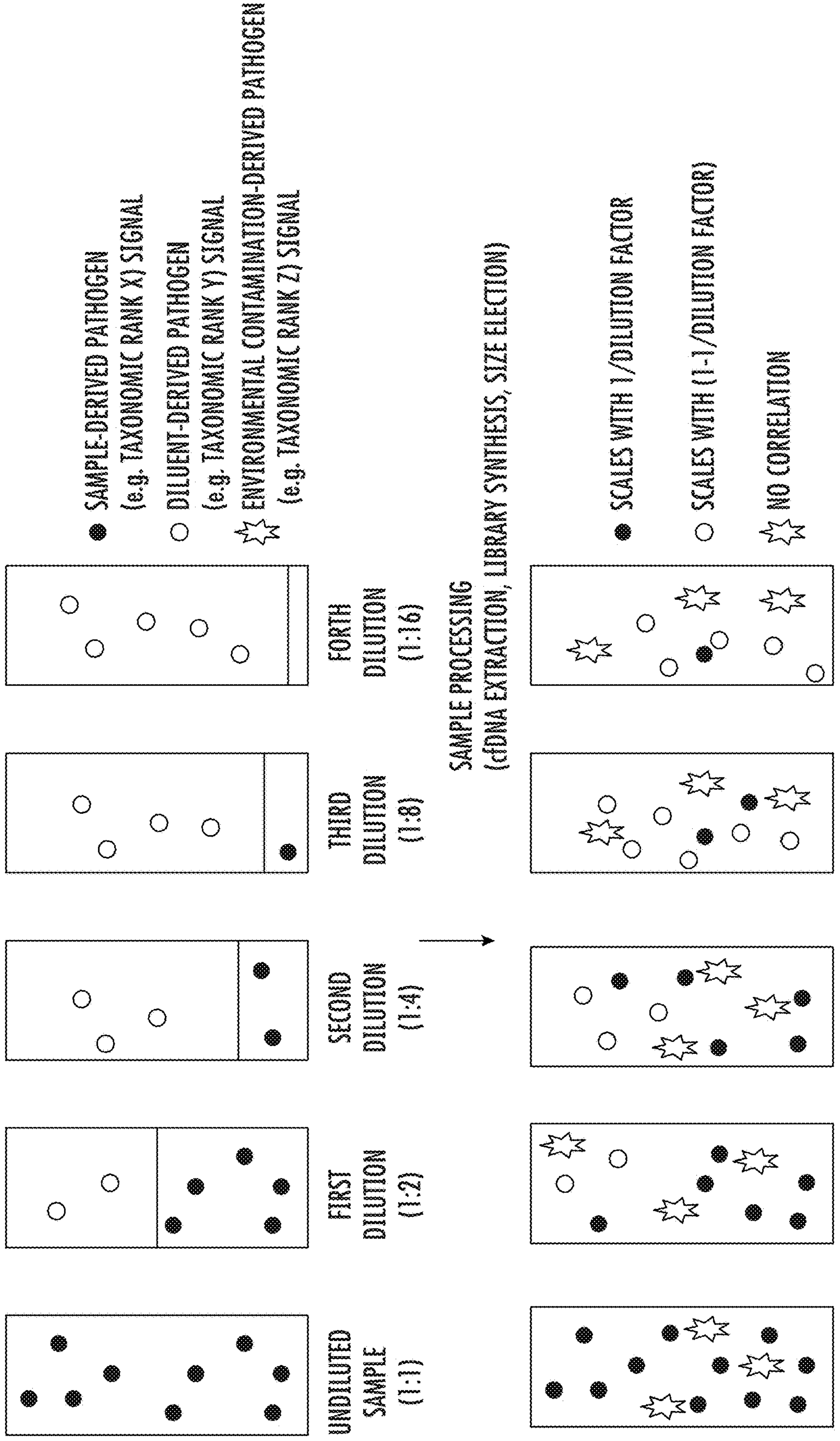
FIG. 4 (*a*) depicts a schematic of a dilution series subjected to sample processing and further analysis, where pathogen X is unique to the original sample.

FIG. 4*a* sets forth a basic schematic of an analysis of a sample containing a signal from a pathogen 'X' and various dilutions of the sample. Here, the sample is diluted into a first dilution (1:2, with dilution factor equal to 2), a second dilution (1:4, with dilution factor equal to 4), a third dilution (1:8, with dilution factor equal to 8), and a fourth dilution (1:16, with dilution factor equal to 16), but the number of dilutions and the dilution factors may vary in different instances. As shown in the top panel of FIG. 4*a*, the level of sample-derived pathogen 'X' signal (black circles) decreases as the sample is diluted. Conversely, if the diluent contains a different pathogen 'Y' (white circles), and the level of that pathogen signal rises with increasing dilution factor. The undiluted sample and its dilutions may then be subjected to sample processing. For example, if the sample is a cell-free plasma sample, cell-free DNA and/or cell-free RNA may be extracted from the sample and the members of the dilution series. The sample processing may include synthesis of a library from the undiluted sample and each dilution. In some examples, library synthesis may involve uniquely tagging or indexing each dilution so that it can be identified during a later analysis step. In some cases, the sample processing may include size-selection. The lower panel of FIG. 4*a* depicts possible outcomes of sample and the members of the dilution series processing. In one scenario, the pathogen signal scales with the inverse of the dilution factor ($d^{-1}$, where d is the dilution factor), or otherwise decreases with increasing dilutions. Such a result may indicate that the signal genuinely derived from the sample and is therefore a sample-derived pathogen signal. In another scenario, the pathogen signal scales with ($1-d^{-1}$), or otherwise increases with increasing dilutions. Such a result may indicate the signal is from a diluent-derived pathogen. And finally, when there is little or no correlation between dilution factor and pathogen signal, such result may indicate that the signal is from an environmental contaminant (heptagons).

Figure 4B:
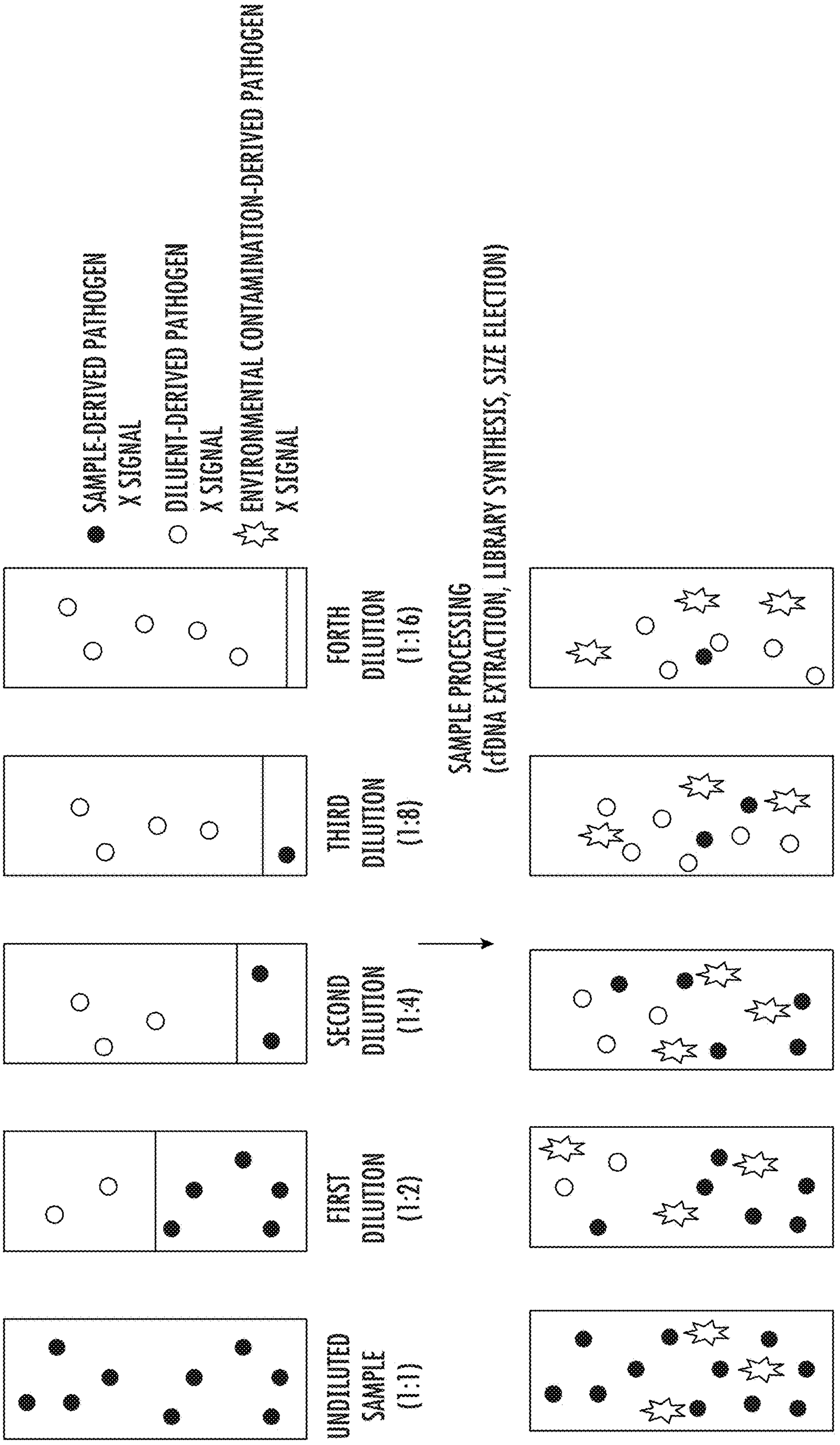

The same pathogen species can be present in the original sample, diluent and/or as environmental contaminant. FIG. 4*b* sets forth a schematic of an analysis of a sample containing a pathogen signal from pathogen 'X' (black circles) and various dilutions of the sample prepared with a diluent containing a pathogen signal from the same pathogen 'X' (white circles). In addition, the environmental contamination similarly contains the pathogen signal from the same pathogen 'X' (heptagons). Here, the sample is also diluted into a first dilution (1:2, with dilution factor equal to 2), a second dilution (1:4, with dilution factor equal to 4), a third dilution (1:8, with dilution factor equal to 8), and a fourth dilution (1:16, with dilution factor equal to 16), but the number of dilutions and the degree of dilution factors may vary in different instances. As shown in the top panel of FIG. 4*b*, the level of total pathogen 'X' signal (black circles and white circles) as the sample is diluted depends on the relative level of the pathogen 'X' signal in the original sample, and diluent. The undiluted sample and its dilutions may then be subjected to sample processing. For example, if the sample is a cell-free plasma sample, cell-free DNA and/or cell-free RNA may be extracted from the sample and the members of the dilution series. The sample processing may include synthesis of a library from the undiluted sample and each dilution. In some examples, library synthesis may involve uniquely tagging or indexing each dilution so that it can be identified during a later analysis step. In some cases, the sample processing may include size-selection. The lower panel of FIG. 4*b* depicts possible outcomes of sample and the members of the dilution series processing. The total signal for pathogen 'X' after processing across the dilution series described in the top panel of FIG. 4*b* may be described with an equation $C_{total}(d)=C_E+C_D+(1/d)*(C_S-C_D)$, where $C_{total}$, $C_E$, $C_D$, $C_S$, and d are total pathogen signal for pathogen 'X' after processing, contribution of the environmental contaminants to the total pathogen signal for pathogen 'X', the pathogen signal for pathogen 'X' in diluent, the pathogen signal for pathogen 'X' in the original sample, and dilution factor, respectively.

The total signal for a pathogen and its trends that may be identified across the dilution series can be affected among others by the differences in process efficiencies at different dilution factors, and differences in process efficiencies or recoveries between the synthetic nucleic acids added to the members of the dilution series as compared to the nucleic acids endogenous to the original sample, diluent and/or environmental contaminants. The signal and/or trends in the signal that may be identified across the dilution series for the nucleic acid classes unique to or predominately (e.g., more than 99%, more than 95%, more than 90%, more than 80%, more than 75%, more than 50% of the total signal for any particular class of nucleic acids, e.g. sequences or fragments of human nucleic acids in the original sample; an endogenous or spiked-in pathogen that is unique to or predominately originating from diluent and/or environmental contaminants etc.) originating from the original sample, diluent and/or environmental contaminants can be used to calibrate/assess/estimate/determine/isolate the effects of the differences in aforementioned process efficiencies. The calibrated/assessed/estimated/determined/isolated effects of the differences in aforementioned process efficiencies can be then used to obtain more accurate expectations for the total signal for a pathogen and more accurate trends in the total pathogen signal across the dilution series for all or a subset of pathogens.

As provided herein, myriad numbers of approaches can be used to dilute a sample, or otherwise change its mass, cell count, quantity, concentration or volume. Generally, a dilution factor can be the same across a dilution series. In other embodiments, a dilution factor can be different. A dilution factor can be equal to final volume divided by initial volume. Following dilution of a sample, an assay can be performed upon a sample and each dilution in a dilution series (e.g. a first dilution and a second dilution). In some embodiments, the assay can be a sequencing assay or an amplification assay. Following a sequencing or amplification assay, a quantity of a nucleic acid can be determined in a sample and any dilutions of that sample.

In some aspects, a dilution series or serial dilution can be used to determine whether a particular reagent (e.g., extraction reagent, PCR reagent) is contaminated. In such cases, a reagent is diluted into at least a first dilution (which could be undiluted) and a second dilution, which is more dilute than the first. A pathogen nucleic acid can then be identified as reagent-based contaminant when the quantity of the pathogen nucleic acid in the first dilution is greater than a quantity of that nucleic acid in the second dilution. Conversely, if the level of a pathogen nucleic acid remains the same over the dilutions or increases with increasing dilutions or is not correlated, then that is a sign that the nucleic acid is not a reagent contaminant. Other trends are possible as well as described above.

In some aspects, a nucleic acid is identified as a "target" nucleic acid, or a nucleic acid derived from a pathogen present in the initial sample, when the quantity of the nucleic acid decreases when a sample is diluted, either in a single dilution or in a series. In some aspects, a nucleic acid is identified as a "target" nucleic acid, or a nucleic acid derived from a pathogen present in the initial sample, when the quantity of the nucleic acid increases from a non-zero value in undiluted original sample when a sample is diluted, either in a single dilution or in a series. In some aspects, a nucleic acid is identified as an environmental contaminant when the quantity of a target nucleic acid is not correlated across dilutions of the sample, or when the level of nucleic acid increases with increasing dilutions, which may be indicative of contamination of the diluent. In some specific aspects, a nucleic acid is identified as an environmental contaminant when the quantity of a nucleic acid in a plurality of dilutions is relatively the same. In some cases, a nucleic acid is identified as originating from a diluent, when increased signal for that nucleic acid is detected in higher levels of dilution. See FIG. 4.

The terms "correlate" or "correlation" and equivalents as used herein can refer to a relationship that involves some type of dependence, where dependence refers to a relationship between two random variables or two sets of data. A correlation may be statistical if, upon analysis by statistical means or tests, the relationship is found to satisfy the threshold of significance of the statistical test used. Positively correlated variables or data will change in the same direction, whereas negatively correlated variables or data change in opposite directions. For example, a negative correlation between a diluent and a contaminant nucleic acid can be where an increase in quantity of diluent is associated with a decrease in a level, quantity or concentration of the contaminant nucleic acid. A negative correlation between a diluent and a contaminant nucleic acid can be where across a dilution series, a level, quantity or concentration of the contaminant nucleic acid is reduced in a second dilution relative to a first dilution and/or a level, quantity or concentration of the contaminant nucleic acid is reduced in a third dilution relative to the second dilution and/or the first dilution. A positive correlation between a diluent and a contaminant nucleic acid can be where the increase in quantity of diluent increases a level, quantity or concentration of the contaminant nucleic acid. A positive correlation between a diluent and a contaminant nucleic acid can be where across a dilution series, a level, quantity or concentration of the contaminant nucleic acid is increased in a second dilution relative to a first dilution and/or the level, quantity or concentration of the contaminant nucleic acid is increased in a third dilution relative to the second dilution and/or the first dilution.

Dilution can refer to the process of adding additional solvent, liquid, or buffer to a solution or a sample to decrease its concentration. This process can keep the amount of solute constant, but increases the total amount of solution, thereby decreasing its final concentration. Dilution can also refer to taking different quantities of a sample (such as progressively smaller or larger quantities) and mixing such quantities with a fixed or variable level of a diluent or no added diluent, solvent, liquid or buffer. Dilution can also be achieved by mixing a solution of higher concentration with an identical solution of lesser concentration. In some aspects, a solvent in regards to dilution can be a buffer, a positive control, a negative control, culture medium, or a sample. In some aspects, a solute in regards to dilution can be a target nucleic acid, a buffer, a positive control, a negative control, culture medium, or a sample. In some aspects, a solute in regard to dilution can be a target nucleic acid. In some aspects, dilution can refer to decreasing a final concentration of a target nucleic acid.

As used herein, the term "sample series" may refer to a serial dilution or dilution series, as described herein. The term "sample series" can also refer to any set of samples in which at least two of the members of the sample series have different quantities, masses, dilution factors, or concentrations of sample; the sample series may contain members that contain a diluent, or, in some cases, none of the members in the sample series contains a diluent. As will be appreciated by a person of skill in the art, the methods provided herein describing dilution series are equally applicable to most sample series. As such, when a dilution series is described herein, a sample series is also intended to be encompassed by the description.

The terms "serial dilution" or "dilution series" are used interchangeably herein. The terms refer to a dilution series generated in any manner. Dilution series can refer to the dilution of mass, volume, or a specific quantity, for example cell count. Therefore, to dilute a sample, the quantity of diluent to be added can be based on the mass, volume, or cell count of a sample. Further, a quantity or amount of diluent can refer to a mass, volume, or number of cells. In some instances, a dilution series or serial dilution can refer to a succession of step dilutions, (often, each with the same dilution factor), where the diluted material of the previous step is used to make the subsequent dilution. In other cases, each member of the dilution series is directly obtained from the undiluted sample. For example, the undiluted sample is used to make a two-fold dilution by adding an equal volume of diluent to an equal volume of the undiluted sample. In other instances, a four-fold dilution in the series can be produced by adding diluent directly to a portion of the undiluted sample in a 3:1 ratio (e.g., 3 μl of diluent added to 1 μl of sample yields a four-fold dilution). In still other instances, a dilution series can consist of a series of changes in quantity, based on the mass, volume, or number of cells of the sample.

In some instances a first dilution to a second dilution can be less or greater than about 1:1, 1:2, 1:3, 1:4, 1:5, 1:6, 1;7, 1:8, 1:9, 1:10, 1:11, 1:12, 1:13, 1:14, 1:15, 1:20, 1:130, 1:50, 1:100; or 1:1000. In some instances a first dilution to a second dilution can be less or greater than about 1000:1, 100:1, 50:1, 30:1, 20:1, 15:1, 14;1, 13:1, 12:1, 11:1, 10:1, 9:1, 8:1, 7:1, 6:1, 5:1, 4:1, 3:1, 2:1; or 1:1.

In some embodiments, a diluent used to dilute a sample or target nucleic acids described herein can be a reagent. In some embodiments a diluent used to dilute a sample or target nucleic acids described herein can be a buffer, medium such as growth media, a positive control, a negative control, culture medium, a sample, a synthetic molecule, or synthetic plasma. In some aspects, a buffer can be basic, acidic, neutral, or isotonic. A buffer can be a solution buffer that prevents a change in pH. A buffer can be an extraction buffer, a suspension buffer or a lysis buffer. A buffer can be phosphate-buffered saline (PBS). A buffer may comprise potassium chloride, sodium thioglycollate, dodecylamine, a sugar, fructose, glucose, mannitol, maltose, glycerol, alanine, arginine, histidine, lysine, proline, asparagine, aspartic acid, pheylalanine, inosine, insulin EDTA, NAOH, NaCl and/or Tris-HCl in any combination. In some embodiments a diluent used to dilute a sample or target nucleic acids described herein is pretreated to uniquely label the nucleic acids in the diluent before using to prepare members of the dilution series. In some embodiments all or a fraction of nucleic acids in the diluent are biotinylated. In some embodiments diluent-specific barcodes are attached to all or a fraction of nucleic acids in the diluent. In some embodiments diluent-specific barcodes are attached by the addition of nucleotides to the 3' and/or 5' terminus of all or a fraction of nucleic acids in the diluent. In some embodiments the diluent-specific barcodes attached to the nucleic acids sequences present originally in the diluent are sequenced which allows for determination of the contribution of $C_S$ to $C_{total}$ (see symbol definitions above) during analysis of the dilution series sequencing data.

In some aspects, a dilution series can comprise at least 1, 2, 3, 4, 5, 10, 20, 50, 100, 150, or 200 dilutions. In other aspects, a dilution series can comprise less than 3, 4, 5, 10, 20, 30, or 40 dilutions. In some aspects, a dilution series can comprise multiple replicates of each dilution of the dilution series.

In some aspects, a control or a negative control disclosed herein can be diluted, for example in a dilution series. In some cases, for example, a negative control can be diluted in a dilution series comprising a first negative control dilution and a second negative control dilution wherein the second negative control dilution is more dilute than the first negative control dilution. In some embodiments, a control can be diluted with another control.

Analytical Validation

In some cases, analytical validations of next generation sequencing (NGS)-based diagnostic tests for infectious diseases can use a set of clinical samples which comprises infected clinical samples as well as healthy controls. Infection status of a given clinical sample can be established usually by blood culture and/or any additional clinical information for the donor patient. However, clinical samples qualified as negative/healthy by blood culture can still contain pathogen signal in the cfDNA fraction since blood culture requires the presence of intact live pathogen cells/spores/viral particles. In some instances, negative/healthy clinical samples can be positive for a pathogen for reasons not related to the level of pathogen in the sample prior to collection from the subject. For example, a contaminant introduced during sample processing may cause a sample to read as positive for such contaminant. This can result in "artificial false positives" when deriving the infection status from cfDNA by NGS and leads to increase in the false positive rates for a NGS method being validated.

During analytical validation, one can analyze "false positive" clinical samples further after the initial sequencing run by running either (1) a dilution series of the original plasma sample (or other type of sample) or (2) sequence a set of multiple undiluted replicates at higher sequencing depth. In some cases, if the initially detected pathogen signal originates in patient's plasma sample, then the signal can decrease in (1) with the dilution factor while it can be constant or vary by an amount set by the process precision in (2). In some cases, if the initially detected pathogen signal originates in part in the patient's plasma sample then the signal can decrease or increase in (1) with the dilution factor while it can be constant or vary by an amount set by the process precision in (2). In some cases, if the initially detected pathogen signal derived from the environmental contamination during sample processing then experiment (1) may not result in pathogen signal that is correlated with the dilution factor.

Spike-in Synthetic Nucleic Acids

This disclosure also describes the use of single synthetic nucleic acids and sets of synthetic nucleic acids for use in a variety of applications, for example high-throughput or next generation sequencing assays, or as barcodes to identify a sample. In some cases, when used in the described methods, the spike-in synthetic nucleic acids may allow efficient normalization of nucleic acids (e.g., disease-specific nucleic acids, pathogen nucleic acids, reagent contaminants) across samples, e.g., independent of the individual from which it was derived, the pre-analytical sample handling conditions, the method of nucleic acid extraction, the nucleic acid manipulations with molecular biology tools and methods, the methods of nucleic acid purification, the method of amplification, the act of the measurement itself, the storage conditions, and the passage of time. In some cases, this disclosure provides pools or sets of synthetic nucleic acids having particular characteristics, such as high numbers of unique sequences. The sets of synthetic nucleic acids may be used to monitor diversity loss during the course of sample analysis, which can, in turn, be used to determine the abundance of starting nucleic acids. The synthetic nucleic acids provided herein may also be used to track samples, to monitor cross-contamination between samples, to track reagents, to track reagent lots, track an origin of a pathogen or contaminant, and numerous other applications. Often, the design, length, quantity, concentration, diversity level, and sequence of the synthetic nucleic acids may be tailored for a particular application. In some cases, spike-in synthetic nucleic acids include carrier synthetic nucleic acids (e.g., carrier synthetic nucleic acids). See PCT/US2017/024176, which is hereby incorporated by reference in its entirety. The spike-in synthetic nucleic acids can be a degenerate pool of nucleic acids, or pool of nucleic acids with a high degree of diversity.

In some embodiments, the species of synthetic nucleic acids can differ in length. For example, the collection of synthetic nucleic acid species may collectively span the observable range of lengths of certain target nucleic acids in a sample, or at least a portion of such observable range. For example, the species may collectively span the lengths of disease-specific or pathogen-specific nucleic acids in a sample, particularly a sample obtained from a subject that is infected by, or suspected of being infected by, a pathogen. In some cases, the lengths of disease-specific or pathogen-specific nucleic acids in a sample may be in the range from about 40 to about 100 base pairs.

The synthetic nucleic acids can vary in GC content. In some cases, a spike-in synthetic nucleic acid panel comprises nucleic acids with GC contents spanning the range of about 40-60% GC, about 45-65% GC, about 30-70% GC, about 25-75% GC, or about 20-80% GC. GC content can be varied to match the composition of the positive control or genome to which they are paired, for example 30% GC content, 35% GC content, 40% GC content, 45% GC content, 50% GC content, 55% GC content, 60% GC content, 65% GC content, or 70% GC content. Spike-in nucleic acids with lengths and GC contents picked from a set of values can be used. For example, a set of synthetic nucleic acids can be selected from two or more lengths and two or more GC contents. See U.S. Pat. No. 9,976,181 titled "Synthetic Nucleic Acid Spike-Ins".

The domain within a nucleic acids species within a collection of synthetic nucleic acids may be a synthetic nucleic acid identifying sequence that comprises a unique code (e.g. unique identifier or barcode) signifying that the nucleic acid is a spike-in as opposed to part of the original sample. Generally, the unique code can be a code not present in the original sample or in the pool of target nucleic acids. In other embodiments, a unique code may not be present in any reference genome.

In some cases, a domain within a nucleic acid species within a collection of synthetic nucleic acids may be a "diversity code" associated with the overall pool or collection of synthetic acids. The diversity code domain may be a unique code signifying the amount of diversity within the pool of synthetic nucleic acids. In such cases, every synthetic nucleic acid within the diversity pool may be coded with a sequence signifying the degree of diversity (e.g., $2^{16}$ unique sequences for a diversity code composed of 16 randomized sequence positions) of the pool.

In some cases, a domain within a nucleic acid species within a collection of synthetic nucleic acids may be a feature domain associated with one or features of the sample, or the reagent, depending on the applications. For example, the feature domain may comprise a sequence coded to signify a particular reagent; a particular reagent lot; or a particular sample (e.g., sample number, patient number, patient name, patient age, patient gender, patient race, location where sample was obtained from patient).

Synthetic or spike-in nucleic acids may be selected or designed to be compatible with a nucleic acid library. In some cases, synthetic nucleic acids or spike-ins can contain adapters, common sequences, random sequences, poly-(A) tails, blunt ends, phosphorylated ends, dephosphorylated ends, or ragged ends, or any combination thereof. In some cases, synthetic nucleic acids or spike-ins can be designed to mimic nucleic acids in a sample in one or more of these or other characteristics.

The synthetic nucleic acids provided herein (e.g., spike-in synthetic nucleic acids) may contain any type of nucleic acid or a combination of nucleic acid types. In some embodiments, a synthetic or spike-in nucleic acid can be DNA. In some cases, a synthetic or spike-in nucleic acid can be single-stranded DNA. In some cases, a synthetic or spike-in nucleic acid can be double-stranded DNA. In some cases, a synthetic or spike-in nucleic acid can be RNA. Synthetic nucleic acids may be or may comprise any synthetic nucleic acid or nucleic acid analogue. The synthetic nucleic acids may comprise a modified or altered phosphate backbone; modified pentose sugar (e.g., modified ribose or deoxyribose); modified ends (e.g. modified 5' and 3' ends) or a modified or altered nucleobase (e.g., modified adenine (A), cytosine (C), guanine (G), thymine (T), uracil (U)).

A synthetic or spike-in nucleic acid can refer to any molecule that is added to a sample and is not limited to molecules that are synthesized chemically, e.g., on a column. In some cases, a synthetic or spike-in nucleic acid can be synthesized, for example, by PCR amplification, in vitro transcription, or other template-based replications. In some cases, synthetic or spike-in nucleic acid is or comprises sheared or otherwise fragmented nucleic acids. The sheared or fragmented nucleic acids may comprise genomic nucleic acids such as human or pathogen genomic nucleic acids. In some cases, the synthetic nucleic acids contain no human nucleic acids. In some cases, the synthetic nucleic acids may contain no nucleic acids that can be found in nature. In some cases, the synthetic nucleic acids may contain no sample nucleic acids.

A spike-in nucleic acid or a target nucleic acid may be attached, ligated or conjugated to a different molecule such as a bead, a fluorophore, a polymer or an oligomer. Examples of fluorophores include but are not limited to a fluorescent protein, Green Fluorescent Protein (GFP), Red Fluorescent Protein (RFP), and Yellow Fluorescent Protein (YFP). A spike-in nucleic acid or a target nucleic acid can be associated with a protein (e.g., histone, nucleic acid binding protein, DNA-binding protein, RNA-binding protein) or any other biological molecule or structure (e.g. cell membranes, lipids etc.). In other cases, spike-in nucleic acid or target nucleic acid may not be associated with a protein.

Spike-in nucleic acids can have sequences that differ from sequences potentially found in a sample or host. In some cases, spike-in nucleic acid sequences can be naturally occurring. In some cases, spike-in nucleic acid sequences may not be naturally occurring. In some cases, spike-in nucleic acid sequences can be derived from a host. In some cases, spike-in nucleic acid sequences may not be derived from a host. In some cases, spike-in or synthetic nucleic acids are not capable of hybridizing (or are not complementary) to one or more target nucleic acids (e.g., pathogen nucleic acids, disease-specific nucleic acids) and/or to one or more sample nucleic acids.

The concentration of a spike-in nucleic acid in a sample can vary. Spike-ins can be added in a wide range of concentrations. In some cases, about or at least about 100, 200, 300, 400, 500, 600, 700, 800, 1000, 1500, 2000, 3000, 4000, 5000, 10000, 50000, 100000, 500000, 1 million, 5 million, 10 million, 20 million, 50 million, or more molecules of each spike-in nucleic acid are added to each mL of plasma or sample or reagent or dilution in a dilution series. In some cases, from about 10 million to about 1000 million molecules of each spike-in nucleic acid can be added to each mL of plasma or sample or reagent or dilution in a dilution series. In some cases, the synthetic nucleic acids are spiked in at equimolar concentrations. In other cases, the synthetic nucleic acids are spiked into the sample or reagent or dilution of a dilution series in different concentrations. In some embodiments, spike-in described herein can be added to the same amount (volume or mass) of plasma, sample, or reagent after dilution.

In some embodiments, the same spike-ins can be added into a first dilution. In some cases, the same spike-in can be added into a second dilution, a third dilution, and/or in each dilution of a dilution series. In some cases spike-ins in a first dilution can be different from spike-ins in a second dilution or a sample. In some cases, a spike-in identifier can be a barcode. In some embodiments, spike-ins in a first dilution can comprise the same barcode. In some embodiments, spike-ins in a second dilution can comprise the same barcode.

Universal Normalization of Nucleic Acid Measurements

Disclosed herein are sets of synthetic nucleic acids, that when used in the described methods, may allow efficient and improved normalization of the amounts of disease-specific nucleic acids, pathogen-specific nucleic acids, contaminant nucleic acids, or other target nucleic acids in a sample. The sets of spiked nucleic acids may contain several "species" of nucleic acids that differ in length, such that the collection of spiked nucleic acid species collectively spans the observable range of lengths in the pathogen nucleic acids, disease-specific nucleic acids, contaminant nucleic acids, or other target nucleic acids to be measured.

The spike-in synthetic nucleic acids may be used to normalize the sample in a number of different ways. Often, the normalization may be across samples or dilutions, independent of the subject from which the sample was derived, the pre-analytical sample handling conditions, the method of nucleic acid extraction, the nucleic acid manipulations with molecular biology tools and methods, the methods of nucleic acid purification, the act of the measurement itself, the storage conditions, and/or the passage of time.

In some embodiments, the spike-in nucleic acids may normalize across all samples or dilution and all methods of measuring disease-specific nucleic acids, pathogen-specific nucleic acids, contaminant nucleic acid or other target nucleic acids. In some cases, the spike-ins may be used to determine relative abundance of a pathogen nucleic acid (or disease-specific nucleic acid or target nucleic acid) in a sample compared to other pathogen nucleic acids.

Generally, the methods provided herein can involve spiking-in or introducing one or more sets of synthetic nucleic acids into a sample, reagent, or dilution in a serial dilution. This spike-in step may occur at any point of the entire method including early in the process, mid-way through, or towards the end. For example, the synthetic nucleic acids may be introduced at the time, or directly after, the sample is collected from the subject, prior to or during storage of the sample, prior to transfer of the sample, before/during/after sample dilution, before or during nucleic acid extraction, before or during library preparation, directly before the sequencing assay, directly before the amplification assay or any other step of the method. In some cases, the method may comprise spiking a biological sample early in the process with a known amount of unique nucleic acid molecules that are measured by the same method, but readily distinguished from pathogen-specific or disease-specific nucleic acids, or target nucleic acids or other sample nucleic acids. In some cases, the biological sample is spiked with the synthetic nucleic acids at a single step in the process, e.g., when the sample is collected from the subject, when the sample is obtained in order to conduct analysis, during sample storage, before or during nucleic acid extraction, before or during library preparation, before or during amplification, or directly before the sequencing assay. In other cases, the same or different spike-in synthetic nucleic acids are introduced at different steps of the process. For example, unique synthetic nucleic acids may be introduced early in the process, such as at sample collection, and a different set of unique synthetic nucleic acid may be introduced later in the process such as prior to or following extraction, purification, or library preparation. The spike-in step may also be repeated at different steps of the method using identical collections of spike-in nucleic acids, or collections that differ in some aspect.

In general, a known concentration (or concentrations) of species of synthetic nucleic acids may be spiked into each sample or dilution of a serial dilution. In many cases, the species of synthetic nucleic acids can be spiked in at equimolar concentration of each species. In some cases, the concentrations of the species of synthetic nucleic acids can be different.

As the sample or dilution is processed and ultimately measured, the relative abundance of the nucleic acid species may be altered due to the inherent biases of the sample handling, preparation, and measurement. After measurement, the efficiency of recovering nucleic acids of each length can be determined by comparing the measured abundance of each "species" of spiked nucleic acid to the amount spiked in originally. This can yield a "length-based recovery profile".

The "length-based recovery profile" may be used to normalize the abundance of all (or most, or some) disease-specific nucleic acids, pathogen nucleic acids, or other target nucleic acids by normalizing the disease-specific nucleic acid abundances (or the abundances of the pathogen nucleic acids or other target nucleic acids) to the spiked molecule of the closest length, or to a function fitted to the spiked molecules of different lengths. This process may be applied to the disease-specific nucleic acids, and may result in an estimate of the "original length distribution of all disease-specific nucleic acids" at the time of spiking the sample. Similarly, this process may be applied to other target nucleic acids such as the pathogen-specific nucleic acids, and may result in an estimate of the "original length distribution of all pathogen-specific nucleic acids" at the time of spiking the sample. The "original length distribution of all target nucleic acids" may show the length distribution profile for the target nucleic acids (e.g., disease-specific nucleic acids, pathogen-specific nucleic acids) at the time of spiking the sample. It is this length distribution that the spiked nucleic acids can seek to recapitulate in order to achieve perfect or near-perfect abundance normalization.

As it may not be possible to spike a sample with a mixture of known nucleic acids that exactly recapitulates the relative abundance profile of disease-specific nucleic acids, pathogen nucleic acids, or other target nucleic acids in that specific sample, in part because the sample may have been used up or time may have changed the relative abundance profile, each "species" of spike-in can be weighted in proportion to its relative abundance within the "original length distribution of all disease-specific nucleic acids". The sum of all "weighting factors" can equal 1.0.

Normalization can involve a single step or a series of steps. In some cases, the abundance of disease-specific nucleic acids (or pathogen nucleic acids or other target nucleic acids) may be normalized using the raw measurement of the closest sized spiked nucleic acid abundance to yield the "Normalized disease-specific nucleic acid (or pathogen nucleic acids or other target nucleic acid) abundance". Then, the "Normalized disease-specific nucleic acid abundance" (or pathogen nucleic acids or other target nucleic acid abundance) may be multiplied by the "weighting factor" to adjust for the relative importance of recovering that length, yielding the "Weighted normalized disease-specific (or pathogen-specific or other target) nucleic acid abundance". One advantage of this method of normalization may be that it allows comparable measurements of target nucleic acid (e.g., disease-specific nucleic acid, pathogen nucleic acid) abundance across all (or most) methods of measuring disease-specific nucleic acid abundance, regardless of method.

The measurement of target nucleic acid abundance, or relative abundance may be especially useful for detection, prediction, monitoring, determination of target nucleic acid origin and diagnostic assays. Such assays may involve measuring the amount of target nucleic acids (e.g., disease-specific nucleic acids) in biological samples (e.g., plasma) to detect the presence of a pathogen or identify disease states or to determine if a target nucleic acid is sample based, reagent based, or environmental based. The methods described herein can make these measurements comparable across samples, times of measurement, methods of nucleic acid extraction, methods of nucleic acid manipulation, methods of nucleic acid measurement, and/or a variety of sample handling conditions.

Calculation of "Genome Copies Per Volume"

The methods and synthetic nucleic acids provided herein may be used to assist with certain calculations, including determining genome copies of a microbe or pathogen or number of nucleic acid fragments derived from a microbe or pathogen per volume unit of a sample from next generation sequencing results. In general, genome copies per volume may refer to an absolute measure of the amount of target nucleic acid (e.g., target nucleic acids derived from a specific pathogen) per 1 ml of fluid (e.g., plasma, urine, buffer, etc.) and may often be used as an expression to indicate the abundances, or relative abundance, of individual pathogens. The total number of reads and/or the magnitudes of the pathogen abundances may vary from sample to sample or dilution to dilution. It can be desirable to report a value that corresponds to the biological level of the infection and that can be useful for sample-to-sample comparisons or dilution to dilution (first dilution to a second dilution) comparisons.

In particular examples, the methods may be used to determine genome copies of pathogen nucleic acids per volume of sample, or of a dilution (e.g. first dilution or second dilution) especially a sample obtained from a subject infected by a pathogen, or suspected of being infected by a pathogen. The genome copies per volume may be determined or estimated using a statistical framework. The statistical framework can be used to estimate what the relative abundances are of one or more genomes that give rise to a collection of non-human reads (e.g., pathogen reads) in the sequencing results from a sample.

Using the spike-in synthetic nucleic acids provided herein, an estimate can be computed of the number of "genome copies per volume" of one or more pathogens/organisms in the sample. Generally, nucleic acids of various lengths may be spiked into the sample at known concentrations. In some cases, the fraction of information from the sample that is actually observed in the sequencing data can be observed for each spike-in length (e.g., by comparing observed reads with reads associated with the spiked nucleic acids, or by dividing the observed reads by the spike reads). The original numbers of non-host or pathogen molecules at each length can be back-calculated as well (e.g., inferred in part from the number of spike-in reads at each length). When the genome length of each pathogen is known, this load can be converted into a "genome copies per volume" measure.

In many cases, the methods for detecting genome copies per volume (as well as other methods provided herein) may involve removal or sequestration of low-quality reads. Removal of low-quality reads may improve the accuracy and reliability of the methods provided herein. In some cases, the method may comprise removal or sequestration of (in any combination): un-mappable reads, reads resulting from PCR duplicates, low-quality reads, adapter dimer reads, sequencing adapter reads, non-unique mapped reads, and/or reads mapping to an uninformative sequence.

In some cases, the sequence reads can be mapped to a reference genome, and the reads not mapped to such reference genome can be mapped to the target or pathogen genome or genomes. The reads, in some instances, may be mapped to a human reference genome (e.g., hg19), while remaining reads are mapped to a curated reference database of viral, bacterial, fungal, and other eukaryotic pathogens (e.g., fungi, protozoa, parasites).

In some particular examples, the method may comprise spiking a sample (e.g., plasma sample) and/or diluted samples in a dilution series with a known concentration of synthetic nucleic acids (e.g., DNA) prior to DNA extraction (e.g., cell-free DNA extraction, cell-free RNA extraction) or at a different stage of the assay (e.g., after extraction, before library preparation, before sequencing, during storage of the sample). The synthetic nucleic acids may also be added to negative and/or positive control samples. The control samples may, in some cases, be processed alongside the sample. The method may further comprise producing sequencing libraries for the samples (e.g., plasma sample, positive control, negative control). The libraries may be multiplexed and sequenced on a sequencing device known in the art, particularly a device capable of next generation sequencing. The method may further comprise discarding low quality reads and removing human reads by aligning to a human reference sequence (e.g., hg19). Remaining reads may be then aligned to a database of pathogen sequences. In some cases, reads corresponding to target sequences of interest (e.g., pathogen sequences) are quantified from NGS read sets. From this information, relative abundance of target nucleic acids (e.g., pathogen nucleic acids) may be expressed as genome copies per volume. The genome copies per volume value may be determined by, for example, determining the number of sequences present for each organism (e.g., pathogen) normalized to the known quantity of oligonucleotides spiked into the sample (e.g., plasma). The calculation of the genomes per volume may also take into account the relative length of the individual pathogen genome. In some cases, the genome copies per volume value may be determined by quantifying the number of sequences present for each organism (e.g., pathogen), normalizing to the known quantity of synthetic nucleic acids spiked into the sample, wherein the normalization of a pathogen sequence takes into account the synthetic nucleic acid that is closest in length to the pathogen sequence. Similarly, the normalization may involve use of a collection of spike-in synthetic nucleic acids of different lengths (e.g., 2, 3, 4, 5, 6, 10, 15, 20 or more different lengths), wherein the pathogen nucleic acids are normalized in relation to the respective closest-in-length spike-in nucleic acid within the collection of spike-ins.

Indexed Sample Series

In some embodiments, the method involves indexing or otherwise identifying members of a sample series or dilution series. Generally, the method involves introducing unique tags to each sample or dilution in the sample series or dilution series. The unique tags may have different nucleic acid sequences; and, generally, the tags are dilution-specific tags or sample-series-specific tags, although they may contain additional sequences that are not necessarily dilution-specific or sample-series specific. In other cases, the unique tags are otherwise configured to identify the sample and/or dilutions. In some cases, the methods provided herein include preparing a sequencing library from each member of the dilution series or sample series. The methods may further involve performing a sequencing assay on the sequencing libraries.

Figure 5:
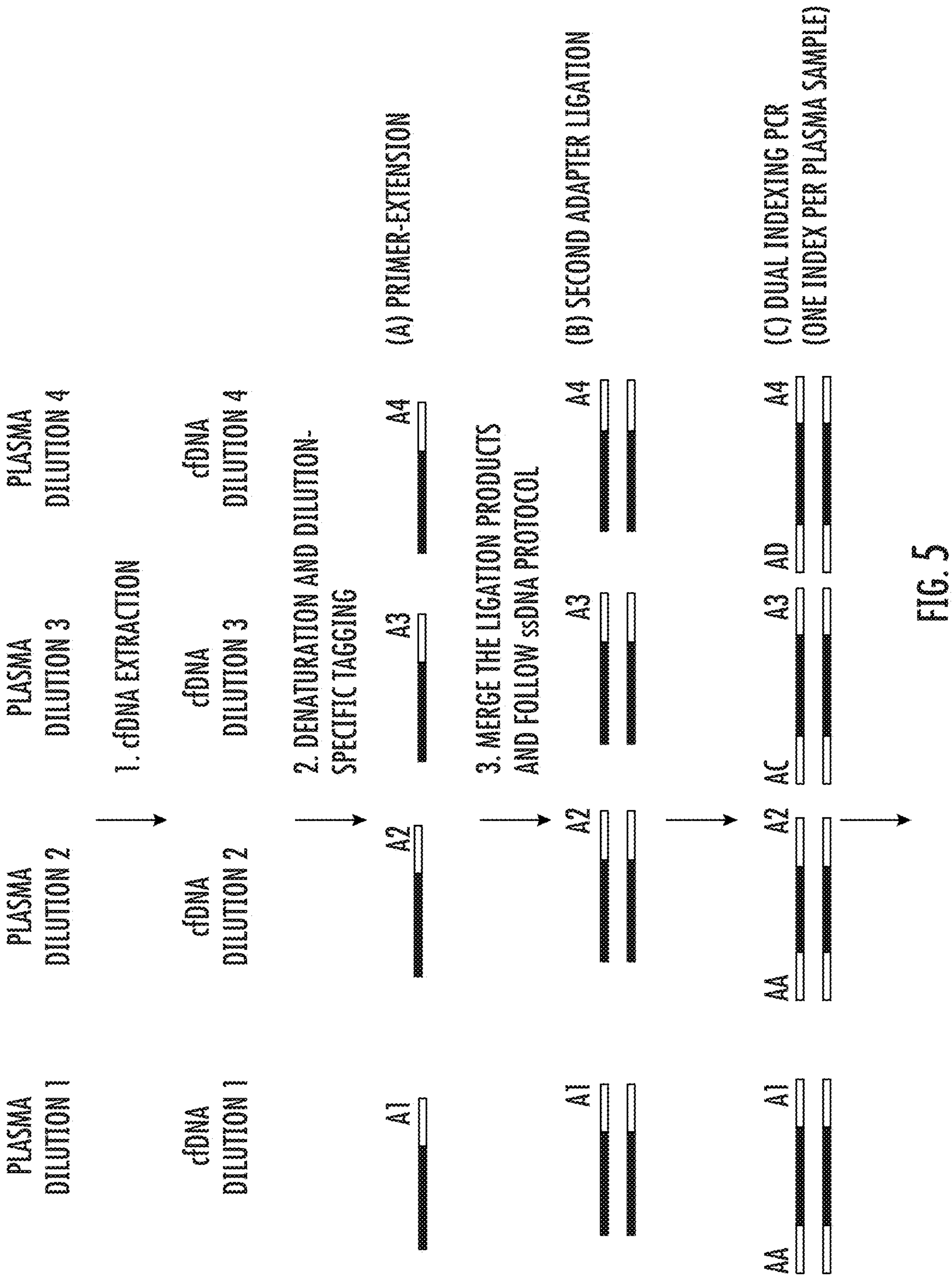
FIG. 5 depicts sample processing of a dilution series using dilution-specific tags.

FIG. 5 depicts an exemplary dilution series of a sample, in this case, a plasma sample. Dilution-specific tags or indexes may be added to each dilution of the sample including optionally, the undiluted sample. In cases where a serial dilution is performed directly on a biological sample (e.g., plasma), the dilution-specific tags may be added to each dilution of the biological sample. The dilutions are then subjected to sample processing, either pooled or individually. For example, each dilution may undergo an extraction step in which nucleic acids (e.g., cfDNA) are extracted from each dilution. In this example, the dilution-specific tags may be added to the original dilution series prepared directly from the sample; or, the dilution-specific tags may be added to each member of the dilution series containing the extracted sample (e.g., cfDNA). In a different embodiment, a sample (e.g., undiluted sample) may undergo a form of sample processing; for example, cfDNA may be extracted from the sample. In such cases, a dilution series may be generated from that cfDNA sample; and then the dilution-specific tags may then be added to each member of the cfDNA dilution series.

In some embodiments, each member of the dilution series undergoes additional sample processing such as nucleic acid extraction and then the result of the sample processing (e.g., extracted nucleic acids) is, in turn, used to prepare a dilution series. FIG. 5 illustrates an example in which a plasma sample is diluted into a dilution series, each member of the dilution series is subjected to a cfDNA extraction step, and then the dilution-specific tags are added to the dilution series containing extracted nucleic acids (e.g., cfDNA). Thus, in some cases, the dilution-specific tags can be added to different dilutions in a series containing nucleic acids extracted from the sample. As shown in FIG. 5, each tag is able to uniquely identify the particular sample or member of the dilution series (e.g., Dilution 1, Dilution 2, etc.). In some cases, the tags are added to the dilutions at a different stage in the process. For example, the tags may be added to the original sample (plasma), as described above. Or, in some cases, the dilution-specific tags may be added after a dilution series is prepared from a different type of sample (e.g., extracted nucleic acids, purified nucleic acids, etc.).

In some cases, the tags are attached or ligated to single-stranded nucleic acids. In such cases, the tagging or attachment may occur after a sample (e.g., dsDNA) is denatured in order to produce single-stranded nucleic acids. In other cases, such tagging is made directly to the single-stranded nucleic acids present in the sample. For example, tags can be attached to a single-stranded nucleic acid molecule by using a primer extension procedure. In this case, the 3' end of the primer can be degenerate for binding non-specifically to the single-stranded nucleic acid molecule. The 5' end of the primer can include tag sequences along with additional sequences, such as sequencing primer binding sites, primer binding sites, etc. In some cases, the tags are attached or ligated to double-stranded nucleic acids.

Generally, the tags are used to uniquely identify each member of a dilution series. However, in some cases, the tags may also contain additional sequences such as sequences containing primer binding sites or sample indexes.

The dilution-specific sequences can be used to identify each of the nucleic acid (e.g., cfDNA) dilution members. As such, after dilution-specific tag attachment and/or adapter ligation, the dilution samples can be pooled into one sample. Alternatively, the nucleic acid dilution samples can be separately processed.

The nucleic acid samples can be processed separately to further attach second adapters to one or both ends of the nucleic acids (e.g., cfDNA). (In other instances, second adapters are already included in the dilution-specific tags). In some cases, the second adapters can have an index sequence that also identifies the sample or dilution member. For example, as shown in FIG. 5, the cfDNA dilution 1 can be attached with an adapter sequence, AA. Similarly, the cfDNA Dilution 2 can have an adapter sequence AB, the cfDNA Dilution 3 can have an adapter sequence AC, and the cfDNA Dilution 4 can have an adapter sequence AD. The second adapter may have a second sequence designed to identify the particular sample in order to distinguish it from other samples possibly processed at the same time. For example, the second adapter may identify a patient. The second adapter may be added to either end of the tagged nucleic acids, or to both ends of the tagged nucleic acids. In some cases, the second adapter is pre-ligated to the dilution-specific tags.

In some cases, a pre-ligation step is introduced to introduce specific dilution index sequences to the ends of the nucleic acids prior to (second) adapter ligation. The dilution index sequence can be dilution-specific for each sample. In some other cases, the introduction of an adapter sequence or another index sequence follows the introduction of the dilution index sequence. In such cases, successful ligation may depend on successful pre-attachment (e.g., ligation) of the dilution index sequence. In other embodiments, the introduction of an adapter sequence or another index sequence following the introduction of the dilution index sequence may not be dependent on successful pre-attachment (ligation) of the dilution index sequence.

Figure 8:
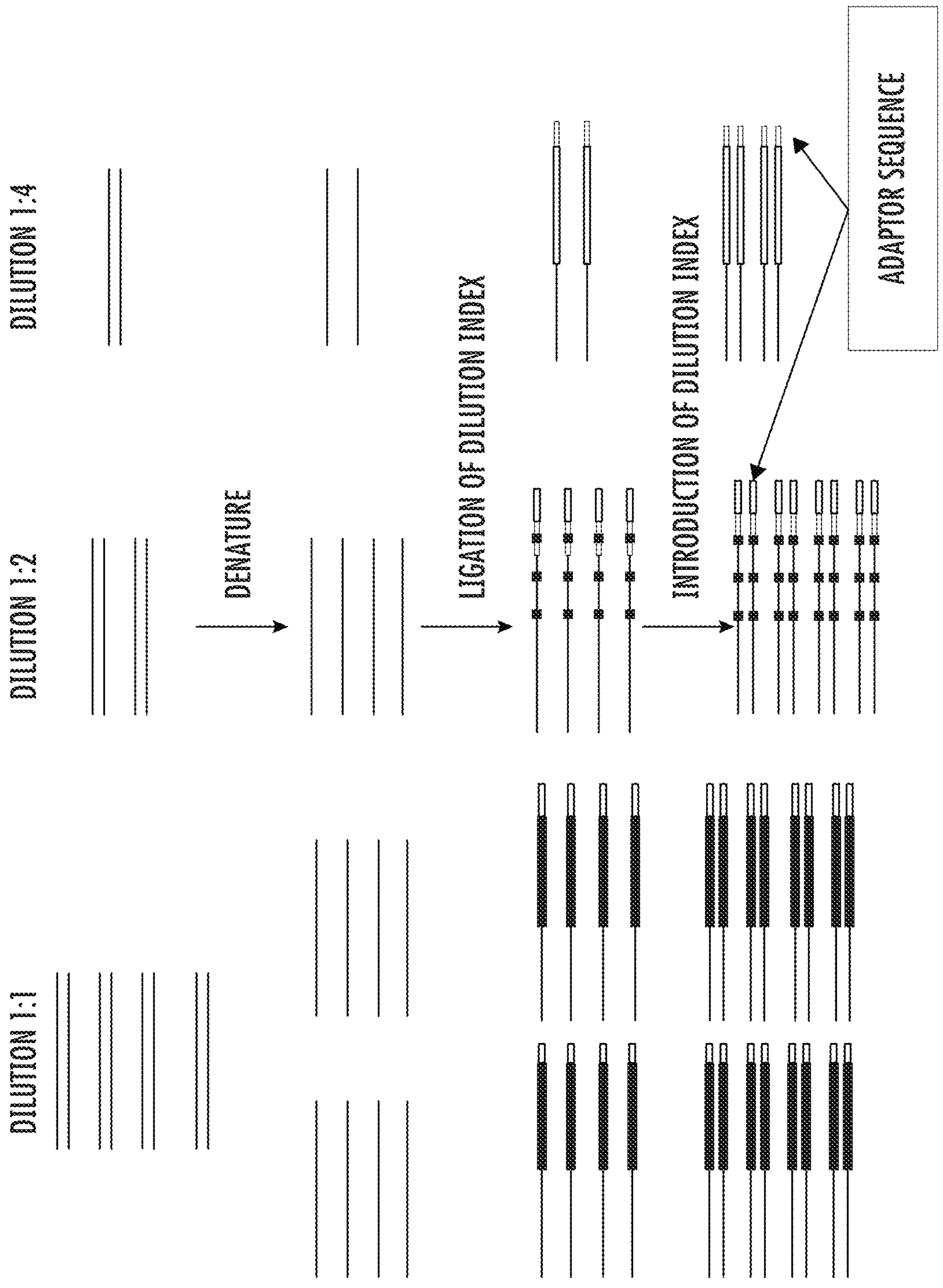
FIG. 8 depicts sample processing of a dilution series using dilution-specific tags prior to ligation of adapter sequences.

FIG. 8 provides an additional illustration of ligation (or attachment) of the dilution-specific tags. FIG. 8 depicts a sample that is initially double-stranded and is then denatured prior to attachment of the dilution-specific tag. (In some cases, however, the dilution-specific tags may be attached to the double-stranded nucleic acids.) In this case, the unique dilution-specific tags are unique to the following dilutions: Dilution 1:1, Dilution 1:2 and Dilution 1:4. In some cases, in addition to the unique sequences, the dilution-specific tags also contain a common sequence, such as a patient identifier or other form of sample identifier. As depicted in FIG. 8, an adaptor sequence or index sequence with the same sequence can be attached to a dilution index sequence in each dilution (1:1, 1:2 and 1:4). Further, additional adaptor sequences or index sequence may be attached to a dilution index sequence and may or may not be unique to each dilution.

Barcodes

Unique sample identifiers or barcodes can be completely scrambled (e.g., randomers of A, C, G, and T for DNA or A, C, G, and U for RNA) or they can have some regions of shared sequence. For example, a shared region on each end may reduce sequence biases in ligation events. In some cases, a shared region can be about or at least about 1, 2, 3, 4, 5, 6, 7, 8, 9, 10, 15, or 20 common base pairs. Combinations of barcodes can be added to increase diversity. For example, barcodes can be used as identifiers for well position in a microtiter plate (e.g., 96 different barcodes for a 96-well plate), and another barcode can be used as an identifier for a plate number (e.g., 24 different barcodes for 24 different plates), giving 96×24=2,304 combinations using 96+24=120 sequences. Using 3 or more barcodes per sample can increase the achievable diversity even more dramatically. Spike-ins as described herein can comprise barcodes. In some cases, barcodes can comprise spike-ins. In some cases, spike-ins can be barcodes. In some cases, barcodes may be about or at least about 2, 3, 4, 5, 6, 7, 8, 9, 10, 15, 20, 30, 40, 50, 60, 70, 80, 90, 100, 110, 120, 130, 140, 150, 160, 170, 200, 250, 300, 350, or 400, 500, or 1000 nucleotides (or base pairs) in length. In some cases, target nucleic acids may be up to about 3, 4, 5, 6, 7, 8, 9, 10, 15, 20, 30, 40, 50, 60, 70, 80, 90, 100, 110, 120, 130, 140, 150, 160, 170, 180, 190, 200, 250, 300, 350, 400, 500, or 1000 nucleotides (or base pairs) in length.

Nucleic Acid Enrichment and Library Preparation

In the methods provided herein, nucleic acids can be isolated from a sample using any means known in the art. For example, nucleic acids can be extracted using liquid extraction (e.g., Trizol, DNAzol) techniques. Nucleic acids can also be extracted using commercially available kits (e.g., QIAamp Circulating Nucleic Acid Kit, Qiagen DNeasy kit, QIAamp kit, Qiagen Midi kit, QIAprep spin kit). Nucleic acids described herein can be target nucleic acids.

Nucleic acids can be concentrated or precipitated by known methods, including, by way of example only, centrifugation. Nucleic acids can be bound to a selective membrane (e.g., silica) for the purposes of purification. Nucleic acids can also be enriched for fragments of a desired length, e.g., fragments which are less than 1000, 500, 400, 300, 200 or 100 base pairs in length. Such an enrichment based on size can be performed using, e.g., PEG-induced precipitation, an electrophoretic gel or chromatography material (Huber et al. (1993) Nucleic Acids Res. 21:1061-6), gel filtration chromatography, or TSKgel (Kato et al. (1984) J. Biochem, 95:83-86), which publications are hereby incorporated by reference in their entireties for all purposes.

A nucleic acid sample can be enriched for target polynucleotides (e.g. target nucleic acids), particularly target nucleic acids associated with inflammation or infection or contamination. In some cases, target nucleic acids can be pathogen nucleic acids (e.g., cell-free pathogen nucleic acids). In some cases, target nucleic acids can be cell-free RNA associated with a particular organ or tissue including but not limited to uterus, heart, lung, kidney, fetal brain, liver, or cervical tissue.

Target enrichment can be by any means known in the art. For example, the nucleic acid sample may be enriched by amplifying target sequences using target-specific primers (e.g., primers specific for pathogen nucleic acids). The target amplification can occur in a digital PCR format, using any methods or systems known in the art. The nucleic acid sample may be enriched by capture of target sequences onto an array immobilized thereon target-selective oligonucleotides. The nucleic acid sample may be enriched by hybridizing to target-selective oligonucleotides free in solution or on a solid support. The oligonucleotides may comprise a capture moiety which enables capture by a capture reagent. In some embodiments, the nucleic acid sample is not enriched for target polynucleotides, e.g., represents a whole genome.

In some cases, target (e.g., pathogen, organ, contaminant) nucleic acids can be enriched relative to background (e.g., subject, healthy tissue) nucleic acids in the sample, for example, by pull-down (e.g., preferentially pulling down target nucleic acids in a pull-down assay by hybridizing them to complementary oligonucleotides conjugated to a label such as a biotin tag and using, for example, avidin or streptavidin attached to a solid support), targeted PCR, or other methods. Examples of enrichment techniques include, but are not limited to: (a) self-hybridization techniques in which the major population in a sample of nucleic acids self-hybridizes more rapidly than the minor population in the sample; (b) depletion of nucleosome-associated DNA from free DNA; (c) removing and/or isolating DNA of specific length intervals; (d) exosome depletion or enrichment; and (e) strategic capture of regions of interest.

In some cases, a nucleic acid library can be prepared. The nucleic acid library can be a single-stranded nucleic acid library or a double-stranded nucleic acid library. In some cases, a single-stranded nucleic acid library can be a single-stranded DNA library (ssDNA library) or an RNA library. In some cases, a double-stranded nucleic acid library can be a double-stranded DNA library (dsDNA library). A method of preparing an ssDNA library can comprise denaturing a double stranded DNA fragment into ssDNA fragments, ligating a primer docking sequence onto one end of the ssDNA fragment, and hybridizing a primer to the primer docking sequence. The primer can comprise at least a portion of an adaptor sequence that couples to a next-generation sequencing platform. The method can further comprise extension of the hybridized primer to create a duplex, wherein the duplex can comprise the original ssDNA fragment and an extended primer strand. The extended primer strand can be separated from the original ssDNA fragment. The extended primer strand can be collected, wherein the extended primer strand can be a member of the ssDNA library. A method of preparing an RNA library can comprise ligating a primer docking sequence onto one end of the RNA fragment and hybridizing a primer to the primer docking sequence. The primer can comprise at least a portion of an adaptor sequence that couples to a next-generation sequencing platform. The method can further comprise extension of the hybridized primer to create a duplex, wherein the duplex comprises the original RNA fragment and an extended primer strand. The extended primer strand can be separated from the original RNA fragment. The extended primer strand can be collected, wherein the extended primer strand is a member of the RNA library. A method of preparing a dsDNA library can comprise ligating an adaptor sequence onto one or both ends of the dsDNA fragment.

In various aspects, dsDNA can be fragmented by any means known in the art or as described herein. In some cases, dsDNA can be fragmented by physical means (e.g., by mechanical shearing, nebulization, or sonication), by enzymatic means, or by chemical means.

In some embodiments, cDNA can be generated from RNA. For example, cDNA may be generated using random primed reverse transcription (RNaseH+) to generate randomly sized cDNA.

The lengths of the nucleic acids may vary. The nucleic acids or nucleic acid fragments (e.g., dsDNA fragments, RNA, or randomly sized cDNA) can be less than 1000 bp, less than 500 bp, less than 200 bp, or less than 100 bp. The DNA fragments can be about 40 to about 100 bp, about 50 to about 125 bp, about 100 to about 200 bp, about 150 to about 400 bp, about 300 to about 500 bp, about 100 to about 500, about 400 to about 700 bp, about 500 to about 800 bp, about 700 to about 900 bp, about 800 to about 1000 bp, or about 100 to about 1000 bp. In some cases, the nucleic acids or nucleic acid fragments (e.g., dsDNA fragments, RNA, or randomly sized cDNA) can be within the range from about 20 to about 200 bp, such as within the range from about 40 to about 100 bp.

The ends of dsDNA fragments can be polished (e.g., blunt-ended). The ends of DNA fragments can be polished by treatment with a polymerase. Polishing can involve removal of 3' overhangs, fill-in of 5' overhangs, or a combination thereof. The polymerase can be a proof-reading polymerase (e.g., comprising 3' to 5' exonuclease activity). The proofreading polymerase can be, e.g., a T4 DNA polymerase, Pol 1 Klenow fragment, or Pfu polymerase. Polishing can comprise removal of damaged nucleotides (e.g., abasic sites), using any means known in the art.

Sequencing

This disclosure provides methods of analyzing nucleic acids. Such analytical methods may include sequencing the nucleic acids as well as bioinformatic analysis of the sequencing results. The nucleic acids produced according the present methods may be analyzed to obtain various types of information including genomic, epigenetic (e.g., methylation), and RNA expression. Methylation analysis can be performed by, for example, conversion of methylated bases followed by DNA sequencing. RNA expression analysis can be performed by, for example, polynucleotide array hybridization, RNA sequencing techniques, or sequencing cDNA produced from RNA.

In some embodiments, sequencing can be performed using a next generation sequencing assay. As used herein, the term "next generation" is well-understood in the art and generally refers to any high-throughput sequencing approach including, but not limited to one or more of the following: massively-parallel signature sequencing, pyrosequencing (e.g., using a Roche 454 sequencing device), Illumina (Solexa) sequencing, sequencing by synthesis (Illumina), Ion torrent sequencing, sequencing by ligation (e.g., SOLiD sequencing), single molecule real-time (SMRT) sequencing (e.g., Pacific Bioscience), polony sequencing, DNA nanoball sequencing, heliscope single molecule sequencing (Helicos Biosciences), and nanopore sequencing (e.g., Oxford Nanopore). In some cases, the sequencing assay uses nanopore sequencing. In some cases, the sequencing assay includes some form of Sanger sequencing. In some cases, the sequencing involves shotgun sequencing; in some cases, the sequencing includes bridge PCR. In some cases, the sequencing is broad spectrum. In some cases, the sequencing is targeted.

In some cases, the sequencing assay can comprise a Gilbert's sequencing method. In such approach, nucleic acids (e.g., DNA) are chemically modified and then cleaved at specific bases. In some cases, a sequencing assay comprises dideoxynucleotide chain termination or Sanger-sequencing.

A sequencing-by-synthesis approach may be used in the methods provided herein. In some cases, fluorescently-labeled reversible-terminator nucleotides are introduced to clonally-amplified DNA templates immobilized on the surface of a glass flowcell. During each sequencing cycle, a single labeled deoxynucleoside triphosphate (dNTP) may be added to the nucleic acid chain. The labeled terminator nucleotide may be imaged when added in order to identify the base and may then be enzymatically cleaved to allow incorporation of the next nucleotide. Since all four reversible terminator-bound dNTPs (A, C, T, G) are generally present as single, separate molecules, natural competition may minimize incorporation bias.

In some cases, a method called Single-molecule real-time (SMRT) can be used. In such approach, nucleic acids (e.g., DNA) are synthesized in zero-mode wave-guides (ZMWs), which are small well-like containers with capturing tools located at the bottom of the well. The sequencing is performed with use of unmodified polymerase (attached to the ZMW bottom) and fluorescently labelled nucleotides flowing freely in the solution. The fluorescent label is detached from the nucleotide upon its incorporation into the DNA strand, leaving an unmodified DNA strand. A detector such as a camera may then be used to detect the light emissions; and the data may be analyzed bioinformatically to obtain sequence information.

In some cases, sequencing by ligation approach can be used to sequence the nucleic acids in a sample. One example is the next generation sequencing method of SOLiD (Sequencing by Oligonucleotide Ligation and Detection) sequencing (Life Technologies). This next generation technology may generate hundreds of millions to billions of small sequence reads at one time. The sequencing method may comprise preparing a library of DNA fragments from the sample to be sequenced. In some cases, the library is used to prepare clonal bead populations in which one species of fragment is present on the surface of each bead (e.g., magnetic bead). The fragments attached to the magnetic beads may have a universal adapter sequence attached so that the starting sequence of every fragment is both known and identical. In some cases, the method may further involve PCR or emulsion PCR. For example, the emulsion PCR may involve the use of microreactors containing reagents for PCR. The resulting PCR products attached to the beads may then be covalently bound to a glass slide. A sequencing assay such as a SOLiD sequencing assay or other sequencing by ligation assay may include a step involving the use of primers. Primers may hybridize to the universal adapter sequence or other sequence within the library template. The method may further involve introducing four fluorescently labelled di-base probes that compete for ligation to the sequencing primer. Specificity of the di-base probe may be achieved by interrogating every first and second base in each ligation reaction. Multiple cycles of ligation, detection and cleavage may be performed with the number of cycles determining the eventual read length. In some cases, following a series of ligation cycles, the extension product is removed and the template is reset with a primer complementary to the n−1 position for a second round of ligation cycles. Multiple rounds (e.g., 5 rounds) of primer reset may be completed for each sequence tag. Through the primer reset process, each base may be interrogated in two independent ligation reactions by two different primers. For example, the base at read position 5 may be assayed by primer number 2 in ligation cycle 2 and by primer number 3 in ligation cycle 1.

In any of the embodiments, the detection or quantification analysis of the oligonucleotides can be accomplished by sequencing. The subunits or entire synthesized oligonucleotides can be detected via full sequencing of all oligonucleotides by any suitable methods known in the art, e.g., Illumina HiSeq 2500, including the sequencing methods described herein.

Sequencing can be accomplished through classic Sanger sequencing methods which are well known in the art. Sequencing can also be accomplished using high-throughput systems some of which allow detection of a sequenced nucleotide immediately after or upon its incorporation into a growing strand, e.g., detection of sequence in real time or substantially real time. In some cases, high throughput sequencing generates at least 1,000, at least 5,000, at least 10,000, at least 20,000, at least 30,000, at least 40,000, at least 50,000, at least 100,000, or at least 500,000 sequence reads per hour. In some cases, each read is at least 50, at least 60, at least 70, at least 80, at least 90, at least 100, at least 120, or at least 150 bases per read. In some cases, each read is up to 2000, up to 1000, up to 900, up to 800, up to 700, up to 600, up to 500, up to 400, up to 300, up to 200, or up to 100 bases per read. Long read sequencing can include sequencing that provides a contiguous sequence read of for example, longer than 500 bases.

In some cases, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000. These machines use reversible terminator-based sequencing by synthesis chemistry. These machines can do 200 billion DNA or more reads in eight days. Smaller systems may be utilized for runs within 3, 2, or 1 days or less time. Short synthesis cycles may be used to minimize the time it takes to obtain sequencing results.

In some cases, high-throughput sequencing can involve the use of technology available by ABI Solid System. This genetic analysis platform can enable massively parallel sequencing of clonally-amplified DNA fragments linked to beads. The sequencing methodology is based on sequential ligation with dye-labeled oligonucleotides.

Next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an IONPROTON™ Sequencer is used to sequence nucleic acid. In some cases, an IONPGM™ Sequencer is used. The Ion Torrent Personal Genome Machine (PGM) can do 10 million reads in two hours.

In some cases, high-throughput sequencing involves the use of technology available by Helicos BioSciences Corporation (Cambridge, Mass.) such as the Single Molecule Sequencing by Synthesis (SMSS) method. SMSS can allow for sequencing the entire human genome in up to 24 hours. SMSS, like the MIP technology, may not require a pre amplification step prior to hybridization. SMSS may not require any amplification.

In some cases, high-throughput sequencing can involve the use of technology available by 454 Lifesciences, Inc. (Branford, Conn.) such as the Pico Titer Plate device which includes a fiber optic plate that transmits chemiluminescent signal generated by the sequencing reaction to be recorded by a CCD camera in the instrument. This use of fiber optics can allow for the detection of a minimum of 20 million base pairs in 4.5 hours.

Methods for using bead amplification followed by fiber optics detection are described in Marguiles, M., et al. "Genome sequencing in microfabricated high-density picolitre reactors", Nature, doi: 10.1038/nature03959; and well as in US Publication Application Nos. 20020012930.

In some cases, high-throughput sequencing is performed using Clonal Single Molecule Array (Solexa, Inc.) or sequencing-by-synthesis (SBS) utilizing reversible terminator chemistry. These technologies are described in part in U.S. Pat. No. 6,969,488.

In some cases, next generation sequencing can be nanopore. A nanopore can be a small hole, e.g., on the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridION system. A single nanopore can be inserted in a polymer membrane across the top of a microwell. Each microwell can have an electrode for individual sensing. The microwells can be fabricated into an array chip, with 100,000 or more microwells per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., SiNx, or $SiO_2$). The nanopore can be a hybrid pore (e.g., an integration of a protein pore into a solid-state membrane). The nanopore can be a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

Next generation sequencing can comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Adl) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., Acul), and the DNA can be cleaved by Acul 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Adl adapter. A restriction enzyme (e.g., Acul) can be applied, and the DNA can be cleaved 13 bp to the left of the Adl to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamethyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

The methods provided herein may include use of a system such as a system that contains a nucleic acid sequencer (e.g., DNA sequencer, RNA sequencer) for generating DNA or RNA sequence information. The system may include a computer comprising software that performs bioinformatic analysis on the DNA or RNA sequence information. Bioinformatic analysis can include, without limitation, assembling sequence data, detecting and quantifying genetic variants in a sample, including germline variants and somatic cell variants (e.g., a genetic variation associated with cancer or pre-cancerous condition, a genetic variation associated with infection).

Sequencing data may be used to determine genetic sequence information, ploidy states, the identity of one or more genetic variants, an origin of a target nucleic acid, as well as a quantitative measure of the variants, including relative and absolute relative measures.

In some cases, sequencing of the genome can involve whole genome sequencing or partial genome sequencing. The sequencing may be unbiased and may involve sequencing all or substantially all (e.g., greater than 70%, 80%, 90%) of the nucleic acids in a sample. Sequencing of the genome can be selective, e.g., directed to portions of the genome of interest. For example, many genes (and mutant forms of these genes) are known to be associated with various cancers. Sequencing of select genes, or portions of genes may suffice for the analysis desired. Polynucleotides mapping to specific loci in the genome that are the subject of interest can be isolated for sequencing by, for example, sequence capture or site-specific amplification.

Aligning Sequence Reads

Following sequencing, the dataset of sequences can be uploaded to a data processor for bioinformatics analysis to subtract host sequences, e.g., human, cat, dog, etc. from the analysis; and determine the presence and prevalence of pathogen or contaminant sequences (for example microbial sequences), for example by a comparison of the coverage of sequences mapping to a microbial reference sequence to coverage of the host reference sequence. The subtraction of host sequences may include the step of identifying a reference host sequence, and masking microbial sequences or microbial-mimicking sequences present in the reference host genome. Similarly, determining the presence of a microbial sequence by comparison to a microbial reference sequence may include the step of identifying a reference microbial sequence, and masking host sequences or host-mimicking sequences present in the reference microbial genome.

The dataset can be optionally cleaned to check sequence quality, remove remnants of sequencer specific nucleotides (adapter sequences), and merge paired end reads that overlap to create a higher quality consensus sequence with less read errors. Repetitive sequences can be identified as those having identical start sites and length, and duplicates may be removed from the analysis.

In some aspects, human sequences can be subtracted from the analysis. In some aspects, the amplification/sequencing steps can be unbiased and the preponderance of sequences in a sample will be host sequences. The subtraction process may be optimized in several ways to improve the speed and accuracy of the process, for example by performing multiple subtractions where the initial alignment is set at a coarse filter, e.g., with a fast aligner, and performing additional alignments with a fine filter such as. a sensitive aligner.

The database of reads can be initially aligned against a human reference genome, including without limitation Genbank hg19 or Genbank hg38 reference sequences, to bioinformatically subtract the host DNA. Each sequence can be aligned with the best fit sequence in the human reference sequence. Sequences positively identified as human can be bioinformatically removed from the analysis.

The reference human sequence can also be optimized by adding in contigs that have a high hit rate, including without limitation highly repetitive sequence present in the genome that are not well represented in reference databases. It has been observed that of the reads that do not align to hg19 or hg38, a significant amount is eventually identified as human in a later stage of the pipeline, when a database that includes a large set of human sequences is used, for example the entire NCBI NT database. Removing these reads earlier in the analysis can be performed by building an expanded human reference. This reference can be created by identifying human contigs in a human sequence database other than the reference, e.g. NCBI NT database, that have high coverage after the initial human read subtraction. Those contigs can be added to the human reference to create a more comprehensive reference set. Additionally, novel assembled human contigs from cohorts studies can be used as a further mask for human-derived reads.

Regions of the human genome reference sequence that contain non-human sequences may be masked, e.g. viral and bacterial sequences that are integrated into the genome of the reference sample.

Sequence reads identified as non-human can then aligned to a nucleotide database of microbial reference sequences. The database may be selected for those microbial sequences known to be associated with the host, e.g. the set of human commensal and pathogenic microorganisms.

The microbial database may be optimized to mask or remove contaminating sequences. For example, many public database entries include artifactual sequences not derived from the microorganism, e.g., primer sequences, host sequences, and other contaminants. It may be desirable to perform an initial alignment or plurality of alignments on a database. Regions that show irregularities in read coverage when multiple samples are aligned can be masked or removed as an artifact. The detection of such irregular coverage can be done by various metrics, such as the ratio between coverage of a specific nucleotide and the average coverage of the entire contig within which this nucleotide is found. In general a sequence that is represented as greater than about 5×, about 10×, about 25×, about 50×, about 100× the average coverage of that reference sequence can be artifactual. Alternatively, a binomial test can be applied to provide a per-base likelihood of coverage given the overall coverage of the contig. Removal of contaminant sequence from reference databases allows accurate identification of microbes.

Each high confidence read may align to multiple organisms in the given microbial database. To correctly assign organism abundance based upon this possible mapping redundancy, an algorithm can be used to compute the most likely organism (for example see Lindner et al. Nucl. Acids Res. (2013) 41 (1): e10). For example, GRAMMy or GASiC algorithms can be used to compute the most likely organism that a given read came from.

Alignments and assignment to a host sequence or to a non-host (e.g. microbial) sequence may be performed in accordance with art-recognized methods. For example, a read of 50 nt. may be assigned as matching a given genome if there is not more than 1 mismatch, not more than 2 mismatches, not more than 3 mismatches, not more than 4 mismatches, not more than 5 mismatches, etc. over the length of the read. Commercial algorithms are generally used for alignments and identification. A non-limiting example of such an alignment algorithm is the bowtie2 program (Johns Hopkins University).

These assignments of reads to an organism (e.g., host organism, non-host organism, microbe, pathogen, etc.) can then totaled and used to compute the estimated number of reads assigned to each organism in a given sample or sample of a dilution series, in a determination of the prevalence of the organism in the sample (for example, a cell-free nucleic acid sample) or each dilution of a dilution series. This information can be used to determine an origin of a pathogen or contaminant. The analysis can normalize the counts for the size of the microbial genome to provide a calculation of coverage for the microbe. The normalized coverage for each microbe can be compared to the host sequence coverage in the same sample to account for differences in sequencing depth between samples.

Further, a dataset of microbial organisms represented by sequences in the sample, and the prevalence of those microorganisms can be optionally aggregated and displayed for ready visualization, e.g., in the form of a report.

In some embodiments, the analysis disclosed herein can be used to compute a pathogenicity score, where the pathogenicity score is a numeric or alphabetic value that summarizes the overall pathogenicity of the organism for ease of interpretation, e.g. by a health practitioner. Different microbes present in the microbiome may be assigned different scores. The final "pathogenicity score" can be a combination of many different factors, and typically provided as an arbitrary unit, for example ranging from 0-1, 0-10 or 0-100; as a percentile from all observed pathogenicity scores for a microbe of interest, etc. The specific parameters and weights of those parameters may be determined experimentally, e.g. by fitting the function to observed disease severity, or manually by setting the importance of different parameters and criteria.

Factors relevant for calculation of a pathogenicity score may include, without limitation, abundance of the microbe, e.g. as computed by number of reads relative to human reads, relative to the abundance of the microbe in a reference subject or group of subjects, e.g. a test population, a known infection, a known un-infected individual, etc. Specific mutations found in the microbe genome, which may be made with reference to a database of toxicity, pathogenicity, antibiotic resistance etc. associated with the microbe, and including without limitation SNPs, indels, plasmids etc. The co-incidence of specific microbes, including without limitation specific ratios and groups of organisms. Expression of certain pattern of coverage over the genome for DNA (which can show great bias towards the origin of replication during rapid division) or sequences, e.g. be detection of mRNA, can be relevant to the pathogenicity score, e.g. as informative of whether a microbe is actively replicating or is latent; etc. Geographic features may also be included, where the geography is indicative of exposure to microbes of interest, e.g. travel history of the host; interactions with infected individuals, and the like.

Nucleic Acid Extraction and Amplification

The methods described herein may comprise extracting nucleic acids (e.g., target nucleic acids, cell-free nucleic acids) from a sample. A sample can be dilutions of a dilution series. The extraction may comprise separating the nucleic acids from other cellular components and contaminants that may be present in the sample, e.g., biological fluid or tissue sample. In some cases, the extraction can be performed by phenol chloroform extraction or precipitation by organic solvents (e.g., ethanol, or isopropanol). In some cases, the extraction can be performed using nucleic acid-binding columns. In some cases, the extracting nucleic acids from the sample is performed using magnetic beads. In some cases, the extraction can be performed using commercially available kits such as the Qiagen Qiamp Circulating Nucleic Acid Kit Qiagen Qubit dsDNA HS Assay kit, Agilent™ DNA 1000 kit, TruSeq™ Sequencing Library Preparation, or nucleic acid-binding spin columns (e.g., Qiagen DNA mini-prep kit). In some cases, extraction of cell-free nucleic acids may involve filtration or ultra-filtration. In some cases, extraction and/or purification of nucleic acids can include depletion of non-nucleic acid components from samples (e.g. depletion of albumin from plasma).

Nucleic Acid Purification

The method may comprise purifying the target nucleic acids. Exemplary purification methods include ethanol precipitation, isopropanol precipitation, phenol chloroform purification, and column purification (e.g., affinity-based column purification), dialysis, filtration, or ultrafiltration.

Fragmentation

The method may comprise fragmenting the target nucleic acids. Fragmenting of the target nucleic acids may be performed by e.g., mechanical shearing, passing the sample through a syringe, sonication, heat treatment, or a combination thereof. In some cases, shearing may be performed by mechanical shearing (e.g. ultrasound, hydrodynamic shearing forces), enzymatic shearing (e.g. endonuclease), thermal fragmentation (e.g. incubation at high temperatures), chemical fragmentation (e.g. alkaline solutions, divalent ions). In some cases, fragmenting of the target nucleic acids can be performed by using an enzyme, including a nuclease, or a transposase. Nucleases used for fragmenting may comprise restriction endonucleases, homing endonucleases, nicking endonucleases, high fidelity restriction enzymes, or any enzyme disclosed herein. The methods may comprise fragmenting the target nucleic acids into fragments of certain length, e.g., 50, 60, 80, 100, 120, 140, 160, 200, 500, or 1000 bp in length.

A-Tailing

The method may comprise performing A-tailing on the target nucleic acids. An A-tailing reaction may be performed by using one or more A-tailing enzymes. For example, an adenine (A) residue can be added by incubating a DNA fragment with dATP and a non-proofreading DNA polymerase, which will add a single 3' A residue.

End Repair

The method may comprise performing end repair on the target nucleic acids. For example, end repair may be performed on the target nucleic acids so they may be suitable for other steps. The end repair reaction may be performed by using one or more end repair enzymes. Enzymes for repairing DNA may include polymerase, exonuclease and/or PNK (e.g Endonuclease VIII). Enzymes disclosed herein can refer to one or more of an endonuclease, e.g., type I, type II (including type IIS, type IIG), type III or type IV endonuclease), a restrictive endonuclease, or any combination thereof, a DNase not mentioned above, or an exoribonuclease, such as polynucleotide phosphorylase, RNase PH, or any combination thereof. In some cases, a polymerase may fill in the missing bases for a DNA strand from 5' to 3' direction. The resulting double-stranded DNA may have substantially the same length as the original longest DNA strand. Exonuclease may remove the 3' overhangs. The resulting double-stranded DNA may have substantially the same length as the original shortest DNA strand.

Adapter Attachment

A sequencing adapter may attach to a target nucleic acid and help the sequencing of the target nucleic acid. For example, a sequencing adapter may comprise one or more of: a sequencing primer binding site, a unique identifier sequence, a non-unique identifier sequence, and a sequence for immobilizing target nucleic acid on a solid support. A target nucleic acid attached with a sequencing adapter may be immobilized on a solid support on a sequencer. A sequencing primer may hybridize to the adapter and be extended using the target nucleic acid as a template in a sequencing reaction. In some cases, the unique identifiers in an adapter can be used to label the sequence reads of different target sequences, thus allowing high-throughput sequencing of a plurality of target nucleic acids.

The methods may comprise attaching one or more adapters to the target nucleic acids. Adapters may be attached to a target nucleic acid by primer extension, reverse transcription, or hybridization. In some cases, an adapter can be attached to a target nucleic acid by ligation. For example, an adapter may be attached to a target nucleic acid by a ligase. For example, an adapter may be attached to a target nucleic acid by sticky-end ligation, blunt-end ligation, or by a transposase. A target nucleic acid may be attached to an adapter at the 3' end, the 5' end, or both ends. Before attaching the adapter to the target nucleic acids in a sample, the sample may be treated with an enzyme. For example, the sample may be treated with an endonuclease to create ligation site, e.g., a sticky end or a blunt end. Alternatively, a sample may be treated with an enzyme after the adapter attaches to the target nucleic acids.

In some cases, an adapter can comprise a barcode (e.g. unique identifier sequence). In some cases, an adapter can be an amplification adapter. An amplification adapter may attach to a target nucleic acid and help the amplification of the target nucleic acid. For example, an amplification adapter may comprise one or more of: a primer binding site, a unique identifier sequence, a non-unique identifier sequence, and a sequence for immobilizing the target nucleic acid on a solid support. In some cases, an adapter can be a sequencing adapter.

Amplification

The methods may comprise amplifying target nucleic acids. Amplification may refer to any method for increasing the number of copies of a nucleic acid sequence. For example, the amplification may be performed with a polymerase, e.g., in one or more polymerase chain reactions. Amplification may be performed using methods known in the art. These methods often depend on the product catalyzed formation of multiple copies of a nucleic acid or its complement. One of such methods is polymerase chain reaction (PCR), including AFLP (amplified fragment length polymorphism) PCR, allele-specific PCR, Alu PCR, assembly, asymmetric PCR, colony PCR, helicase dependent PCR, hot start PCR, inverse PCR, in situ PCR, intersequence-specific PCR or IS SR PCR, digital PCR, droplet digital PCR, linear-after-the-exponential-PCR or Late PCR, long PCR, nested PCR, real-time PCR, duplex PCR, multiplex PCR, quantitative PCR, or single cell PCR. Other amplification methods may also be used, including ligase chain reaction (LCR), nucleic acid sequence based amplification (NASBA), linear amplification, isothermal linear amplification, Q-beta-replicase method, 3SR, Transcription Mediated Amplification (TMA), Strand Displacement Amplification (SDA), or Rolling Circle Amplification (RCA). In other cases, amplification may not be necessary. In some cases, amplification is not necessary for sample preparation.

Contamination

Environmental Contamination

The methods provided herein can enable one to distinguish between DNA or other nucleic acids that arose from an infection or normal commensal organisms and DNA or other nucleic acids from environmental contamination or reagent contamination. In practice, the environmental contaminant or reagent contaminant alone may give rise to DNA or nucleic acids that maps to hundreds of different species, with a very broad range of abundances. Environmental contamination can refer to the introduction of contaminants from the environment during sample collection, handling and/or processing. For example, exposure of the sample, such as a plasma sample, to the environment may result in the introduction of contaminants from the environment to the sample.

Nucleic acid reagents used for sample handling and processing may also be a source of contaminants. Contaminants within a nucleic acid reagent include any contaminant introduced into the reagent by exposure to the environment including during manufacture of the reagent. Contaminants may be nucleic acids or may be a cell such as a bacterial cell, or any other natural or synthetic material containing nucleic acids. In some instances, the contaminant can be derived from a human, such as a lab worker or plant worker. In some instances, the contaminant is derived from a non-human organism, particularly a pathogen such as a microbe, bacterium, virus, fungus, parasite, worm, or any combination thereof.

In some cases, contaminant nucleic acids may include nucleic acids derived from one or more eukaryotic species, one or more prokaryotic species, one or more viral species, one or more fungal species, or any combination thereof. In some cases, contaminant nucleic acids may include nucleic acids derived from Propionibacterium acnes, *Bradyrhizobium* sp. S23321, *Bradyrhizobium diazoefficiens, Bradyrhizobium japonicum, Acidovorax* sp. KKS102, *Bra-*

*dyrhizobium* sp. BTAi1, or any combination thereof. In some cases, contaminant nucleic acids may include nucleic acids derived from genera *Bradyrhizobium, Rhizobium/Agrobacterium, Sphingomonas, Burkholderia, Ralstonia, Pseudomonas, Stenotrophomonas, Flavobacterium*, or any combination thereof. In some cases, contaminant nucleic acids may include nucleic acids derived from *Bradyrhizobium* or *Bradyrhizobium* sp. DFCI-1. In some cases, contaminant nucleic acids may include nucleic acids derived from *Escherichia coli*. In some cases, contaminant nucleic acids may include nucleic acids derived from Bos (e.g., cow), Sus (e.g., pig), Gallus (e.g., chicken), or any combination thereof. In some cases, a contaminant e.g. environmental contaminant can be or derived from one or more of *Methylophilus, Acidovorax, Afipia, Acanthamoeba, Melampsora, Bradyrhizobium, Sediminibacterium, Microbacterium, Micrococcus, Corynebacterium, Pelomonas, Cupriavidus, Propionibacterium, Aquabacterium, Brevundimonas, Streptomyces, Mycobacterium, Delftia, Ralstonia, Eschericia, Staphylococcus, Massilia, Acinetobacter, Tepidimonas, Shingomonas, Sphingobium, Methylobaceterium, Asanoa, Rhodococcus, Rhodanobacter, Variovorax, Stenotrophomanas, Pseudomonas, Burkholderia*, or *Achromobacter*. In some aspects, a contaminant nucleic acid can be derived from any species disclosed herein. In other aspects, a contaminant nucleic acid, pathogen nucleic acid, and/or a target nucleic acid can be derived from the same or different kingdom. In some aspects, a contaminant nucleic acid and pathogen nucleic acids/target nucleic acid can be derived from bacteria. In some aspects, a contaminant nucleic acid and pathogen nucleic acids/target nucleic acid can be derived from fungi. In some aspects, a contaminant nucleic acid and pathogen nucleic acids/target nucleic acid can be derived from virus. In some aspects, a kingdom can comprises eubacteria, archae, Protista, fungi, plantae or Animalia. In other aspects, contaminant nucleic acid can be derived from a fungi and pathogen nucleic acid can be derived from a bacteria. In other aspects, contaminant nucleic acid can be derived from a fungi and pathogen nucleic acid can be derived from a virus. In other aspects, contaminant nucleic acid can be derived from a fungi and pathogen nucleic acid can be derived from a bacteria. In other aspects, contaminant nucleic acid can be derived from a fungi and pathogen nucleic acid can be derived from a fungi. In other aspects, contaminant nucleic acid can be derived from a bacteria and pathogen nucleic acid can be derived from a bacteria. In other aspects, contaminant nucleic acid can be derived from a bacteria and pathogen nucleic acid can be derived from a virus. In other aspects, contaminant nucleic acid can be derived from a bacteria and pathogen nucleic acid can be derived from a bacteria. In other aspects, contaminant nucleic acid can be derived from a fungi and pathogen nucleic acid can be derived from a fungi. In other aspects, contaminant nucleic acid can be derived from a virus and pathogen nucleic acid can be derived from a bacterium. In other aspects, contaminant nucleic acid can be derived from a virus and pathogen nucleic acid can be derived from a virus. In other aspects, contaminant nucleic acid can be derived from a virus and pathogen nucleic acid can be derived from a bacterium. In other aspects, contaminant nucleic acid can be derived from a fungi and pathogen nucleic acid can be derived from a fungi. In other aspects, contaminant nucleic acids and a pathogen nucleic acid can be derived from the same species. In some aspects, contaminant nucleic acids and a pathogen nucleic acid can be derived from different species.

In some aspects, a contaminant nucleic acid can be present in a sample at a high concentration and a pathogen nucleic acid can be present in a sample at a high concentration. In some aspects, a contaminant nucleic acid can be present in a sample at a low concentration and a pathogen nucleic acid can be present in a sample at a high concentration. In some aspects, a contaminant nucleic acid can be present in a sample at a high concentration and a pathogen nucleic acid can be present in a sample at a low concentration. In some embodiment a high or low concentration of a pathogen nucleic acid can be relative to a concentration of contaminant nucleic acid. In some embodiment a high or low concentration of a contaminant nucleic acid can be relative to a concentration of pathogen nucleic acid. In some aspects, a sample can comprise at least 1, 2, 3, 4, 5, 6, 7, 8, 9, 10 or more different pathogen nucleic acid. In some aspects, a sample can comprise at least 1, 2, 3, 4, 5, 6, 7, 8, 9, 10 or more different contaminant nucleic acid.

As is the case with the sample nucleic acids, the contaminant nucleic acids may be any type of nucleic acid including: double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating DNA, circulating RNA, cell-free nucleic acids, cell-free DNA, cell-free RNA, circulating cell-free DNA, circulating cell-free RNA, genomic DNA, mitochondrial nucleic acids, or any combination thereof. In some examples, the contaminant nucleic acids can be in the form of double stranded DNA fragments at low concentrations in various solutions. The length of contaminant nucleic acids can vary. In some cases, contaminant nucleic acids may be about or at least about 10, 20, 30, 40, 50, 60, 70, 80, 90, 100, 150, 160, 170, 180, 190, or 200 nucleotides in length. In some cases, contaminant nucleic acids may be up to about 20, 30, 40, 50, 60, 70, 80, 90, 100, 120, 130, 140, 150, 160, 170, 180, 190, 200, 250, 300, 350 nucleotides in length.

In some cases, the contaminant nucleic acids may make up about or at least about 0.00001%, 0.00005%, 0.0001%, 0.0005%, 0.001%, 0.005%, 0.01%, 0.05%, 0.1%, 0.5%, or 1% of total nucleic acid in a sample, sequencing reads or read pairs. In some cases, the concentration of contaminant nucleic acids may be no more than 0.00000001%, 0.00000005%, 0.0000001%, 0.0000005%, 0.000001%, 0.000005%, 0.00001%, 0.00005%, 0.0001%, 0.0005%, 0.001%, 0.005%, 0.01%, 0.05%, 0.1%, 0.5%, or 1% of total sequencing reads or read pairs. In some cases, the concentration of contaminant nucleic acids may be within the range between about 0.000001% and 1%, between about 0.000001% and about 0.1%, between about 0.000005% and about 0.1%, or between about 0.000005% and 0.05% of total sequencing reads or read pairs.

In some cases, the concentration of contaminant nucleic acids in the nucleic acid reagent may be about or at least about 1 μM, 10 μM, 100 μM, 1 nM, 10 nM, 100 nM, 1 μM, 10 μM, or 100 μM. In some cases, the concentration of contaminant nucleic acids may be less than or equal to about 1 μM, 10 μM, 100 μM, 1 nM, 10 nM, 100 nM, 1 μM, 10 μM, or 100 μM.

In some cases, the degree of contaminant nucleic acid reduction or inactivation is about or at least about 20%, 25%, 30%, 40%, 50%, 60%, 80%, 95%, or 99.99%. In some cases, a dilution of a sample, such as a plasma sample, may not alter the concentration of an environmental contaminant present in the sample.

Diluent-Derived Contamination

The diluent used to dilute a sample may be another source of contamination. A diluent may contain the same types of contaminants found as a result of environmental contamination. For example, exposure of the diluent to the environment may result in the introduction of contaminants from the environment to the diluent. Contaminants in the diluent may also be the result of introduction of a contaminant during manufacture of the diluent. A contaminant present in a diluent may differ from a pathogen present in a sample or a reagent. Accordingly, in some instances, with increasing dilution of the plasma sample, the concentration of the contaminant that is diluent-derived increases, while the concentration of a sample-derived pathogen decreases. As a result, in some cases, a signal for the diluent-derived contaminant may increase with increasing fold dilution. Conversely, the signal for the sample-derived pathogen may decrease with increasing dilution. "Diluent-derived" and "diluent based" or grammatical equivalents can be used interchangeably herein.

Environmental Pathogens

Contaminants may include pathogens that are introduced to a sample or a reagent used for sample handling and processing. Common environmental contaminants include common human pathogens. Any pathogen may be found in the environment, including, but not limited to, a microbe, bacterium, virus, fungus, parasite, worm, or any combination thereof. A pathogen found in the environment may be the same or different from a pathogen found in a sample to be analyzed for the presence of pathogens.

Exemplary contaminant pathogens that may be found in the environment include pathogens associated with diseases or disorders associated with an infection, e.g., sepsis, pneumonia, tuberculosis, HIV infection, hepatitis infection (e.g., Hep A, B, or C), human papilloma virus (HPV) infection, chlamydial infection, syphilitic infection, Ebola infection, *Staphylococcus aureus* infection, or influenza. The methods provided herein are particularly useful for detecting infections by drug-resistant microbes, including multi-drug resistant microbes, or microbes that are not readily cultured or typically tested for. Some non-limiting examples of diseases and disorders that may be detected with the present methods include: cancer, dilated cardiomyopathy, Guillain-Barre syndrome, multiple sclerosis, tuberculosis, anthrax poisoning, sleeping sickness, dysentery, toxoplasmosis, ringworm, candidiasis, histoplasmosis, Ebola, *Acinetobacter* infections, Actinomycosis, African sleeping sickness (African trypanosomiasis), AIDS (Acquired immunodeficiency syndrome), HIV infection, Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, Baylisascaris infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, *Chlamydia, Chlamydophila pneumoniae* infection (Taiwan acute respiratory agent or TWAR), Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Filariasis, Food poisoning by *Clostridium perfringens*, Free-living amebic infection, *Fusobacterium* infection, Gas gangrene (*Clostridial myonecrosis*), Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, Salmonellosis, SARS (Severe Acute Respiratory Syndrome), *Scabies*, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)),

*Trachoma*, Trinochccliasis, Trichinlosis, Trichomoniasis, Trichuriasis (Whipworm infection), Tuberculosis, Tularemia, Typhoid Fever, *Ureaplasma urealyticum* infection, Valley fever, Venezuelan equine encephalitis, Venezuelan hemorrhagic fever, Viral pneumonia, West Nile Fever, White piedra (*Tinea blanca*), *Yersinia* pseudotuberculosis infection, Yersiniosis, Yellow fever, and Zygomycosis.

Sample-Derived Pathogens

Any pathogen may be found a sample to be analyzed for the presence of pathogens, including, but not limited to, a microbe, bacterium, virus, fungus, parasite, nematodes, worm, or any combination thereof. A pathogen present in a sample may be the same or different from a pathogen found in the environment or in a reagent.

A sample may comprise any pathogen associated with diseases or disorders associated with an infection, e.g., sepsis, pneumonia, tuberculosis, HIV infection, hepatitis infection (e.g., Hep A, B, or C), human papilloma virus (HPV) infection, chlamydial infection, syphilitic infection, Ebola infection, *Staphylococcus aureus* infection, or influenza. The methods provided herein are particularly useful for detecting infections by drug-resistant microbes, including multi-drug resistant microbes, or microbes that are not readily cultured or typically tested for. Some non-limiting examples of diseases and disorders that may be detected with the present methods include: cancer, dilated cardiomyopathy, Guillain-Barre syndrome, multiple sclerosis, tuberculosis, anthrax poisoning, sleeping sickness, dysentery, toxoplasmosis, ringworm, candidiasis, histoplasmosis, Ebola, *Acinetobacter* infections, Actinomycosis, African sleeping sickness (African trypanosomiasis), AIDS (Acquired immunodeficiency syndrome), HIV infection, Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, Baylisascaris infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, *Chlamydia, Chlamydophila pneumoniae* infection (Taiwan acute respiratory agent or TWAR), Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Filariasis, Food poisoning by *Clostridium perfringens*, Free-living amebic infection, *Fusobacterium* infection, Gas gangrene (*Clostridial myonecrosis*), Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, Salmonellosis, SARS (Severe Acute Respiratory Syndrome), *Scabies*, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)), *Trachoma*, Trinochccliasis, Trichinlosis, Trichomoniasis, Trichuriasis (Whipworm infection), Tuberculosis, Tularemia, Typhoid Fever, *Ureaplasma urealyticum* infection, Valley fever, Venezuelan equine encephalitis, Venezuelan hemorrhagic fever, Viral pneumonia, West Nile Fever, White piedra (*Tinea blanca*), *Yersinia* pseudotuberculosis infection, Yersiniosis, Yellow fever, and Zygomycosis.

Reagent-Derived Pathogens

Contaminating pathogens or nucleic acids may be present in a reagent that is used to process a sample that is used in the methods provided herein (e.g., methods of producing a sample series or dilution series). The presence of a pathogen in a reagent may be the result of exposure to the environment or of introduction of the pathogen during manufacturing or preparation of the reagent. A pathogen present in a reagent may be the same or different as a pathogen present in the sample to be analyzed, such as a target nucleic acids.

A reagent may comprise any type of microbe. In some cases, a reagent contains a pathogen associated with diseases or disorders associated with an infection, e.g., sepsis, pneumonia, tuberculosis, HIV infection, hepatitis infection (e.g., Hep A, B, or C), human papilloma virus (HPV) infection, chlamydial infection, syphilitic infection, Ebola infection, *Staphylococcus aureus* infection, or influenza. The methods provided herein are particularly useful for detecting infections by drug-resistant microbes, including multi-drug resistant microbes, or microbes that are not readily cultured or typically tested for. Some non-limiting examples of diseases and disorders that may be detected with the present methods include: cancer, dilated cardiomyopathy, Guillain-Barre syndrome, multiple sclerosis, tuberculosis, anthrax poisoning, sleeping sickness, dysentery, toxoplasmosis, ringworm, candidiasis, histoplasmosis, Ebola, *Acinetobacter* infections, Actinomycosis, African sleeping sickness (African trypanosomiasis), AIDS (Acquired immunodeficiency syndrome), HIV infection, Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, Baylisascaris infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, *Chlamydia, Chlamydophila pneumoniae* infection (Taiwan acute respiratory agent or TWAR), Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Filariasis, Food poisoning by *Clostridium perfringens*, Free-living amebic infection, *Fusobacterium* infection, Gas gangrene (*Clostridial myonecrosis*), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, Salmonellosis, SARS (Severe Acute Respiratory Syndrome), *Scabies*, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)), *Trachoma*, Trinochccliasis, Trichinlosis, Trichomoniasis, Trichuriasis (Whipworm infection), Tuberculosis, Tularemia, Typhoid Fever, *Ureaplasma urealyticum* infection, Valley fever, Venezuelan equine encephalitis, Venezuelan hemorrhagic fever, Viral pneumonia, West Nile Fever, White piedra (*Tinea blanca*), *Yersinia* pseudotuberculosis infection, Yersiniosis, Yellow fever, and Zygomycosis.

Diluent/Reagent-Derived Pathogens

Pathogens may be present in a diluent that is added to a sample to be analyzed. The presence of a pathogen in a diluent may be the result of exposure of the diluent to the environment or introduction of the pathogen from the environment during manufacturing or preparation of the diluent. A pathogen present in a diluent may be the same or different than a pathogen present in the sample to be analyzed.

In some instances, where the pathogen in a diluent is different than the pathogen present in the sample to be analyzed, increasing fold dilution of the sample with the diluent will result in an increasing concentration of the diluent-derived pathogen and a decreasing concentration of the sample-derived pathogen. In cases where the pathogen (or microbe) in a diluent is the same as the sample-derived pathogen, but present at different concentrations, the sample-derived pathogen may be confirmed by the functional form of the pathogen concentration as a function of the dilution factor.

A diluent may comprise any pathogen associated with diseases or disorders associated with an infection, e.g., sepsis, pneumonia, tuberculosis, HIV infection, hepatitis infection (e.g., Hep A, B, or C), human papilloma virus (HPV) infection, chlamydial infection, syphilitic infection, Ebola infection, *Staphylococcus aureus* infection, or influenza. The methods provided herein are particularly useful for detecting infections by drug-resistant microbes, including multi-drug resistant microbes, or microbes that are not readily cultured or typically tested for. Some non-limiting examples of diseases and disorders that may be detected with the present methods include: cancer, dilated cardiomyopathy, Guillain-Barre syndrome, multiple sclerosis, tuberculosis, anthrax poisoning, sleeping sickness, dysentery, toxoplasmosis, ringworm, candidiasis, histoplasmosis, Ebola, *Acinetobacter* infections, Actinomycosis, African sleeping sickness (African trypanosomiasis), AIDS (Acquired immunodeficiency syndrome), HIV infection, Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, Baylisascaris infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, *Chlamydia, Chlamydophila pneumoniae* infection (Taiwan acute respiratory agent or TWAR), Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Filariasis, Food poisoning by *Clostridium perfringens*, Free-living amebic infection, *Fusobacterium* infection, Gas gangrene (*Clostridial myonecrosis*), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, Salmonellosis, SARS (Severe Acute Respiratory Syndrome), *Scabies*, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manum* (Ringworm of the Hand), *Tinea nigra, Tinea pedis* (Athlete's foot), *Tinea unguium* (Onychomycosis), *Tinea versicolor* (*Pityriasis versicolor*), Toxocariasis (Ocular Larva Migrans (OLM)), Toxocariasis (Visceral Larva Migrans (VLM)), *Trachoma*, Trinochccliasis, Trichinlosis, Trichomoniasis, Trichuriasis (Whipworm infection), Tuberculosis, Tularemia, Typhoid Fever, *Ureaplasma urealyticum* infection, Valley fever, Venezuelan equine encephalitis, Venezuelan hemorrhagic fever, Viral pneumonia, West Nile Fever, White piedra (*Tinea blanca*), *Yersinia* pseudotuberculosis infection, Yersiniosis, Yellow fever, and Zygomycosis.

Microbes

Any microbe may be a contaminant. Microbes may include bacteria, fungi, viruses, and protozoa, for example. A contaminating microbe may be a pathogen. However, a contaminating microbe may also be non-pathogenic, or may even be a commensal organism.

Bacteria

Any bacterium may be a contaminant. Exemplary contaminant bacteria are described in detail below.

*Helicobacter*

*Helicobacter* are gram-negative bacteria with a characteristic helical shape. *Helicobacter* species have been found in the lining of the upper gastrointestinal tract, the liver of mammals, and in some birds. The most widely known species of the genus is *H. pylori* that infects up to 50% of the human population and includes pathogenic strains associated with peptic ulcers, chronic gastritis, duodenitis, and stomach cancer. *Helicobacter* species are able to thrive in low pH environments by producing the enzyme urease which locally raises pH from about 2 in the acidic environment of the human stomach, for example, to a pH range of 6-7. Additional gastric species of *Helicobacter* include *H. suis, H. baculiformis, H. felis, H bizzozeronii*, and *H. salomonis*. An example of a recently identified enterohepatic

*Helicobacter* species is *H. equorum*. Additional enterohepatic species include *H. hepaticus, H. bilis*, and *H. ganmani.*

Although *H. pylori* is of primary importance for medicine, non-*H. pylori* species, which naturally inhabit mammals other than humans and birds, have been detected in human clinical specimens. Some species, such as *H. hepaticus, H. mustelae*, and possibly *H. bilis*, exhibit carcinogenic potential in animals. Avian helicobacters include *H. pullorum, H. anseris*, and *H. brantae*. Additional *Helicobacter* species of clinical significance include *H. cinaedi* and *H. canis* which can cause severe infections in immunocompromised patients with animal exposure.

*Staphylococcus epidermidis*

*Staphylococcus epidermidis* belongs to the genus *Staphylococcus. S. epidermidis* is a Gram-positive, non-motile bacterium that is part of the normal human flora, typically the skin flora and less commonly the mucosal flora. Although not usually pathogenic, patients with compromised immune systems are at risk of infection upon exposure to *S. epidermidis*. Infections with *S. epidermidis* are typically hospital-acquired. Moreover, because *S. epidermidis* is part of the normal skin flora, *S. epidermidis* is a common contaminant of patient specimens that are analyzed in diagnostic laboratories.

*Methylobacterium*

Methylobacteria belong to the species *Rhizobiales*. Methylbacterium is normally found in soil and water. *Methylobacterium* has been identified as a contaminant of reagents for DNA extraction, including kits. As a result, *Methylobacterium* may erroneously appear in microbiota or metagenomic datasets.

*Lactococcus lactis*

*Lactococcus lactis* is a Gram-positive bacterium with cocci cells that group in pairs or short chains. *L. lactis* does not produce spores and is not motile. *L. lactis* is used extensively in the production of dairy products such as buttermilk and cheese. *L. lactis* is mainly isolated from either the dairy environment or from plant material.

*Haemophilus*

The genus *Haemophilus* belongs to the Pasteurellacea family and is a genus of Gram-negative, pleomorphic, coccobacilli bacteria. *Haemophilus* inhabit the mucous membranes of the upper respiratory tract, mouth, vagina, and intestinal tract. The genus includes both pathogenic and commensal organisms. Examples of pathogenic species include *H. influenzae* and *H. ducreyi. H. influenzae* and *H. ducreyi* are the causes of sepsis and bacterial meningitis in young children and chancroid, respectively. *Haemophilus* has been found to be part of the salivary microbiome.

Fungus

Any fungus may be a contaminant. Fungi are eukaryotic organisms that include yeasts and molds. Fungi may be single celled organisms or multicellular. Fungi include species that are used in the production of food, such as yeasts for example, as well as species that are pathogenic. Examples of pathogenic fungi include, but are not limited to, *Aspergillus, Candida, Cryptococcus, Histoplasma*, and *Pneumocystis*. Fungi may also form spores that are readily carried through the environment and that are a frequent cause of allergies.

Virus

Viruses are small infectious agents that replicate within cells of other organisms. Viruses can infect any type of organism, including animals, plants, fungi, and bacteria, for example. Viruses are broadly grouped into enveloped and naked viruses. Enveloped viruses typically derive a lipid envelope from the cell or nuclear membrane of the host cell. Naked viruses do not have a lipid envelope, but instead have a proteinaceous shell that surrounds the viral nucleic acid. The genome of a virus may be DNA or RNA, and may be single-stranded or double-stranded. Many viruses in numerous virus families are of medical and veterinary importance as causing numerous diseases.

Numerous virus families have been described, including, but not limited to, Picornaviridae, Togaviridae, Coronaviridae, Rhabdoviridae, Orthomyxoviridae, Paramyxoviridae, Flaviviridae, Bunyaviridae, Arenaviridae, Reoviridae, Retroviridae, Papovaviridae, Adenoviridae, Parvoviridae, Herpesviridae, and Hepadnaviridae.

Protozoa

Protozoa are a diverse group of unicellular eukaryotic organisms. Exemplary phyla of protozoa include Euglenozoa, Amoebozoa, Metamonada, Choanozoa, Loukozoa, Percolozoa, Microsporidia and Sulcozoa. Protozoa may be pathogens of humans, causing diseases such as malaria (caused by *Plasmodium*), amoebiasis, giardiasis, toxoplasmosis, cryptosporidiosis, trichomoniasis, Chagas disease, leishmaniasis, African trypanosomiasis (sleeping sickness), amoebic dysentery, acanthamoeba keratitis, and primary amoebic meningoencephalitis (naegleriasis).

Sterilizing Reagents and Sample

Contaminants within reagents, diluents, and/or samples may be inactivated or removed by any of a number of methods or approaches and combinations thereof. In some cases, the contaminants are inactivated by exposure to radiation (e.g., UV, gamma irradiation); in some cases, the contaminants can be inactivated by exposure to heat; in some cases, the contaminants can be inactivated by exposure to a chemical; and in some cases, enzymes such as nucleases can be used to degrade the contaminant nucleic acids. In other cases, nucleic acids may be inactivated by a combination of one or more methods disclosed herein. Examples of such types of removal include but are not limited to: replacing contaminated reagents or diluent with decontaminated or less contaminated reagents and diluent, washing solid materials with clean solutions such as water, filtering nucleic acid reagents, or otherwise treating solutions with nucleic acid binding materials. Another method is to bioinformatically subtract reads determined to be common contaminants (for example, from parallel sterile water input control samples). In some embodiments, the contaminating nucleic acids derived from the reagents and/or diluent are identified bioinformatically through reagent- and diluent-specific barcodes attached to these nucleic acids before using reagents and before using diluent in a dilution series. In some embodiments, reagents and samples can be sterilized by any method described herein. Any method described herein can effectively removing contaminants or any signal derived from contaminants as used alone or in combination with another method disclosed herein. See also, for example, PCT/US2017/045782 titled "Reduction of Signal From Contaminant Nucleic Acids".

Ethidium Monoazide

Ethidium monoazide (EMA) is a fluorescent photoaffinity label that binds covalently to nucleic acids after photolysis. EMA binds to nucleic acid in solution and to DNA in cells with compromised cell membranes. Because DNA covalently bound to EMA cannot be amplified by PCR, EMA is used to differentiate between viable and dead bacteria, for example. Similarly, EMA bound to a contaminating nucleic acid will not be amplified by PCR, thereby effectively eliminating the signal from the contaminant.

Propidium Monoazide

Propidium monoazide (PMA) is a photoreactive dye that preferentially binds to double-stranded DNA. Visible light induces a photoreaction that results in a covalent bond between PMA and DNA. The covalent bond renders the DNA unable to be amplified in PCR. Because naked DNA in a sample reacts with PMA, while DNA in a living bacterium, for example, is protected, the naked DNA will not be amplified. This allows for distinguishing between the presence of live and dead bacteria and the determination of which pathogens are active in a sample, for example. Importantly, use of PMA effectively eliminates a signal from any naked DNA, including any contaminating nucleic acid.

DNAse

Contaminant nucleic acids can be inactivated by treatment with one or more enzymes, such as nucleases. A nuclease is generally an enzyme capable of cleaving the phosphodiester bonds between the nucleotide subunits of nucleic acids. Endonucleases and exonucleases are types of nucleases. Endonucleases include, but are not limited to deoxyribonuclease (e.g., DNase I), heat-labile dsDNase, restriction enzymes, and Cas proteins (e.g., Cas9). In some cases, after treatment of the contaminant nucleic acids, an endonuclease or other enzyme can be removed or inactivated (e.g., by heating).

Restriction Enzymes

Restriction enzymes are endonucleases that cleave nucleic acids at specific sequences or recognition sites. Any restriction enzyme may be used for the inactivation of contaminant nucleic acids. Naturally occurring restriction enzymes are classified as type I, type II, type III, type IV, based on their composition and enzyme cofactor requirements, the nature of their target sequence, and the position of their DNA cleavage site relative to the target sequence. Type V restriction enzymes include that utilize guide RNAs to target specific non-palindromic sequences. Artificial restriction enzymes, such as zinc finger nucleases and TAL effectors, have also been described.

Radiation

Contaminating nucleic acid fragments in reagents (e.g., nucleic acid sequencing preparation materials) or samples, or from other elements of the environment may be inactivated with irradiation, for example using ultraviolet light (UV) or gamma irradiation. DNA damaged with UV may not be a substrate for the DNA polymerases used in library preparation and in the sequencing reaction and thus may not be detected. Likewise, gamma irradiation can damage the bases of the DNA and prevent copying and/or detection, or can break the DNA backbone. In other instances, with a high enough dose, gamma irradiation can reduce the DNA fragment sizes below the detection limit of the extraction or library preparation methods. Reagents and other materials used in preparing a sample for sequencing "cleaned" in this way may still contain contaminating nucleic acids, but these inactivated or damaged nucleic acids may avoid detection by the sequencing system.

Non-limiting examples of electromagnetic radiation include gamma rays, X-rays (e.g., hard X-rays, soft X-rays), and ultraviolet (e.g., ultraviolet A, ultraviolet B, ultraviolet C, extreme ultraviolet, vacuum ultraviolet, far ultraviolet, middle ultraviolet, near ultraviolet). In some cases, the wavelength of the electromagnetic radiation is about or at least about 1 pm, 5 pm, 10 pm, 50 pm, 100 pm, 500 pm, 1 nm, 5 nm, 10 nm, 50 nm, 100 nm, 500 nm, or 1 μm. In some cases, the wavelength of the electromagnetic radiation is 254 nm. In some cases, the electromagnetic radiation is ultraviolet C.

Heating

Application of heat to a reagent or nucleic acid analysis buffer may or may not be used in the methods provided herein to inactivate signal from contaminant nucleic acids. Application of heat may be used in combination with any other method to remove contaminating nucleic acids, as described herein. After heating, solutions may be cooled (often, rapidly cooled) to a lower temperature such as their storage temperature, making it unlikely for a single strand to be able to find its complementary strand at the low concentrations at which contaminant nucleic acids are present. The single stranded DNA or mispaired dsDNA fragments may not be efficiently converted into molecules that can be amplified or sequenced, thereby reducing their concentration in the final library. In some cases, heating can occur at a temperature of about or at least about 30, 35, 40, 45, 50, 55, 60, 65, 70, 75, 80, 85, 90, 91, 92, 93, 94, 95, 96, 97, 98, 99, 100, 110, 120, 130, or 140° C.

In some cases, heating can occur for a duration of about or at least about 1, 5, 10, 15, 20, 30, 35, 40, 50, or 55 seconds; about or at least about 1, 5, 10, 15, 20, 30, 40, or 50 minutes; about or at least about 1, 2, 3, 4, 5, 6, 7, 8, 9, 10, 11, 12, 13, 14, 15, 16, 17, 18, 19, 20, 21, 22, or 23 hours; or about or at least about 1, 2, 3, 4, 5, 6, 7, 8, 9, or 10 days.

In some cases, heated solutions (e.g., nucleic acid analysis buffer) or reagents are cooled to a temperature of about or at least about −80, −50, −40, −30, −10, −5, 0, 5, 10, 20, 30, 35, 36, 37, or 40° C. or room temperature. In some cases, heated solutions or reagents are cooled to a temperature of up to about −80, −50, −40, −30, −20, −15, −10, −5, 0, 1, 2, 3, 4, 5, 10, 15, 20, 25, 30, 35, 36, 37, 38, 39, or 40° C. or room temperature.

In some cases, one or more additives may be added prior to or during heating to modulate nucleic acid melting temperature, boiling point, and/or pH. For example, an additive may be a salt such as a magnesium or sodium containing salt (e.g., $MgCl_2$, NaCl) or a buffering agent.

In some cases provided herein, decontaminated buffer or reagent may be used to clean surfaces or labware (e.g., benchtop, counter, fume hood, table, glassware, plastic, tube, Falcon tube, Eppendorf tube, pipette tip, pipette, syringe, spatula, needle, plate, well, instrument, glove, weighing boat, weighing paper, column, container). In some cases, surfaces or labware can be rinsed with a buffer or water that has been heated, or filled with a buffer or water, heated, and dried.

In some cases, an approach other than heating may be used to inactivate the contaminating nucleic acids in a reagent or nucleic acid analysis buffer. Such approach may be performed alone or in combination with heating. Examples of such approach may include use of a chemical denaturant such as an acid, base, organic solvent, cross-linking reagent, chaotropic agent, and/or disulfide bond-reducing agent. Generally, heating a reagent or nucleic acid analysis buffer may melt or denature some or all double stranded DNA (dsDNA) contaminant fragments present in the reagent or buffer and convert them into single stranded DNA (ssDNA). Upon sufficient heating, nucleic acid may be degraded, thereby inactivating the nucleic acid.

Detection

The methods, composition and kits disclosed herein may be used to determine if a nucleic acid detected in a clinical sample is truly present in the clinical sample or is an environmental contaminant or a reagent contaminant. The methods provided herein may also be used to detect, diagnose, or prognose infections or diseases in patient samples, such as human blood samples. The methods may be used to detect rare microbial nucleic acid fragments in samples that are predominantly made up of human nucleic acids. For example, cell-free DNA (cfDNA) in blood consists mostly of DNA fragments derived from the host but also contains a small amount of fragments from microbes in the body.

Extraction of cfDNA followed by deep sequencing (e.g., next-generation sequencing or NGS) can generate millions or billions of sequence reads that can be mapped against host and non-host genome databases. Likewise, the methods can also be used to detect rare populations of circulating or cell-free RNA from a particular organ. For samples in which the non-host reads are a very small proportion of the total, the methods provided herein can improve the sensitivity and specificity of the assay, which would otherwise be compromised by a lack of internal normalization standards against which to compare different target nucleic acids (e.g., derived from different microbes or organism) or to track different samples or reagents. In addition, the methods can be used in settings where the target nucleic acids make up a larger portion of the total population of nucleic acids.

In some aspects, in the context of the present disclosure is any method that allows for detection and/or identification of a specific target nucleic acid, wherein the term "detection" also comprises the quantitative determination of a nucleic acid. In some aspects, the detection and/or identification may be based on specific amplification, for example, by the amplification of a specific DNA fragment using oligonucleotide primers specific for said DNA fragment in the polymerase chain reaction (PCR). In some aspects, the detection and/or identification may be based immunoassays.

In some aspects, detection may be a quantitative, semi-quantitative or non-quantitative observation and may be based on a comparison with one or more control samples. In some embodiments and without limitation, the step of detecting a pathogen or contaminant can comprises using PCR, real-time PCR, lectins, multiplex PCR, PCR methods disclosed herein, simple diffusion, lateral diffusion, immunological detection, lateral flow, or flow through methods to detect the presence of the pathogen or contaminant in a sample or dilutions of a dilution series. By way of illustration and not limitation, in particular embodiments possible detecting methods include or use the subject matter disclosed in any of U.S. Pat. Nos. 6,483,303, 6,597,176, 6,607,922, 6,927,570, and 7,323,139.

The skilled person is well aware of how to design oligonucleotide primers which specifically hybridize to the nucleic acid of interest (target nucleic acids). In some aspects, the detection and/or identification may also be achieved without amplification, for example, by sequencing the nucleic acid to be analyzed or by sequence specific hybridization, for example, in the context of a microarray experiment. Sequencing techniques and microarray based analysis are well known procedures in the field. In some aspects, detection after PCR can be performed by, for example, electrophoresis, fluorescent probe method, capillary electrophoresis method, or quantitative PCR method.

As described herein, in some embodiments, the kits, compositions and method described herein can utilize detection of target nucleic acids by detection of amplicons. In some embodiments, either direct or indirect detection of amplicon can be performed. In some embodiments, direct detection involves the incorporation of a label into the amplicon via, e.g., a labeled primer. In some embodiments, indirect detection involves incorporation of a label into, e.g., a hybridization probe. In some embodiments, for direct detection, the label(s) may be incorporated in at least four ways: (1) the primers comprise the label(s), for example attached to the base, a ribose, a phosphate, or to analogous structures in a nucleic acid analog; (2) modified nucleosides that are modified at either the base or the ribose (or to analogous structures in a nucleic acid analog) with the label(s); these label-modified nucleosides are then converted to the triphosphate form and are incorporated into the newly synthesized strand by a polymerase; (3) modified nucleotides are used that comprise a functional group that can be used to add a detectable label; or (4) modified primers are used that comprise a functional group that can be used to add a detectable label. In some embodiments, any of these methods result in a newly synthesized strand that comprises labels that can be directly detected.

In some embodiment, for indirect detection, a label may be incorporated into a hybridization probe using methods well known to one of skill in the art. In some embodiments, the label can be incorporated by attaching the label to a base, ribose, phosphate, or to analogous structures in a nucleic acid analog, or by synthesizing the hybridization probe using a modified nucleoside. In some embodiments, a modified strand of the amplicon or the hybridization probe can include a detection label. By "detection label" or "detectable label" herein is meant a moiety that allows detection. This may be a primary label or a secondary label.

Pathogens and Contaminants

The methods compositions and kits disclosed herein may be used to determine if a nucleic acid detected in a sample is truly present in the clinical sample or is an environmental contaminant or a reagent contaminant. An environmental contaminant or a reagent contaminant may be any nucleic acid or fragment thereof that is representative of any disease or condition disclosed herein. A contaminant can be a pathogen disclosed herein. A contaminant can be a microbe. The methods provided herein are particularly useful for determining the origins of for example, drug-resistant microbes, including multi-drug resistant microbes, or microbes that are not readily cultured or typically tested for.

The determination of the origin of a pathogen or contaminant may involve comparing a level or relative abundance of pathogen or contaminant nucleic acids of a sample to a level of pathogen or contaminant nucleic acids of dilutions of a dilution series (a first dilution of the sample and/or a second dilution of the sample) in order to determine if the quantity or level of pathogen or contaminant nucleic acids increase, decrease, is relatively the same or is not correlated. The level may be a qualitative or a quantitative level.

In some aspects, a target nucleic acid of a pathogen or contaminant can be a reagent based contaminant or pathogen when the quantity or level of a target nucleic acid in a first dilution is less than a quantity or level of a target nucleic acid in a second dilution. In some aspects, a second dilution is more dilute than a first dilution. In some aspects, a target nucleic acid of a pathogen or contaminant can be a sample based contaminant or pathogen when the quantity or level of a target nucleic acid in a first dilution is more than a quantity or level of a target nucleic acid in a second dilution. In some aspects, a target nucleic acid of a pathogen or contaminant can be an environmental contaminant or pathogen when the quantity or level of a target nucleic acid in a sample, first dilution and a second dilution is not correlated. Not correlated can refer to a lack of pattern among a dilution series. In some aspects, a target nucleic acid of a pathogen or contaminant can be an environmental contaminant or pathogen when the quantity or level of a target nucleic acid in a sample, first dilution and a second dilution is the same.

In some cases, in order to determine an origin of a pathogen or contaminant one or more of the following methods can be applied: (i) as described in Patent WO 2015070086 A1 the totality of the reads obtained by sequencing nucleic acids in a dilution series can be aligned against a curated host genome reference database, which can be from a human, dog, cat, primate or from any other host, including for example GenBank hg19 human reference sequences; (ii) a data processor for bioinformatics analysis can subtract or sequester the host sequences so that only non-host sequences, including pathogen-related sequences, can be further analyzed; (iii) a data processor can determine the presence of one or more pathogens or contaminant by aligning the non-host sequences to a curated microbial reference sequence database, including for example reference sequences from GenBank and Refseq; (iv) a statistical analysis framework can be applied to determine whether the presence of one or more pathogens is statistically significant; and/or (v) in some instances the data processor can quantify the amount of pathogen or contaminant present in each dilution of a dilution series. In some aspects, the data processor can quantify the amount of pathogen or contaminant present in each dilution based on the number of reads obtained for the pathogens or contaminants as compared to the number of reads obtained by control molecules spiked into the sample at a known concentration before sequencing.

In some embodiments, the methods and kits disclosed herein can detect an origin of a pathogen or infection or contaminant that is not detected or detectable by other methods, such as plate culturing or polymerase chain reaction (PCR). The methods generally may have a very high sensitivity, e.g., a sensitivity of greater than 80%, 85%, 90%, 95%, 99%, or 99.5%. The methods generally may have a very low false positive rate, e.g., a false positive rate of less than 10%, 9%, 8%, 7%, 6%, 5%, 4%, 3%, 2%, 1%, 0.1%, 0.05%, 0.01%. In some embodiments, a false positive rate of detecting pathogen nucleic acids can be less than 10%, 9%, 8%, 7%, 6%, 5%, 4%, 3%, 2%, 1%, 0.1%, 0.05%, 0.01%. In some embodiments, a false positive rate of detecting contaminant nucleic acids can be less than 10%, 9%, 8%, 7%, 6%, 5%, 4%, 3%, 2%, 1%, 0.1%, 0.05%, 0.01%.

The methods provided herein may provide high specificity, high sensitivity, high positive predictive value, and/or low negative predictive value. The methods provided herein may provide a specificity (or negative percent agreement) and/or sensitivity (or positive percent agreement) that is at least 70%, 75%, 80%, 85%, 86%, 87%, 88%, 89%, 90%, 91%, 92%, 93%, 94%, 95%, 96%, 97%, 98%, 99%, or more. In some cases, the nominal specificity is greater than or equal to 70%. The nominal negative predictive value (NPV) is greater than or equal to 95%. In some cases, the NPV is at least 95%, 95.5%, 96%, 96.5%, 97%, 97.5%, 98%, 98.5%, 99%, 99.5% or more.

In some cases, a sample, environment, or reagent can be identified as being the origin of a pathogen or contaminant with an accuracy of greater than 75%, 80%, 85%, 86%, 87%, 88%, 89%, 90%, 91%, 92%, 93%, 94%, 95%, 96%, 97%, 98%, 99%, 99.5% or more. In some cases, a sample, environment, or reagent is identified as being the origin of a pathogen or contaminant with a sensitivity of greater than 95%. In some cases, a sample, environment, or reagent can be identified as being the origin of a pathogen or contaminant with a specificity of greater than 95%. In some cases, a sample, environment, or reagent can be identified as being the origin of a pathogen or contaminant with a sensitivity of greater than 95% and a specificity of greater than 95%. In some cases, the accuracy can be calculated using a trained algorithm. In some cases, a method described herein has a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

In some embodiments, when classifying an origin of a pathogen or contaminant, there can typically be four possible outcomes from a binary classifier. If the outcome from a prediction is p (positive) and the actual value is also p, then it is called a true positive (TP); however, if the actual value is n (negative) then it is said to be a false positive (FP). Conversely, a true negative has occurred when both the prediction outcome and the actual value are n, and false negative is when the prediction outcome is n while the actual value is p. For a test that determines the origin of a contaminant or pathogen, a false positive in this case may occur when a sample tests positive for a pathogen or contaminant, but actually does not have the contaminant or pathogen (the pathogen or contaminant was introduced by a reagent or the environment). A false negative, on the other hand, may occur when the sample actually does have a pathogen, but tests negative for such a pathogen.

In some cases, the results of the sequencing analysis of the methods described herein provide a statistical confidence level that a given result is correct. In some cases, such statistical confidence level can be above 85%, 90%, 91%, 92%, 93%, 94%, 95%, 96%, 97%, 98%, 99% or 99.5%.

Detect, Monitor, Diagnose, Prognose, Treat, or Prevent

The methods provided herein may be used to detect, monitor, diagnose, prognose, treat, or prevent a large variety of diseases and disorders. In particular, the methods may be used to detect one or more target nucleic acid derived from a pathogen associated with an infectious disease or disorder. Exemplary diseases and disorders include any disease or disorder disclosed herein.

The detection of pathogen or organ nucleic acids may involve comparing a level of pathogen or organ nucleic acids with a control or reference value in order to determine the presence or absence of the pathogen or organ nucleic acids and/or the quantity of pathogen or organ nucleic acids. The level may be a qualitative or a quantitative level. In some cases, the control or reference value is a predetermined absolute value indicating the presence or absence of the cell-free pathogen nucleic acids or cell-free organ-derived nucleic acids. For example, detecting a level of cell-free pathogen nucleic acids above the control value may indicate the presence of the pathogen or of an infection, while a level below the control value may indicate the absence of the pathogen or of an infection. The control value may be a value obtained by analyzing cell-free nucleic acid levels of a subject without an infection; in some cases, the control value may be a positive control value and may be obtained by analyzing cell-free nucleic acids from a subject with a particular infection, or with a particular infection of a specific organ.

In some cases, in order to determine whether an infection is present or not—and often to obtain a result with precision—one or more of the following methods can be applied: (i) as described in Patent WO 2015070086 A1 the totality of the reads obtained by sequencing can be aligned against a curated host genome reference database, which can be from a human, dog, cat, primate or from any other host, including for example GenBank hg19 human reference sequences; (ii) a data processor for bioinformatics analysis can subtract or sequester the host sequences so that only non-host sequences, including pathogen-related sequences, can be further analyzed; (iii) a data processor can determine the presence of one or more pathogens by aligning the non-host sequences to a curated microbial reference sequence database, including for example reference sequences from GenBank and Refseq; (iv) a statistical analysis framework can be applied to determine whether the presence of one or more pathogens is statistically significant; and/or (v) in some instances the data processor can quantify the amount of pathogen present based on the number of reads obtained for the pathogens as compared to the number of reads obtained by control molecules spiked into the sample at a known concentration before sequencing.

The control value may be a level of cell-free pathogen or organ-specific nucleic acids obtained from the subject (e.g., subject with an infection or suspected of having an infection) at a different time point, such as a time point prior to the test time point. In such cases, comparison of the level at different time points may indicate the presence of infection, presence of infection in a particular organ, improved infection, or worsening infection. For example, an increase of cell-free pathogen nucleic acids by a certain amount over time may indicate the presence of infection or of a worsening infection, e.g., an increase of pathogen or organ-specific cell-free nucleic acids of at least 5%, 10%, 20%, 25%, 30%, 50%, 75%, 100%, 200%, 300%, or 400% compared to an original value may indicate the presence of infection, or of a worsening infection. In other examples, a reduction of pathogen or organ-specific cell-free nucleic acids by at least 5%, 10%, 20%, 25%, 30%, 50%, 75%, 100%, 200%, 300%, or 400% compared to an original value may indicate the absence of infection, or of an improved infection. Often, such measurements may be taken over a particular time period, such as weekly, or monthly.

Control or reference values may be measured as a concentration or as a number of sequencing reads. Control or reference values may be pathogen-dependent. For example, a control value for *Escherichia coli* may be different than a control value for *Mycoplasma hominis*. A database of levels or control values may be generated based on samples obtained from one or more subjects, for one or more pathogens, for one or more organs, and/or for one or more time points. Recommended treatment options may be based on different threshold levels. For instance, a low level may signify infection but treatment may not be necessary; a moderate level may lead to antibiotic treatment; and a high level may require immediate or serious intervention.

The methods provided herein may enable the generation of sequencing data with high efficiency, high accuracy, and/or high sensitivity. In some embodiments, the methods and kits disclosed herein can detect a pathogen or infection or contaminant that is not detected or detectable by other methods, such as plate culturing or polymerase chain reaction (PCR). The methods generally may have a very high sensitivity, e.g., a sensitivity of greater than 80%, 85%, 90%, 95%, 99%, or 99.5%. The methods generally may have a very low false positive rate, e.g., a false positive rate of less than 5%, 4%, 3%, 2%, 1%, 0.1%, 0.05%, 0.01%.

The methods provided herein may provide high specificity, high sensitivity, high positive predictive value, and/or low negative predictive value. The methods provided herein may provide a specificity (or negative percent agreement) and/or sensitivity (or positive percent agreement) that is at least 70%, 75%, 80%, 85%, 86%, 87%, 88%, 89%, 90%, 91%, 92%, 93%, 94%, 95%, 96%, 97%, 98%, 99%, or more. In some cases, the nominal specificity is greater than or equal to 70%. The nominal negative predictive value (NPV) is greater than or equal to 95%. In some cases, the NPV is at least 95%, 95.5%, 96%, 96.5%, 97%, 97.5%, 98%, 98.5%, 99%, 99.5% or more.

Sensitivity, Positive Percent Agreement (PPA), or true positive rate (TPR) may refer to an equation of TP/(TP+FN) or TP/(total number of infected subjects), where TP is the number of true positives and FN is the number of false negatives. When calculating the denominator for the previous equations, the value can reflect the total number of infection results based on a particular independent method of detecting infection (e.g., blood culture or PCR).

Specificity, Negative Percent Agreement or true negative rate may refer to an equation such as TN/(TN+FP) or TN/(total number of uninfected subjects), where TN is true negative and FP is false positive. When calculating the denominator for the previous equations, the value can reflect the total number of actual "non-infections" as determined by an independent method of detecting infection (e.g., blood culture or PCR).

In some cases, the sample is identified as infected with an accuracy of greater than 75%, 80%, 85%, 86%, 87%, 88%, 89%, 90%, 91%, 92%, 93%, 94%, 95%, 96%, 97%, 98%, 99%, 99.5% or more. In some cases, the sample is identified as infected with a sensitivity of greater than 95%. In some cases, the sample is identified as infected with a specificity of greater than 95%. In some cases, the sample is identified as infected with a sensitivity of greater than 95% and a specificity of greater than 95%. In some cases, the accuracy is calculated using a trained algorithm. The diagnosis accuracy as used herein includes specificity, sensitivity, positive predictive value, negative predictive value, and/or false discovery rate. In some cases, a method described herein has a specificity or sensitivity of greater than 70%, 75%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 95%, 95.5%, 96%, 96.5%, 97%, 97.5%, 98%, 98.5%, 99%, 99.5% or more.

When classifying a sample for diagnosis of infection, there are typically four possible outcomes from a binary classifier. If the outcome from a prediction is p and the actual value is also p, then it is called a true positive (TP); however, if the actual value is n then it is said to be a false positive (FP). Conversely, a true negative has occurred when both the prediction outcome and the actual value are n, and false negative is when the prediction outcome is n while the actual value is p. For a test that detect a disease or disorder such an infection, a false positive in this case may occur when the subject tests positive, but actually does not have the infection. A false negative, on the other hand, may occur when the subject actually does have an infection but tests negative for such infection.

The positive predictive value (PPV), or precision rate, or post-test probability of disease, is the proportion of patients with positive test results who are correctly diagnosed. It may be calculated by applying the following equation: PPV=TP/(TP+FP). The PPV may reflect the probability that a positive test reflects the underlying condition being tested for. Its value does however may depend on the prevalence of the disease, which may vary. The Negative Predictive Value (NPV) can be calculated by the following equation: TN/(TN+FN). The negative predictive value may be the proportion of patients with negative test results who are correctly diagnosed. PPV and NPV measurements can be derived using appropriate disease prevalence estimates.

In some cases, the results of the sequencing analysis of the methods described herein provide a statistical confidence level that a given diagnosis is correct. In some cases, such statistical confidence level is above 85%, 90%, 91%, 92%, 93%, 94%, 95%, 96%, 97%, 98%, 99% or 99.5%.

Monitoring and Treating

The methods may include monitoring whether a subject has an infection over time. For example, samples may be collected serially at various times in order to determine the presence or absence of an infection. In other examples, the methods may include monitoring the course of an infection over time. In such cases, samples may be collected serially at various time points during an infection or illness; in some cases, the serially-collected samples are compared to each other to determine whether the infection is improving or worsening.

The methods provided herein include methods of treating a subject, e.g., a subject with an infection or suspected of having an infection. The treatment may reduce, prevent or eliminate an infection in the subject. In some cases, the treatment may reduce, prevent or eliminate infection and/or inflammation.

The treatment may involve administering a drug or other therapy to reduce or eliminate the inflammation and/or the infection. In some cases, the subject is treated prophylactically with a drug, e.g., to prevent development of an infection or inflammation.

Any therapy (including a drug) to improve or reduce the symptoms of an infection or inflammation may be administered to the subject. Exemplary drugs include but are not limited to antibiotics, antiviral medication, ampicillin, sulbactam, penicillin, vancomycin, gentamycin, aminoglycoside, clindamycin, cephalosporin, metronidazole, timentin, ticarcillin, clavulanic acid, cefoxitin, antiretroviral drugs (e.g., highly active antiretroviral therapy (HAART), reverse transcriptase inhibitors, nucleoside/nucleotide reverse transcriptase inhibitors (NRTIs), Non-nucleoside RT inhibitors, and/or protease inhibitors), antibody-drug conjugates, and immunoglobulins.

The methods may include methods of adjusting a therapeutic regimen. For example, the subject may have a known infection and may have been administered a drug to treat the infection. The methods provided herein may be used to track or monitor the efficacy of the drug treatment. In some cases, the therapeutic regimen may be adjusted, depending on the results of such monitoring. For example, if the methods provided herein indicate that an infection is not improving as a result of the drug treatment, the therapeutic regimen may be adjusted by changing the type of drug or treatment given to the patient, discontinuing use of the previous drug, continuing use of the drug, increasing the dose of a drug treatment, or adding a new drug or other treatment to the subject's therapeutic regimen. In some cases, the therapeutic regimen may involve a particular procedure. Likewise, if the methods indicate than an infection is improving or resolved, the adjusting may involve reducing or discontinuing the drug treatment.

In some cases, when a method described herein gives a negative test result (e.g., no pathogen is detected), a method can be repeated serially over time to monitor pathogen nucleic acids in a subject. In some cases, the RNA-Seq assay is also repeated serially over time following a negative pathogen test result or negative RNA-Seq result.

In some cases, when a method described herein gives a positive test result (e.g., detection of a pathogen), then a therapeutic regimen can be administered to the subject. A therapeutic regimen can include, but is not limited to, drug administration, antibiotic administration, or antiviral administration.

In some cases, when a method described herein gives a positive test result, a method or test can be repeated serially over time to monitor the course of infection. For example, a therapeutic regimen can be adjusted depending on upward or downward course of infection. In other cases, no therapeutic regimen may be conducted initially; for example, the infection may be monitored with a "watchful waiting" or "watch and wait" approach to see if the infection clears up without additional medical intervention. In some cases, when a method described herein gives a positive test result, a drug can be administered, and the course of infection can be monitored to detect how well the drug is working or when to stop drug treatment. In some cases, the therapy can be altered as needed.

Computer Control Systems

Figure 7:
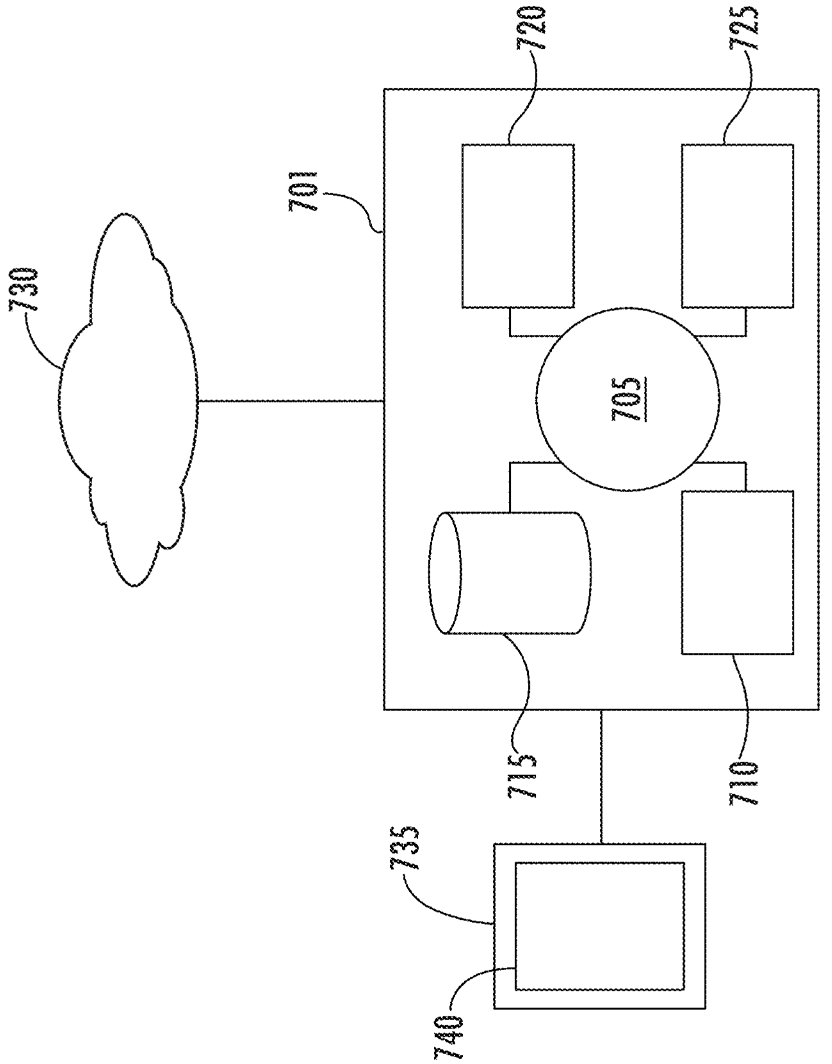
FIG. 7 shows a computer control system that is programmed or otherwise configured to implement methods provided herein.

The present disclosure provides computer control systems that are programmed to implement methods of the disclosure. FIG. 7 shows a computer system 701 that is programmed or otherwise configured to implement methods of the present disclosure.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, an output of a report, which may include a diagnosis of a subject or a therapeutic intervention for the subject. Examples of UI's include, without limitation, a graphical user interface (GUI) and web-based user interface. The analysis can be provided as a report. The report may be provided to a subject, to a healthcare professional, a lab-worker, or other individual.

Methods and systems of the present disclosure can be implemented by way of one or more algorithms. An algorithm can be implemented by way of software upon execution by the central processing unit 705. The algorithm can, for example, facilitate the enrichment, sequencing and/or detection of pathogen or other target nucleic acids.

Information about a patient or subject can be entered into a computer system, for example, patient background, patient medical history, or medical scans. The computer system can be used to analyze results from a method described herein, report results to a patient or doctor, or come up with a treatment plan.

As used throughout the specification herein, the term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

As used herein, the term "or" is used to refer to a nonexclusive or, such as "A or B" includes "A but not B," "B but not A," and "A and B," unless otherwise indicated.

EXAMPLES

Example 1: Diagnosis by a Cell-Free DNA Sequencing Assay

A cell-free plasma sample can be prepared. Cell-free nucleic acid molecules can be extracted and DNA libraries for next-generation sequencing can be prepared as previously described (De Vlaminck I, Khush K K, Strehl C, et al. Temporal response of the human virome to immunosuppression and antiviral therapy. Cell 2013; 155(5): 1178-87; De Vlaminck I, Martin L, Kertesz M, et al. Noninvasive monitoring of infection and rejection after lung transplantation. Proceedings of the National Academy of Sciences of the United States of America 2015; 112(43): 13336-41; each of which is hereby incorporated by reference in its entirety). Sequencing can be performed on an Illumina NextSeq instrument and analyzed. Briefly, after removing low-quality reads, reads can be mapped to a human reference genome (e.g., hg19). Remaining reads can be mapped to a curated reference database of viral, bacterial, fungal, and other eukaryotic pathogens. Abundances of individual pathogens are expressed as genome copies per volume, an absolute measure of the amount of nucleic acid from a specific pathogen per 1 ml of plasma. Alternatively, abundances can be expressed as a number of sequence reads mapping to a specific pathogen per volume. Further analysis can be performed to identify sequences known to confer resistance.

Example 2: Next-Generation Sequencing (NGS) of Patient Plasma

Plasma sample can be spiked with a known concentration of synthetic DNA molecules prior to DNA extraction. DNA can be extracted using a modified magnetic bead-based method (Omega Biotek, Norcross, Ga.). NGS libraries can be constructed using a modified library preparation kit (Ovation® Ultralow Library System V2, NuGEN, San Carlos, Calif.). Negative (containing buffer but no plasma) and positive (containing plasma from a healthy donor(s) plus known concentrations of sheared, laboratory-derived pathogen DNA) control samples can be processed alongside the sample. The libraries from all three DNA sample types can be multiplexed and sequenced on an Illumina NextSeq using a 75-cycle, single-end, dual-index sequencing kit.

Pathogen reads can be quantified from NGS read sets. Briefly, after low quality reads are discarded, human reads are removed by aligning to a human reference sequence (e.g., hg19). Synthetic spike-in reads are identified by aligning to the database of the full spike-in sequences. The remaining reads are aligned to a curated database of over 8000 reference sequences of viruses, prokaryotes, and eukaryotes including fungi, protozoa, and parasites. Duplicate reads, assumed to be derived from PCR duplication or sequencing instrument error, are identified based on alignment and removed in a process we refer to as deduping. As a result of this process, we obtain the count of estimated unique or deduped reads mapping to a particular pathogen reference. Relative abundance of organisms is expressed as estimated deduped reads (EDR), or reads per million (RPM, normalized to total reads for the sample), or reads per volume of sample (MPM, microbes per microliter). MPM is a normalized quantity that calculates the estimated number of unique nucleic acid fragments represented for each organism in 1 microliter of plasma. This calculation is derived from the number of unique or deduped sequences detected for each organism in the sequencing data normalized to the deduped quantity of synthetic DNA spiked directly into plasma before the extraction of nucleic acids from plasma and detected in the same sequencing data set. See, for example, U.S. Pat. No. 9,976,181.

Example 3: Differentiation Between Sample Nucleic Acids and Environmental Contamination Nucleic Acids Using a Set of Uniquely Indexed Replicates of the Undiluted Plasma Samples In this example, plasma samples were collected from a human subject suspected of having an infection. 6 mL of plasma sample was mixed with 60 μl of synthetic nucleic acids. The spiked plasma was mixed well. The synthetic nucleic acids were later used for normalizing the samples in order to account for variations in sample processing. The spiked plasma was processed to obtain cell-free plasma by centrifugation at 16,000 g's for 10 min. The spiked cell-free plasma was divided into 20 aliquots of 250 μL each.

The extraction process was performed using a modified magnetic bead-based method (Omega Biotek, Norcross, Ga.). Briefly, all 20 aliquots of previously spiked cell-free plasma samples (250 μl per aliquot) were mixed with 25 μL of a broad spectrum serine protease (Proteinase K), followed by the addition of 200 μL DCL Buffer to digest the protein fraction. Next, 450 μL of ACX Buffer with isopropanol was added to the reaction, followed by suspension of magnetic beads. The resulting extraction reaction was mixed well and incubated for 10 minutes with constant shaking. The magnetic beads were then pelleted on a magnet stand. The supernatant was removed and the pelleted beads were subjected to several wash steps with buffers containing ethanol. In the final wash step, the pelleted magnetic beads were rinsed with 125 μL water. Finally, the pelleted magnetic beads were resuspended in 25 μL of elution buffer to elute the extracted nucleic acids.

The cfDNA samples were processed to prepare a sequencing library for sequencing the samples in a sequencer. Next Generation Sequencing (NGS) libraries were constructed for each sample using a library preparation kit (Ovation® Ultralow Library System V2, NuGEN, San Carlos, Calif.). The sequencing library can be dependent on the sequencer employed. For example, the cfDNA samples were attached with adapter sequences for binding to flow cells of an Illumina sequencer.

Figure 6A:
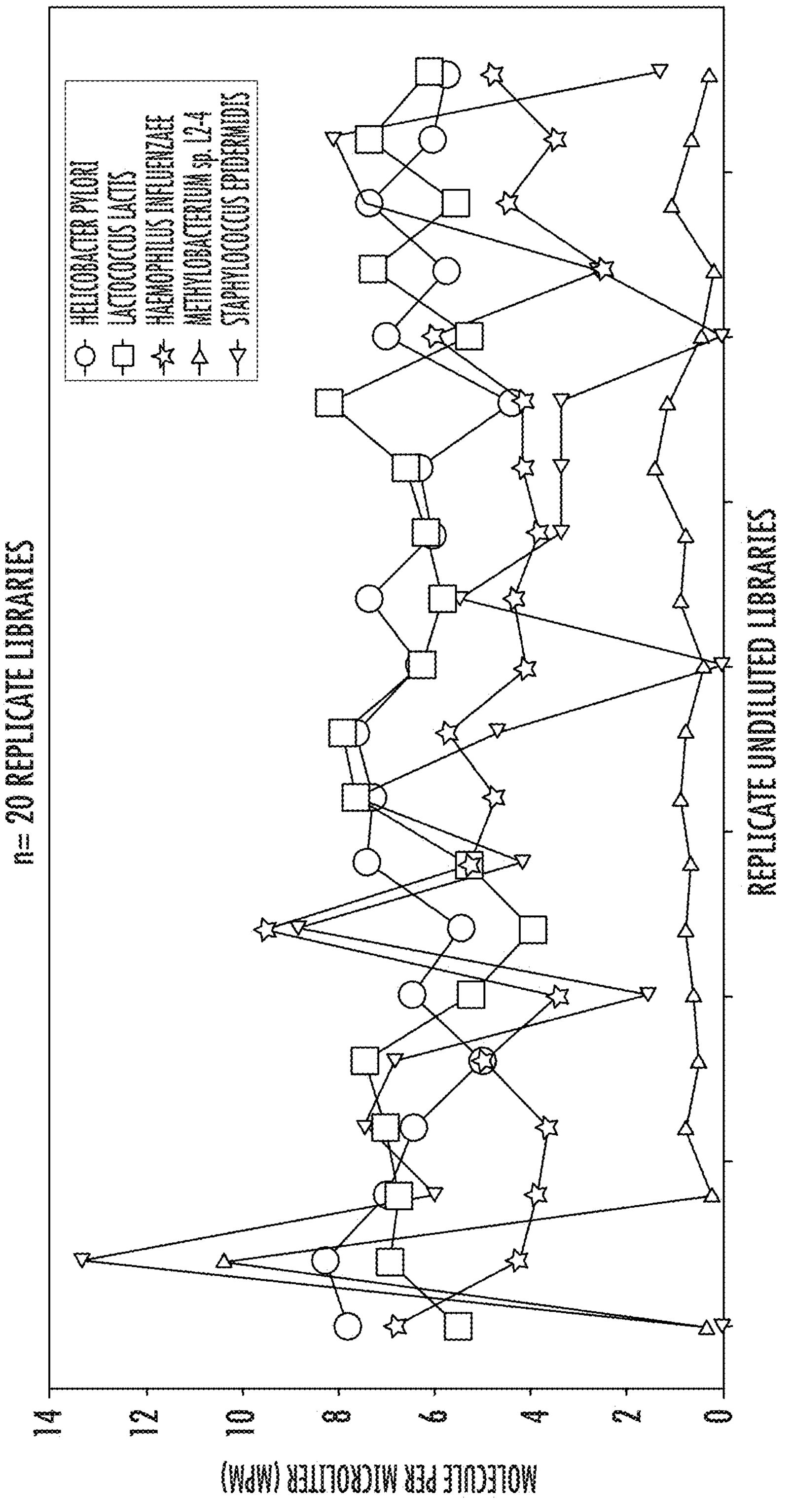
FIG. 6 (*a*) depicts inferred abundances of microbial pathogens across replicate processing of a sample.
Figure 6B:
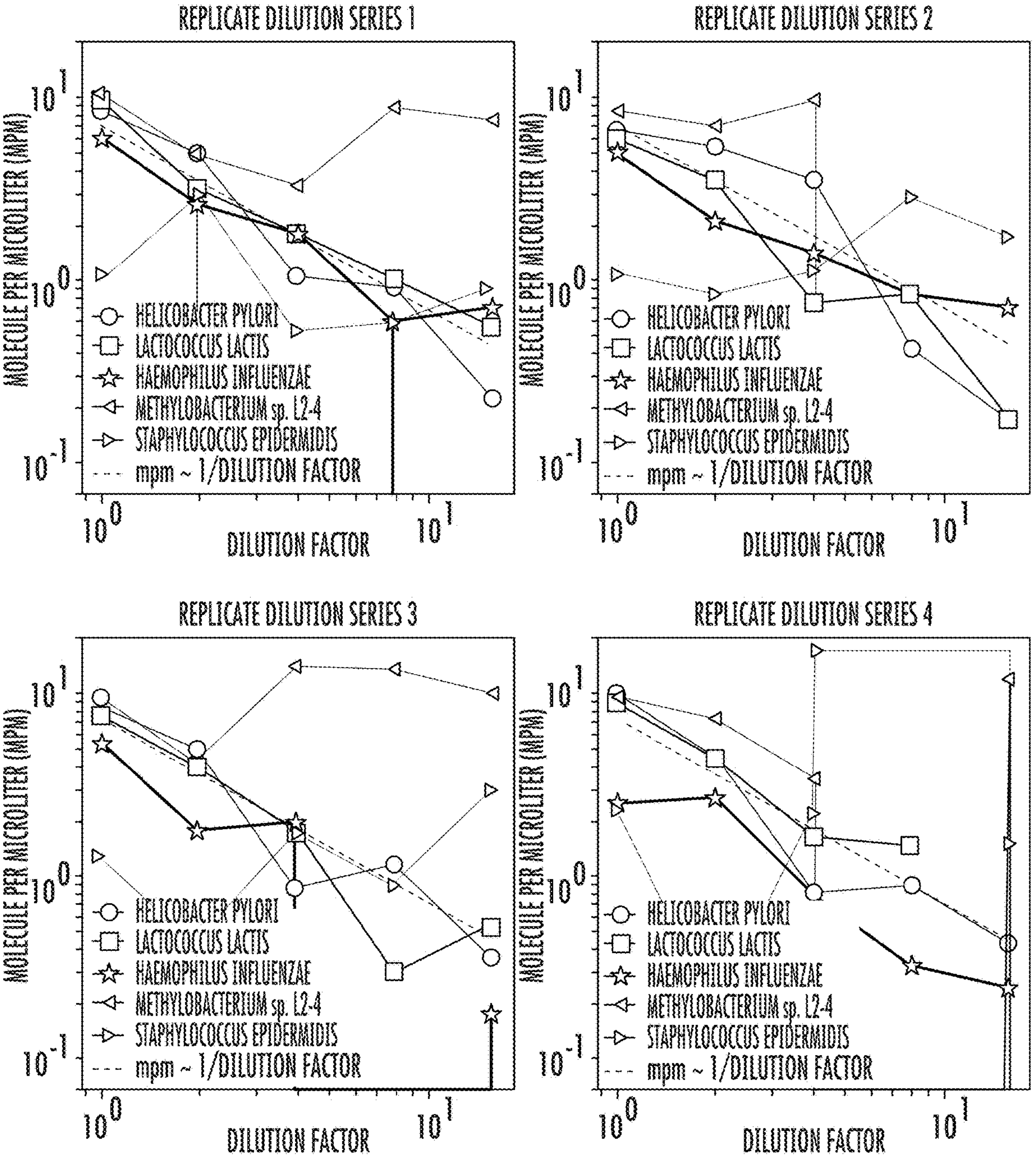

The cfDNA samples were sequenced to obtain sequence reads using a NextSeq 500. The sequence reads were mapped to a collection of reference genomes to identify host (e.g., human), synthetic sequences added to the original plasma and non-host (e.g., microbe) sequences. The host sequences were subtracted from further analysis. Based on the alignment of the microbial sequences to the collection of reference genomes, the presence of individual microbial species were determined. The abundance of the microbial species expressed as number of unique microbe-derived sequences per milliliter (MPM) was then determined. The replicative index was used to detect environmental contaminants by processing multiple replicates of the same undiluted sample and assessing changes in the signal of the microbial sequences. The environmental contaminants were distinguished from the pathogens originally present in the plasma sample by the normality of the distribution of MPM values for each detected pathogen within the population of all the replicates of the undiluted plasma sample. For example, FIG. 6(*a*) shows the sequential number of the replicate (replicate index) on the X-axis and the abundance (MPM) of microbial species on Y-axis to analyze the distribution of MPM values for the same pathogen among the population of all the replicates of the same undiluted plasma sample. As shown in FIG. 6(*a*), the MPM's for most abundant microbial species in a sample, such as *Helicobacter pylori*, *Lactococcus lactis*, and *Haemophilus influenza* show normally distributed values while *Methylobacterium* sp. and *Staphylococcus epidermidis* show erratic non-normal distribution of the MPM values. The likelihood that MPM values for the former group drawn from a normal distribution can be determined to be high and for the latter group, the values can be determined to be low. The former group of pathogen was thus determined to be present in the original plasma sample while the latter group of pathogens was determined to be introduced by environmental contamination during sample processing.

Example 4: Preparation of Sequencing Library

A sequencing library can be prepared by using the following procedure. About 10 μL of extracted and purified cfDNA sample is mixed with 5 μL of end repair solution (Ovation® Ultralow Library System End-repair master mix). Adapter ligation follows the-repair step by adding 6 μL of a unique adapter solution from a single well on the Ligation Adapter Plate (L2 in Ovation® Ultralow Library System v2). Each member of the dilution series receives their unique adapter solution from a different well on the Ligation Adapter Plate to provide for unique indexing of each dilution. Next, 9 μL of Ligation Master Mix is added to each library reaction. After the ligation step, nuclease-free water, and Agencourt® RNAClean® XP magnetic beads (Beckman Coulter, IN) are added to each member of the dilution series samples to precipitate nucleic acids, followed by ethanol wash, elution of the nucleic acids and collection of 35 μL of eluted fractions. The samples are further processed by adding 10 μL of Amplification Master Mix to each member of dilution series, followed by an amplification and post-amplification purification washing process. After the final wash, the magnetic beads are resuspended in 50 μL elution buffer, and purified library is collected.

Example 5: Differentiation Between Sample Nucleic Acids and Environmental Contamination Nucleic Acids Using an Indexed Dilution Series In this example, plasma samples were collected from human subjects. Samples were processed in parallel and in an identical manner, but this example describes in detail the processing of just one of the samples. The first sample was divided into a series in order to generate a dilution series. In this example, the input volume of plasma in a Member of Dilution Series (MDS) 1, 2, 3, and 4 was 500 μl, 250 μl, 125 μl and 62.5 μl, respectively. The dilution series was completed by adding sufficient 1×TE buffer to each MDS so that the total sample volume for each MDS was 500 μl. Following the addition of the TE buffer, the members of the dilution series were Plasma MDS 1 (undiluted sample, 1:1 dilution or dilution factor of 1.0), Plasma MDS 2 (1:2 dilution or dilution factor of 2.0), Plasma MDS 3 (1:4 dilution or dilution factor of 4.0), and Plasma MDS 4 (1:8 dilution or dilution factor of 8.0). 5 μl of synthetic nucleic acids were added to each Plasma MDS, bringing each Plasma MDS sample up to 505 μl. The spiked members of the dilution series were mixed well. The synthetic nucleic acids were later used for normalizing the signal in the samples in order to account for variations in sample processing.

The members of the series were each separately processed to extract cell-free DNA (cfDNA), thereby yielding cfDNA MDS 1, cfDNA MDS 2, cfDNA MDS 3, and cfDNA MDS 4 extracts. The cfDNA was extracted using a modified magnetic bead-based method (Omega Biotek, Norcross, Ga.), as described above for the undiluted cell-free plasma samples.

The cfDNA samples were processed to prepare a sequencing library for sequencing the samples in a sequencer. Next Generation Sequencing (NGS) libraries were constructed for each sample separately as described above, where each MDS library reaction receives their unique adapter solution from a different well on the Ligation Adapter Plate to provide for unique indexing of each dilution.

The cfDNA samples were sequenced to obtain sequence reads using a NextSeq sequencer. The sequence reads were mapped to a collection of reference genomes to identify host (e.g., human) and non-host (e.g., microbe) sequences. The host sequences were subtracted from further analysis. Based on the alignment of the microbial sequences to the collection of reference genomes, individual microbial species were determined. The abundance of the microbial species, expressed as number of unique molecules per microliter (MPM), was then determined.

The microbial sequences across the dilution series are analyzed to determine the nucleic acids derived from a sample (e.g., from plasma sample) and those derived from an environmental contamination (e.g., from laboratory environment, or introduced by the process handling or reagents). As shown in FIG. 6(*b*), the dilution factor of the MDS is plotted on X-axis and normalized abundance of microbial species (MPM) is plotted on Y-axis.

As described elsewhere herein (e.g., FIG. 4), when the abundance of a given microbial species across the dilution series is inversely correlated with the dilution factor, the given microbial species can be assigned as originating from the sample. On the contrary, when the abundance of a given microbial species across the dilution series is proportional to one minus the inverse of the dilution factor, the given microbial species can be assigned as originating from a diluent used for preparing the dilution series. When the abundance of a given microbial species across the dilution series is independent of the dilution factor, the given microbial species is assigned as originating from the environmental contamination or reagents (e.g., extraction buffers, spike-in stocks) used during the sample processing.

In this manner, the origin of detected pathogen nucleic acids was determined in the first patient samples. In the first patient, five pathogens were detected in the processed MDS samples: *Helicobacter pylori, Lactococcus lactis, Haemophilus influenzae, Methylobacterium* sp. and *Staphylococcus epidermidis*. However, only in the case of three out of these five detected pathogens (*Helicobacter pylori, Lactococcus lactis, Haemophilus influenzae*), we observed a correlation of their respective MPMs with the inverse of the dilution factor (FIG. 6(*b*)). The remaining two detected pathogens (*Methylobacterium* sp. and *Staphylococcus epidermidis*) showed no correlation with the dilution factor (FIG. 6(*b*)). It can then be concluded that the nucleic acids aligning to *Helicobacter pylori, Lactococcus lactis*, and *Haemophilus influenzae* originated from the patient because their MPMs were found to be inversely correlated with the dilution factor. Furthermore, the nucleic acids aligning to *Methylobacterium* sp. and *Staphylococcus epidermidis* were introduced by environmental contamination.

Example 6: Differentiation Between Sample Nucleic Acids and Environmental Contamination Nucleic Acids Using an Indexed Dilution Series and Single-Stranded Nucleic Acid Library Protocol The plasma or cell-free plasma samples and their dilutions were prepared as described above in Example 5.

As shown in FIG. 5, the members of the dilution series are each separately processed to extract cell-free DNA (cfDNA) from the plasma or cell-free plasma, thereby yielding cfDNA MDS 1, cfDNA MDS 2, cfDNA MDS 3, and cfDNA MDS 4. The cfDNA is extracted using a modified magnetic bead-based method (Omega Biotek, Norcross, Ga.), as described in Example 3 for the undiluted plasma or cell-free plasma samples. (Alternatively, a single plasma sample per patient is processed to extract cfDNA and the extracted cfDNA, rather than the starting plasma sample, is used to prepare a dilution series.)

The cfDNA MDS samples are processed to prepare a sequencing library for sequencing the samples in a sequencer. Next Generation Sequencing (NGS) libraries are constructed for each sample using a modified library preparation protocol previously published (Gansauge M T, and Meyer M, Nature Protocols (2013) 8(4): 737-748). (The sequencing library can be dependent on the sequencer employed. For example, the cfDNA samples can be attached with adapter sequences for binding to flow cells of an Illumina sequencer.)

As shown in FIG. 5, the cfDNA MDS 1 is attached with an adapter sequence, AA using a CircLigase II reaction. Similarly, the cfDNA MDS 2 is attached with an adapter sequence, AB; the cfDNA MDS 3 is attached with an adapter sequence, AC; and the cfDNA MDS 4 is attached with an adapter sequence, AD. Adapter sequences AA, AB, AC, and AD contain each a unique dilution index at their 5'-end to enable distinction between the nucleic acids derived from each MDS in the final sequencing data. Next, the ligation reaction from the members of the same dilution series are merged, and four different extension primers complementary to adapter sequences AA, AB, AC, and AD are hybridized to their respective ligated adapters, followed by primer extension reaction with Bst 2.0 polymerase or Klenow fragment to convert the nucleic acid templates to double-stranded forms (FIG. 5). The ends of the resulting double-stranded templates are polished by T4 DNA polymerase in case of Bst 2.0 polymerase-based primer extension. No end polishing is required, if Klenow fragment is used in the primer extension step. This is followed by second adapter is ligated by T4 DNA ligase. Finally, the resulting adapted templates are amplified with dual-indexing PCR in order to amplify the templates as well as introduce sample-specific indexes for sequencing that will allow the correct assignment of the nucleic acids in terms of their sample origin.

The cfDNA samples are sequenced to obtain sequence reads using a sequencer. The sequence reads are mapped to a collection of reference genomes to identify host (e.g., human) and non-host (e.g., microbe) sequences. The host sequences are subtracted from further analysis. Based on the alignment of the microbial sequences to the collection of reference genomes, individual microbial species are determined. The abundance of the microbial species, expressed as number of unique molecules of microbes per microliter (MPM), is then determined.

The origin of the detected pathogen nucleic acids (plasma sample vs. environmental contamination) can be determined as described above for Example 5.

Example 7: Negative Control Samples from Asymptomatic Patients or Synthetic Plasma A difficulty in pathogen identification using metagenomic sequencing of plasma or cell-free plasma can be due to the introduction of environmental contaminant DNA during sample handling and processing. Without an understanding of which taxa are typically present in environmental contaminant and at what abundances, the environmental contaminant signal may be confused with signal originating from the plasma in a clinical sample, leading to false positive identifications.

An approach to address this problem can be the concomitant sequencing (alongside clinical samples) of negative control samples. This can allow for a statistical characterization of the signal expected from environmental contaminant, which can then be deconvolved from the plasma-derived DNA in clinical samples. For many taxa, buffer-based negative controls (e.g., 1× TE buffer) play this role effectively. However, such negative control may have systematically lower or higher signals for certain taxa as compared to plasma samples. For these taxa, the buffer-based negative controls may not capture the conditions of plasma as they affect the efficiency of processing and eventual sequencing of genetic material accurately, and can expose a test to an increased risk for false positives or false negatives.

In this example, plasma from asymptomatic people (e.g., asymptomatic plasma) is used as a negative control in order to resolve this issue. The potential presence of a genuine, plasma-derived signal (e.g. due to commensals and potentially even infecting pathogens) in asymptomatic plasma makes it exceedingly difficult to use asymptomatic plasma as a negative control. First, the use of asymptomatic plasma can reduce the sensitivity of tests for the taxa that are present in the plasma-based negative control. Second, if the real signal is below the level necessary to trigger a significant call, it was so far very difficult to know for which taxa the sensitivity would be reduced.

In this example, a dilution series is used to determine the plasma-derived signal of a particular lot of asymptomatic plasma, following the steps outlined in the preceding examples. This asymptomatic plasma can then be used as a negative control with the knowledge that the sensitivity of the test will not be reduced for all taxa except those identified by the dilution method as derived from the asymptomatic plasma used as negative control. In order to expand the negative control to cover those remaining taxa, one can repeat the dilution series for additional asymptomatic plasmas until one has a set of asymptomatic plasma's with any plasma-derived signals found in disjoint sets of taxa.

The negative controls can then be one or more samples of asymptomatic plasma, where the subset of negative controls that are negative for a particular set of taxa is used to characterize the expected environmental contaminant levels of those taxa. In cases where an asymptomatic plasma has no plasma-derived signal, the asymptomatic plasma can be used directly as the negative control. In this case the dilution series can be used to verify that there is no loss in sensitivity for any taxa.

Another approach can be to use synthetic samples as negative controls with biochemical properties that mimic those of plasma in such a way that there are no biases or reduce bias across taxa in the efficiencies at which DNA molecules are processed and sequenced relative to true plasma. In this case the use of the dilution method to characterize which taxa are present in the synthetic samples prior to their use as negative controls can be used to rule out contamination with DNA of one or more taxa.

Example 8: Detection of Environmental Contamination by Use of Control Samples Environmental contamination introduced during sample processing can be a problem when trying to detect low magnitude signal such as pathogen cfDNA in plasma samples. To account for this type of contamination, control samples are processed in parallel with clinical samples. The control samples presumably collect the environmental contamination as efficiently as the clinical samples themselves.

Dilution series of each received clinical sample is generated with a diluent (e.g. asymptomatic plasma, healthy plasma, 1× TE, physiological solution etc.) and libraries from each dilution are prepared. Library of each dilution can have a unique index. For each clinical sample included in a batch, the same dilution series can be prepared to allow direct detection of environmental contamination. Detection can be performed in droplet synthesis conformation to reduce the adapter volume requirement.

Alternatively, a pre-ligation step can be introduced (for example, prior to adapter ligation) to introduce specific sequences to the ends of the nucleic acids (DNA). These sequences can be dilution-specific for each sample. The introduction of the adapter/index sequences can then be dependent on successful pre-attachment (ligation) of the dilution sequence. This approach can easily be introduced in the context of a ssDNA library protocol.

Example 9: Analytical Validation

Analytical validation of an assay can be performed to assess the performance of the assay to detect target nucleic acids. The results of the assay under analytical validation are compared to the ground truth of the presence of target nucleic acids in the samples used as part of the validation. Such ground truth can be provided by the established diagnostic techniques. For example, a new assay to detect infecting pathogens in human hosts will often be compared to the results obtained with blood culture using the same set of validation samples, provided that the new assay and blood culture share the same source of nucleic acid pool (e.g. intact pathogen cells or particles in blood). If that is not the case (e.g. pathogen detection through cell-free nucleic acid signal) the ground truth provided by blood culture will be potentially incomplete, and thus inflating the false positives of the new assay under the validation. Dilution series principles disclosed in this document provide means to track the origin of the detected nucleic acids to either the original sample or environmental contamination, and consequently enabling the ground truth of the sample independently of the established diagnostic technique.

A detection of a pathogen in a sample can be validated by the methods disclosed herein. (1) A dilution series of the original sample can be prepared or (2) a set of multiple undiluted replicates can be sequenced at a higher sequencing depth. If the initially detected pathogen signal originates in the original sample then the signal will decrease in (1) with the dilution factor while it should be constant in (2). If the initially detected pathogen signal is derived from the environment during sample processing then (1) should not result in pathogen signal that is correlated with the dilution factor and in (2), the signal should not be reproducible. In some cases, pathogen or pathogen nucleic acids derived from the environment can have an abundance that is relatively the same across a dilution series.

Analytical Specificity

Analytical specificity (the rate of having no non-endogenous calls) in clinical metagenomic testing can be influenced by a number of factors, including the ubiquitous environmental contamination (EC) of reagents and consumable surfaces with DNA fragments from a variety of microorganisms. Because the composition of endogenous microbial cfDNA species in plasma varies considerably from person to person, it is difficult to accurately assess analytical specificity when using a variety of different clinical samples.

Figure 9:
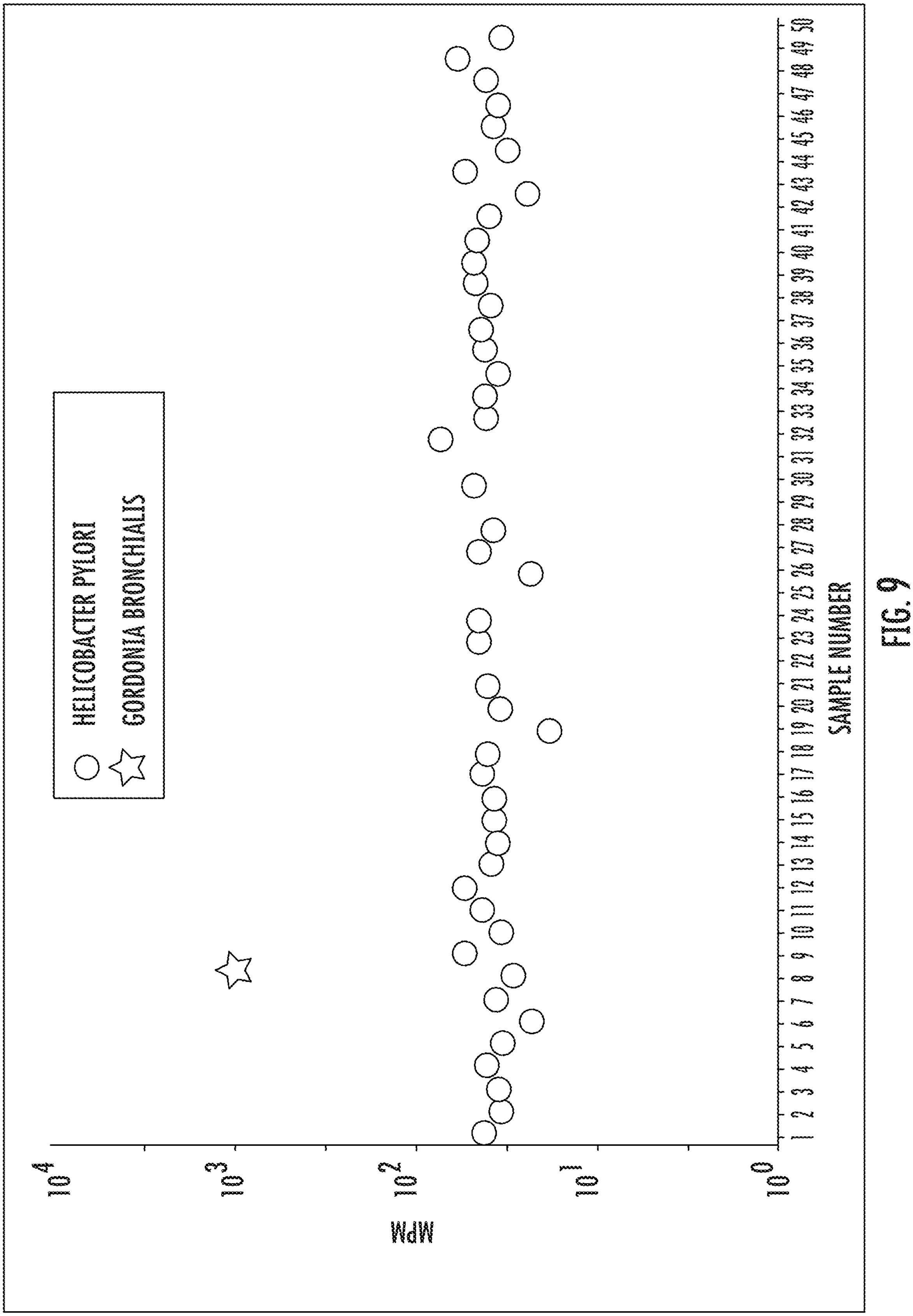
FIG. 9 is a graph showing data used to calculate analytical specificity. Repeated measurements of a single healthy plasma sample composed of eight different donors that had been characterized by a dilution series as described herein. The results from 50 replicate measurements taken across 9 days are shown. *H. pylori* cfDNA was known to be present in this sample, whereas other microorganisms were not, Reference is made to Example 9.

Therefore, we characterized the pathogens present in a single human plasma pool using a dilution series. We then assessed EC-related analytical specificity by processing replicate measurements of this human plasma pool. To this end, we first generated fifty 500 μl, aliquots of this human plasma pool, spiked with synthetic control molecules, and stored them at −80° C. until use. Subsequently, we processed them from plasma to sequencing libraries in batches of seven or eight samples over nine days (FIG. 9). Of the 50 replicates tested this way, microbial cfDNA from a taxon not inferred by the dilution series method was detected in only one replicate, from *Gordonia bronchialis* at 1,000 MPM, yielding an overall specificity of 98% (49 of 50 true negative samples; *Helicobacter pylori* cfDNA had been inferred via the dilution series method).

Example 10: Assay Control Manufacturing

Assay controls may play multiple essential roles in diagnostic assays. For example, negative assay controls can be used to statistically characterize the background or contamination signal originating from the process, and the positive assay controls can be used to assess test validity and assay performance when run alongside clinical samples. In infectious disease diagnostics utilizing biological samples (e.g. blood, plasma, urine, CSF, etc.), the positive assay control is often contrived by spiking a base biological sample obtained from a presumed healthy individual with an appropriate analyte (e.g. microbial proteins, nucleic acids, cell-free nucleic acids, cells/capsids etc.) from known microbial species or taxa. The assay is then validated or its performance confirmed when the analysis of such a positive assay control confirms the presence of the spiked microbes and no others. However, if (additional) microbes other than the spiked set are present in the base biological samples used in the preparation of the positive assay control (e.g. commensal or undetected infectious microbes in the presumed healthy donor of the base biological sample) and these are detected by the assay, this may lead to the (erroneous) conclusion that the assay has produced a false positive call. A dilution series of the base biological sample intended for the preparation of the positive assay control can therefore be performed prior to manufacturing the positive assay control and used to determine the presence of any endogenous material originating from commensal or infectious microbes in the base biological sample, allowing an operator to discount the detection of these microbes when detected in the positive assay control.

Figure 10A:
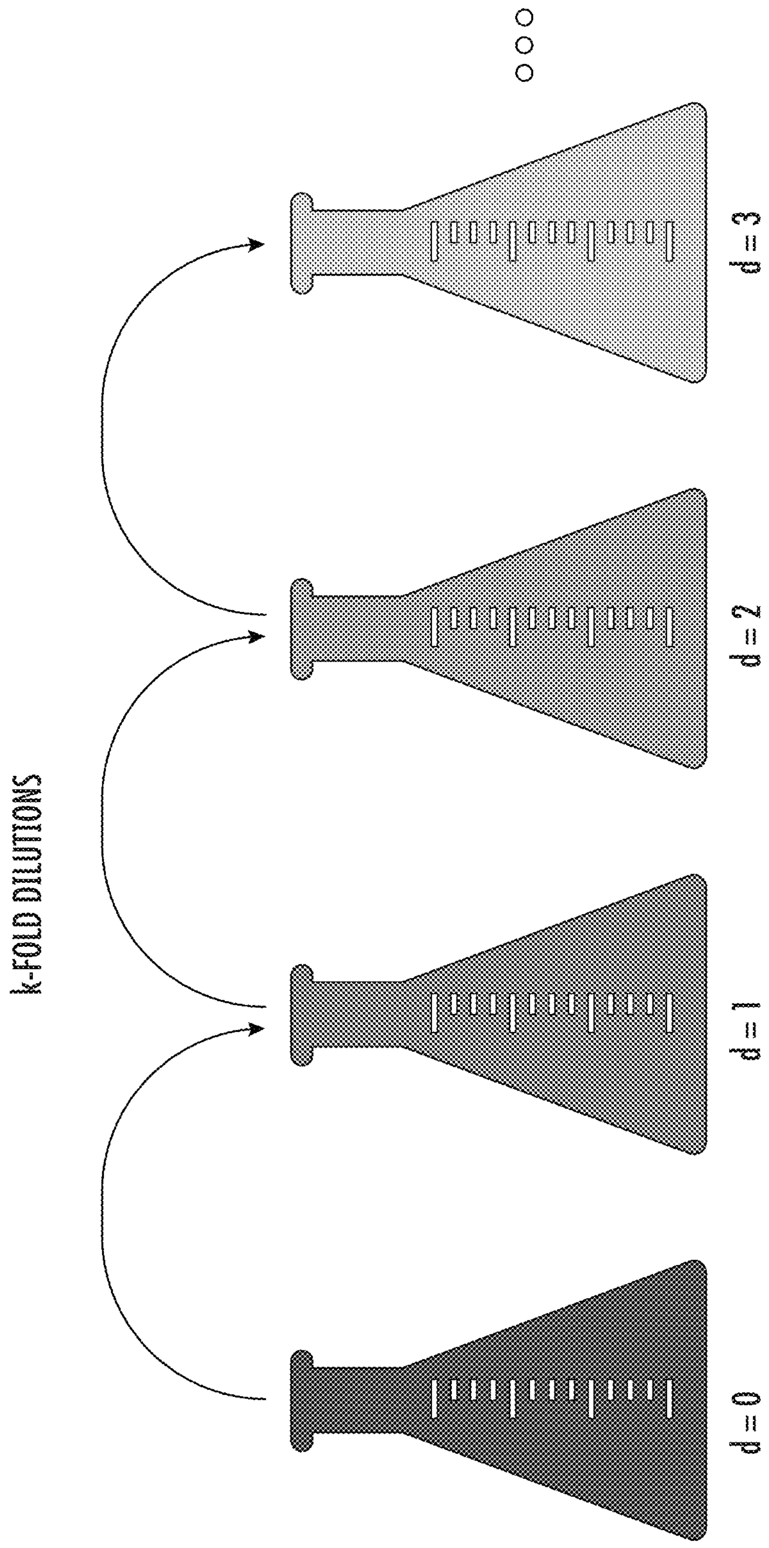
FIG. 10 (*a*) is a schematic representation of the process to generate a dilution series for Example 10.
Figure 10B:
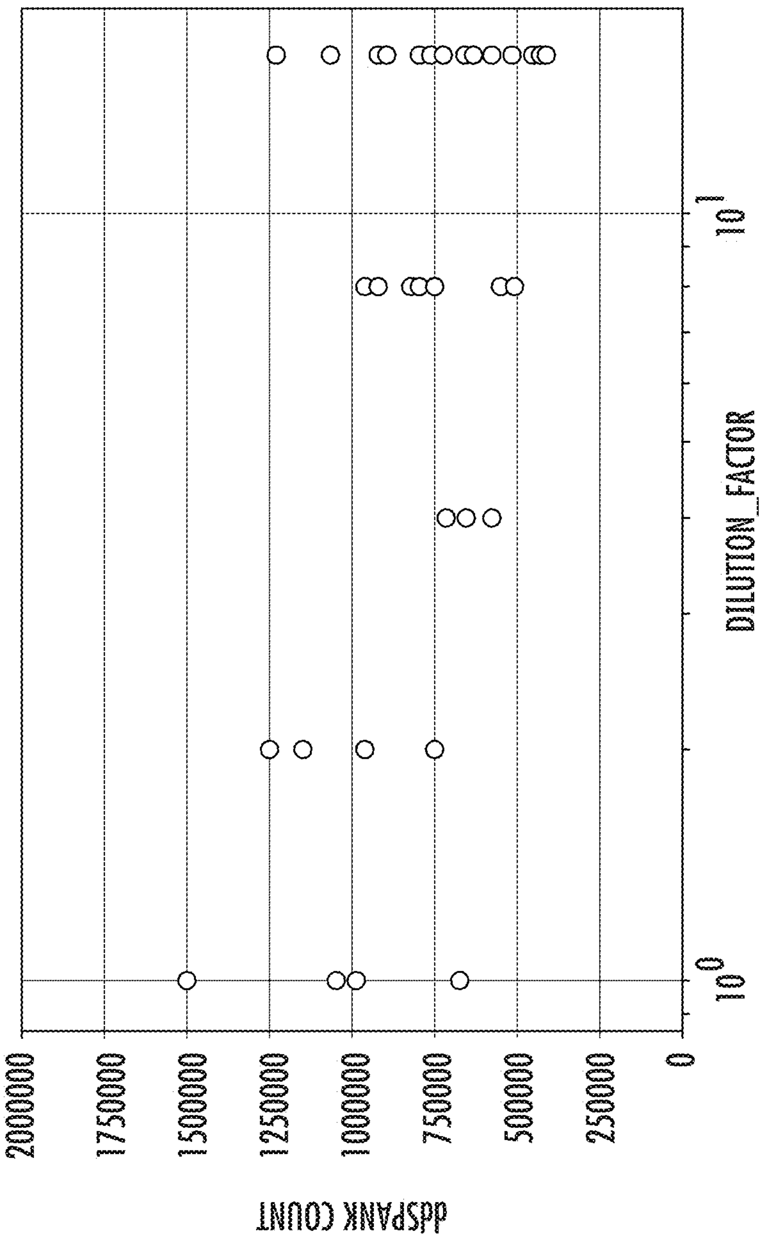
Figure 10C:
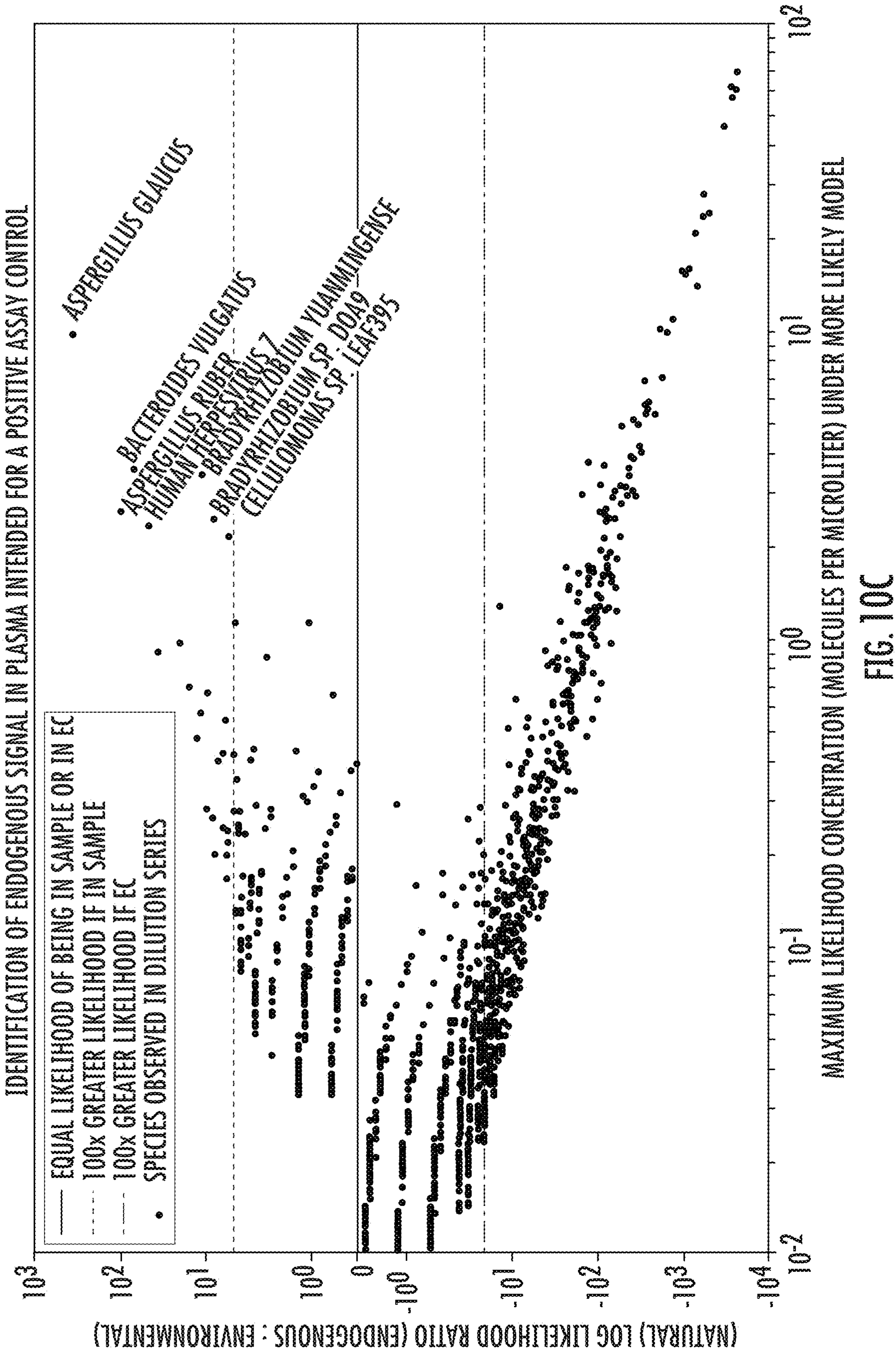
Figure 10D:
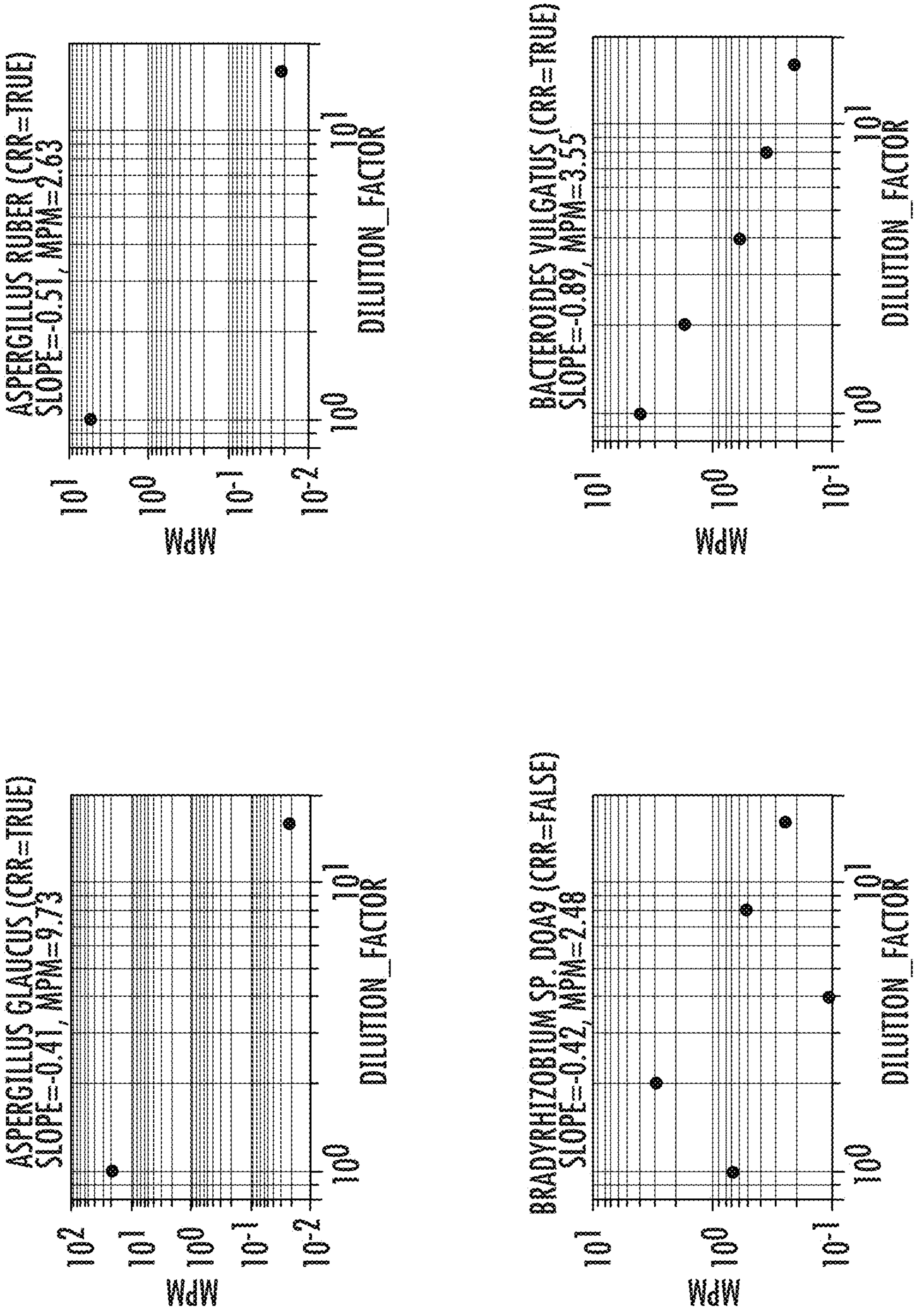
Figure 10E:
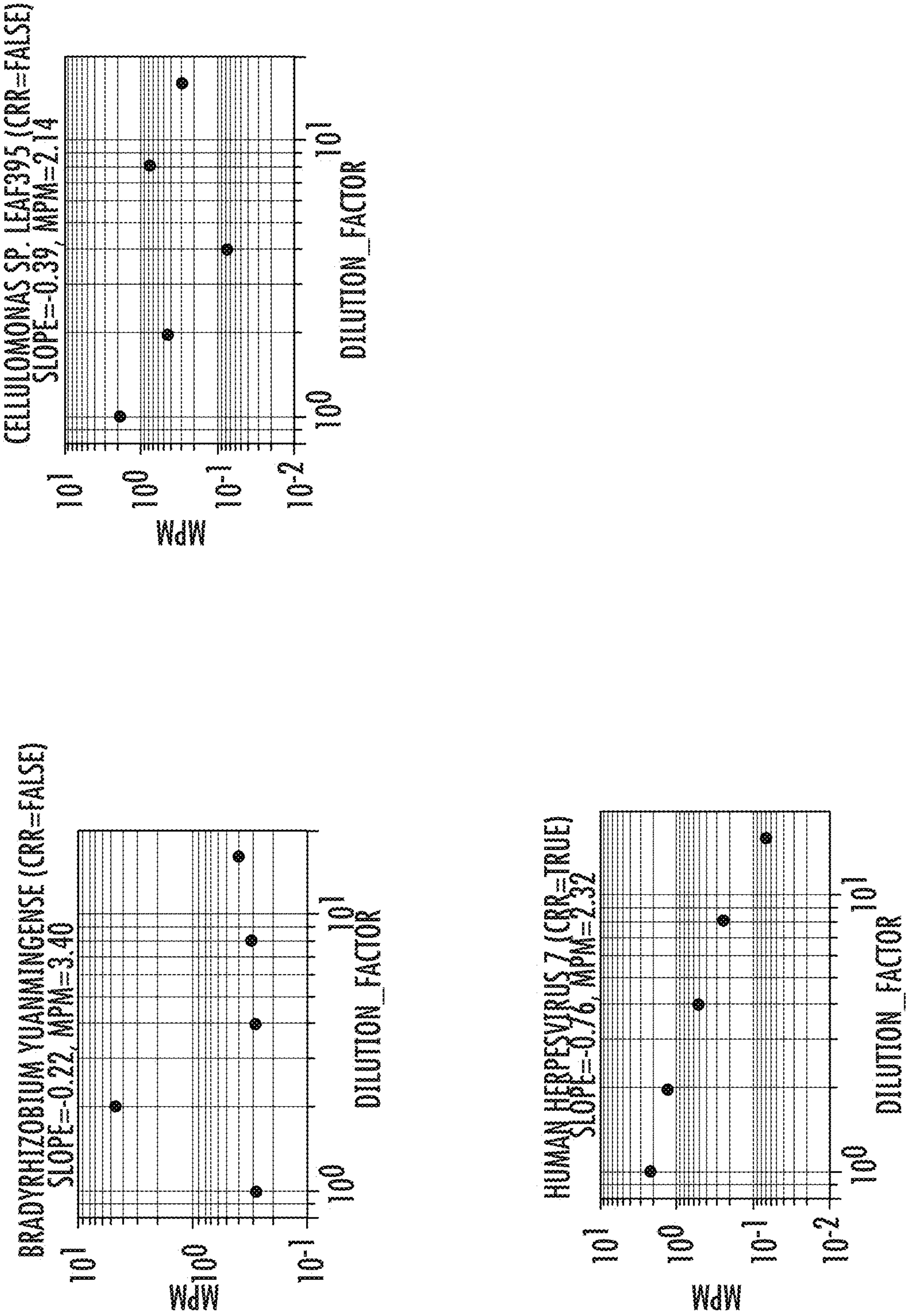
Figure 10F:
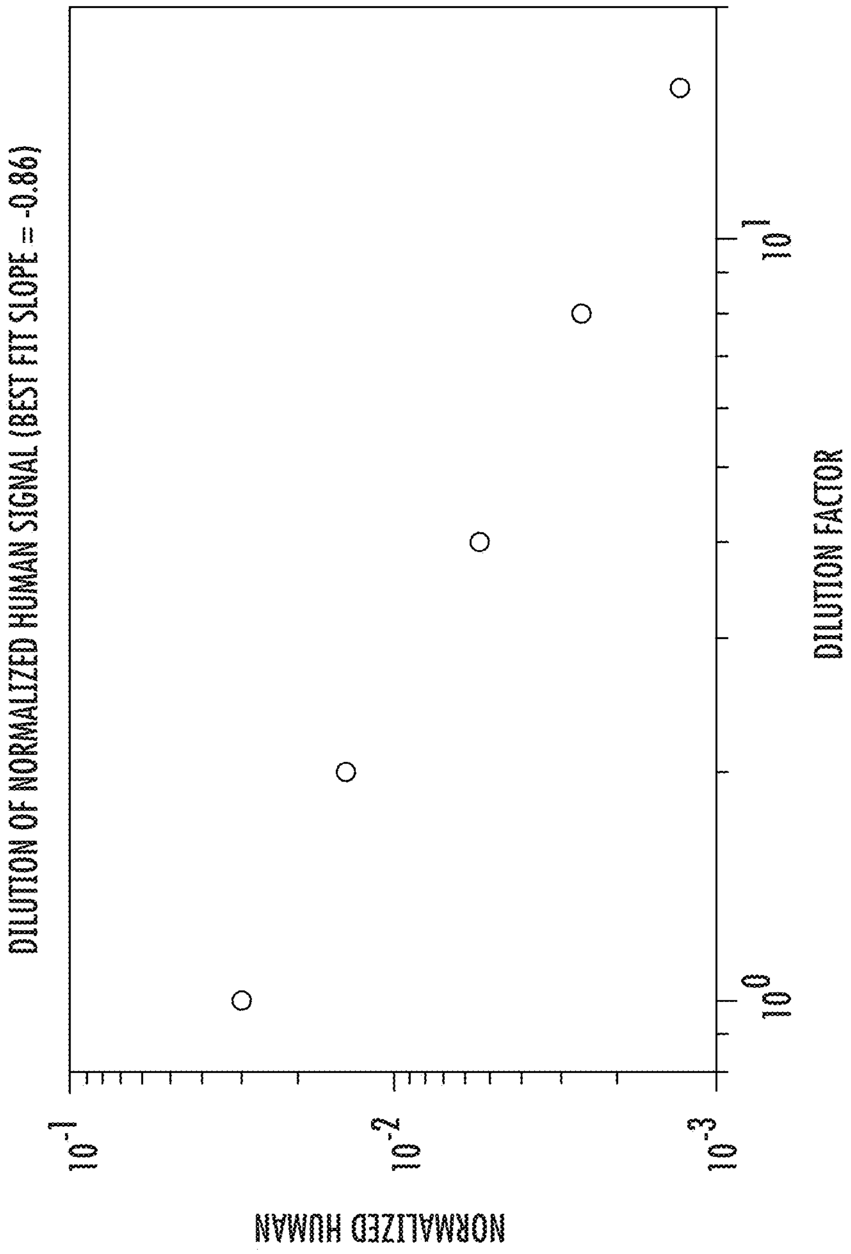

A sample of asymptomatic plasma was serially diluted (FIG. 10*a* with k=2) and the dilution series processed to obtain sequencing libraries as described above. Number of replicates of each member of the dilution series were 4, 4, 4, 8, and 16 for dilutions 1:1, 1:2, 1:4, 1:8, and 1:16, respectively, in order to generate comparable number of unique sequencing reads per microbial taxon or specie at all dilution factor tested. The libraries were then sequenced on NextSeq 500. FIG. 10*b* shows the depth of sequencing in all the libraries analyzed as part of this dilution series as indicated by the normalization spike-in molecule (ddSPANK). For each taxon, we formulated a likelihood for the concentration of that taxon in undiluted sample (assuming that it is absent from environmental contamination) given the number of reads that were observed in each element of the dilution series. We then did the same, but assumed that all inferred abundance for the taxon was contributed by environmental contamination rather than endogenous DNA within the plasma. The (log) ratio the maximums of these two likelihoods was visualized for each taxon against its most likely concentration under each model to pick out taxa with particularly large likelihood ratios given their concentration relative to known environmental contaminants at similar concentration (FIG. 10*c*). This smaller set of taxa and their abundance response in units of MPM (number of molecules per microliter) to sample dilution may then be inspected individually (FIG. 10*d* and FIG. 10*e*)to determine the goodness of fit (either visually or with an additional statistical test) of the inverse scaling of abundance with dilution factor. This final step may reveal taxa that obtained their large log likelihood by a random contamination affecting a more concentrated result (e.g. *Aspergillus glaucus* or *Bradyrhizobium yuanmingense*) in addition to those with more consistent scaling (e.g. *Bacteroides vulgatus* or Human herpesvirus 7). These later taxa are inferred to be highly likely to be present as endogenous signal in the original sample with their respective $C_S >> C_D$, $C_E$ as their inverse scaling across the dilution series is comparable to the calibrated inverse scaling across the dilution series obtained for the normalized human nucleic acid count in the data (i.e. a nucleic acid class that predominantly originates from the original sample), which accounts for the effects of the dilution on the process efficiencies and any differences between process yield for the target nucleic acids and normalization synthetic spike-ins (FIG. 10*f*). The later taxa may therefore not be penalized as false positives when detected in the resulting positive assay control. Note that this method can only distinguish between the two models at sufficient sequencing depth (which can be observed on the visualization just described). Therefore, for this method to be useful in qualifying positive assay controls, sequencing depth should be made high enough that it is possible to distinguish between the two models down to concentrations where it is highly unlikely for the assay to identify analytes.

While preferred embodiments of the present disclosed subject matter have been shown and described herein, it will be obvious to those skilled in the art that such embodiments are provided by way of example only. Numerous variations, changes, and substitutions will now occur to those skilled in the art without departing from the disclosed subject matter. It should be understood that various alternatives to the embodiments of the disclosed subject matter described herein may be employed in practicing the disclosed subject matter. It is intended that the following claims define the scope of the disclosed subject matter and that methods and structures within the scope of these claims and their equivalents be covered thereby.

What is claimed is:

1. A method of processing a sample, the method comprising:

a. providing a dilution series of a sample comprising target cell-free nucleic acids, the dilution series comprising (i) a first diluted sample obtained by diluting at least a portion of the sample comprising target cell-free nucleic acids or obtained by providing at least a portion of the undiluted sample, wherein the first diluted sample comprises a quantity of the target cell-free nucleic acids; and (ii) at least a second diluted sample, the second diluted sample obtained by diluting at least a portion of the sample comprising target cell-free nucleic acids, or a dilution thereof, wherein the second diluted sample comprises a lower concentration of the target cell-free nucleic acids compared to the first diluted sample, or comprises no target cell-free nucleic acids;

b. performing sample processing on the first diluted sample and the second diluted sample, wherein contaminant nucleic acids are possibly introduced during the sample processing of the first diluted sample and the second diluted sample;

c. quantifying cell-free nucleic acids within the first diluted sample and within the second diluted sample by performing a sequencing assay on at least a portion of the cell-free nucleic acids in the first diluted sample to produce a first quantitative value and performing a sequencing assay on at least a portion of cell-free nucleic acids in the second diluted sample, if present, to produce a second quantitative value; and d. comparing the first quantitative value with the second quantitative value, wherein a decrease in the second quantitative value compared to the first quantitative value confirms a presence of the target cell-free nucleic acids in the sample.

2. The method of claim 1, wherein the contaminant nucleic acids and the target cell-free nucleic acids are derived from an identical type of organism.

3. The method of claim 1, wherein the target cell-free nucleic acids or the contaminant nucleic acids comprise cell-free nucleic acids from a microbe, bacterium, or fungus.

4. The method of claim 1, wherein the contaminant nucleic acids comprise cell-free nucleic acids from a virus or a protozoan.

5. The method of claim 1, further comprising:

a. tagging at least a portion of the cell-free nucleic acids in the first diluted sample with a first tag identifying the first dilution and tagging at least a portion of the cell-free nucleic acids, if present, in the second diluted sample with a second tag different from the first and that identifies the second diluted sample.

6. The method of claim 1, wherein the sample is from a mammal.

7. The method of claim 1, wherein the sample is selected from the group consisting of blood, plasma, serum, cerebrospinal fluid, synovial fluid, bronchial-alveolar lavage, urine, stool, saliva, and a nasal sample.

8. The method of claim 1, wherein the first diluted sample is undiluted compared to the sample.

9. The method of claim 1, further comprising heating a reagent or a diluent to denature contaminant nucleic acids in the reagent or the diluent.

10. The method of claim 1, wherein the diluent is selected from the group consisting of a buffer, an extraction buffer, a suspension buffer, a lysis buffer, a reagent, a culture medium and a synthetic plasma substitute.

11. The method of claim 1, further comprising adding at least 1,000 unique spike-in synthetic nucleic acids to the sample, or to at least the first dilution or at least the second dilution in said plurality of dilutions.

12. The method of claim 1, wherein performing the sequencing assay on at least a portion of the cell-free nucleic acids in the first diluted sample produces first sequence reads, and performing the sequencing assy on at least a portion of the cell-free nucleic acids in the second diluted sample produces second sequence reads, and wherein the method further comprises aligning the first sequence reads or the second sequences reads to a collection of reference genomes to identify a microbe from which the target nucleic acids or the contaminant nucleic acids originated.

13. The method of claim 12, wherein the collection of reference genomes comprises sequenced genomes from at least one of the following: viruses, bacteria, protozoa, or fungi.

14. The method of claim 1, wherein the quantifying cell-free nucleic acids within the first diluted sample and within the second diluted sample is performed following statistical analysis.

15. The method of claim 1, wherein the method has a false positive rate of less than 3%.

16. The method of claim 1, further comprising using a control sample selected from the group consisting of: plasma from an asymptomatic human subject, a synthetic sample designed to mimic human plasma, and a sterile sample when performing the sample processing on the first diluted sample and the second diluted sample.

17. The method of claim 1, further comprising using a control sample comprising plasma from an asymptomatic human subject when performing the sample processing on the first diluted sample and the second diluted sample.

18. The method of claim 1, wherein the method does not comprise sequencing a common sequence of the 16S rRNA gene.

19. A method of processing a sample, the method comprising:

a. providing a sample series comprising a plurality of samples, wherein at least two of the plurality of samples may comprise different concentrations or quantities of target nucleic acids;

b. performing sample processing on the at least two of the plurality of samples in the sample series, wherein contaminant nucleic acids are possibly introduced during the sample processing of the at least two of the plurality of samples and wherein the contaminant nucleic acids and the target nucleic acids are derived from the same type of bacteria, the same type of fungi, the same type of viruses, or the same type of protozoa;

c. quantifying nucleic acids within the at least two of the plurality of samples in the sample series wherein the quantifying comprises performing a sequencing assay on the nucleic acids; and d. comparing relative quantities of the nucleic acids in the at least two samples in order to distinguish the target nucleic acids from the possible contaminant nucleic acids.

20. The method of claim 19, further comprising:

a. tagging the target nucleic acids in the first and second samples in the sample series with different tags that distinguish target nucleic acids from the first sample from target nucleic acids from the second sample.

21. The method of claim 19, wherein the target nucleic acids comprise cell-free nucleic acids, the contaminant nucleic acids comprise cell-free nucleic acids, or both the target nucleic acids and the contaminant nucleic acids comprise cell-free nucleic acids.

22. The method of claim 12, further comprising (a) assigning reads to the microbe and (b) determining a quantity of the microbe, wherein the microbe is a pathogen.

23. The method of claim 1, wherein the sample comprising target cell-free nucleic acids is a sample selected from the group consisting of: a serum sample, a cerebrospinal fluid sample, a synovial fluid sample, a bronchial-alveolar lavage sample, a saliva sample, and a urine sample.

24. The method of claim 19, wherein the plurality of samples are derived from a single sample selected from the group consisting of: a serum sample, a cerebrospinal fluid sample, a synovial fluid sample, a bronchial-alveolar lavage sample, a saliva sample, and a urine sample.

25. The method of claim 1, wherein the sample comprising target cell-free nucleic acids is a plasma sample comprising target cell-free nucleic acids.

26. The method of claim 19, wherein the plurality of samples are derived from a single plasma sample comprising target cell-free nucleic acids.

27. The method of claim 1, wherein the method:

a) further comprises providing a third diluted sample obtained by diluting at least a portion of the sample comprising target cell-free nucleic acids, or a dilution thereof, wherein the third diluted sample comprises a different concentration of the target cell-free nucleic acids compared to the first and second diluted sample;

b) further comprises performing sample processing on the third diluted sample;

c) further comprises quantifying cell-free nucleic acids within the third diluted sample by performing a sequencing assay on at least a portion of the cell-free nucleic acids in the third diluted sample to produce a third quantitative value; and d) further comprises comparing the first quantitative value or second quantitative value with the third quantitative value.

28. The method of claim 19, wherein the same type is a same species.

29. The method of claim 1, wherein the target cell-free nucleic acids or contaminant nucleic acids comprise cell free nucleic acids from a bacterium.

30. The method of claim 1, wherein the target cell-free nucleic acids or contaminant nucleic acids comprise cell free nucleic acids from a fungus.

31. The method of claim 1, wherein the target cell-free nucleic acids or contaminant nucleic acids comprise cell free nucleic acids from a protozoan.

32. The method of claim 1, wherein the target cell-free nucleic acids or contaminant nucleic acids comprise cell free nucleic acids from a virus.

33. The method of claim 19, and wherein the contaminant nucleic acids and the target nucleic acids are derived from the same type of bacteria.

34. The method of claim 19, and wherein the contaminant nucleic acids and the target nucleic acids are derived from the same type of fungi.

35. The method of claim 19, and wherein the contaminant nucleic acids and the target nucleic acids are derived from the same type of protozoa.

36. The method of claim 19, and wherein the contaminant nucleic acids and the target nucleic acids are derived from the same type of virus.

* * * * *